US009060966B2

(12) United States Patent
Cuevas Sánchez et al.

(10) Patent No.: US 9,060,966 B2
(45) Date of Patent: Jun. 23, 2015

(54) USE OF 2,5-DIHYDROXYBENZENE DERIVATIVES FOR THE TREATMENT OF ARTHRITIS AND PAIN

(76) Inventors: Pedro Cuevas Sánchez, Madrid (ES); Guillermo Gimenez Gallego, Madrid (ES); Inigo Saenz de Tejada Morgan, Madrid (ES); Maria Luisa Krauel, legal representative, Madrid (ES); Javier Angulo Frutos, Madrid (ES); Rosa Maria Lozano Puerto, Madrid (ES); Antonio Romero Garrido, Madrid (ES); Serafin Valverde Lopez, Madrid (ES)

( * ) Notice: Subject to any disclaimer, the term of this patent is extended or adjusted under 35 U.S.C. 154(b) by 1703 days.

(21) Appl. No.: 12/377,837

(22) PCT Filed: Aug. 15, 2007

(86) PCT No.: PCT/EP2007/058446
§ 371 (c)(1),
(2), (4) Date: Mar. 1, 2011

(87) PCT Pub. No.: WO2008/020033
PCT Pub. Date: Feb. 21, 2008

(65) Prior Publication Data
US 2011/0152222 A1    Jun. 23, 2011

(30) Foreign Application Priority Data

Aug. 16, 2006 (ES) ................................ 200602217
Jul. 2, 2007 (ES) ................................ 200701855

(51) Int. Cl.
| A61K 31/045 | (2006.01) |
| A61K 31/15 | (2006.01) |
| A61K 31/10 | (2006.01) |
| A61K 31/192 | (2006.01) |
| A61K 31/60 | (2006.01) |
| A61K 31/618 | (2006.01) |

(52) U.S. Cl.
CPC ............... *A61K 31/10* (2013.01); *A61K 31/192* (2013.01); *A61K 31/60* (2013.01); *A61K 31/618* (2013.01)

(58) Field of Classification Search
CPC ..... A61K 31/10; A61K 31/192; A61K 31/60; A61K 31/216
USPC .......................................... 514/730, 764, 825
See application file for complete search history.

(56) References Cited

FOREIGN PATENT DOCUMENTS

| CH | WO9011759 | * 10/1990 |
| CH | 682716 | * 11/1993 |
| GB | WO2005/023305 | * 3/2005 |

OTHER PUBLICATIONS

Sintov et al., Journal of Controlled Release, 2002, vol. 79, pp. 113-122.*
Banker et al., Modern Pharmaceutics, 3ed., Marcel Dekker, New York, 1996, p. 596.*
Roland Axmann el al., "Inhibition of Interleukin-6 Receptor Directly Blocks Osteoclast Formation In Vitro and In Vivo", Arthritis & Rheumatism, vol. 60, No. 9, Sep. 2009, pp. 2747-2756.
Loe A. B. Joosten et al., "IL-1 (alpha)(beta) Blockade Prevents Cartilage and Bone Destruction in Murine Type II Collagen-Induced Arthritis, Whereas TNF-(alpha} Blockade Only Ameliorates Joint inflammation", J. Immunol. 1999;163;5049-5055 http://www.jimmunol.org/cgi/content/full/163/9/5049.
Jeanne Keffer et al., "Transgenic mice expressing human tumour necrosis factor: a predictive genetic model of arthritis". The EMBO Journal, vol. 10, No. 13, pp. 4025-4031, 1991.
Ric Day, MD et al., "A Randomized Trial of the Efficacy and Tolerability of the COX-2 Inhibitor Rofecoxib vs Ibuprofen in Patients with Osteoarthritis", (Reprinted) Arch Intern Med/vol. 160, Jun. 26. 2000, pp. 1781-1787 www.archinternmed.com.
M. Yilmaz et al., "Cytokine Levels in Serum of Patients with Juvenile Rheumatoid Arthritis", Clinical Rheumatology (2001) 20:30-35.
C. Sommer et al., "Recent findings on how proinflammatory cytokines cause pain: peripheral mechanisms in inflammatory and neuropathic hyperalgesia", Neuroscience Letters 361 (2004) 187-187.
J.F. Morris et al., "Proceedings of the Anatomical Society of Great Britain and Ireland", J. Anat. (2002) 200, pp. 523-534.
R.Y. Kang et al., "Expression of Cyclooxygenase-2 in Human and an Animal Model of Rheumatoid Arthritis", British Journal of Rheumatology 1996;35:711-718.
Fionula M. Brennan et el., Review Series, "Evidence that cytokines play a role in rheumatoid arthritis", The Journal of Clinical Investigation, vol. 118, No. 11, Nov. 2008, pp. 3537-3545 http://www.jci.org.
Gregory Livshits et al., "Interleukin-6 is a Significant Predictor of Radiographic Knee Osteoarthritis", Arthritis & Rheumatism, vol. 60, No. 7. Jul. 2009, pp. 2037-2045.
Eli Eliav et al., "The role of IL-6 and IL-1β in painful perineural inflammatory neuritis", Brain, Behavior, and Immunity 23 (2009) 474-484.
F. Pessler et al., "Increased Angiogenesis and Cellular Proliferation as Hallmarks of the Synovium in Chronic Septic Arthritis", Arthritis & Rheumatism (Arthritis Care & Research) vol. 59, No. 8, Aug. 15, 2008, pp. 1137-1146.
Daniel Brenn et al., "Sensitization of Unmyelinated Sensory Fibers of the Joint Nerve to Mechanical Stimuli by Interleukin-6 in the Rat", Arthritis & Rheumatism, vol. 56, No. 1, Jan. 2007, pp. 351-359.
Ashok R. Amin et al., "Superinduction of Cyclooxygenase-2 Activity in Human Osteoarthritis-affected Cartilage", vol. 99, No. 6, Mar. 1997, pp. 1231-1237.
Sadaf Ashraf et al., "Angiogenesis in Osteoarthritis", Current Opinion in Rheumatology 2008, 20:573-580.

(Continued)

*Primary Examiner* — Sreeni Padmanabhan
*Assistant Examiner* — Shobha Kantamneni
(74) *Attorney, Agent, or Firm* — Frommer Lawrence & Haug LLP

(57) ABSTRACT

The present invention relates to the use of a compound of Formula (I''') or pharmaceutically acceptable salt or solvate, isomer or prodrug thereof in the manufacturing of a medicament for the treatment and/or prophylaxis of arthritis and pain.

7 Claims, 29 Drawing Sheets

(56) References Cited

OTHER PUBLICATIONS

Irmgard Tegeder et al., "Effects of selective COX-1 and -2 inhibition on formalin-evoked nociceptive bahaviour and prostaglandin E2 release in the spinal cord", Journal of Neurochemistry, 2001, 79, pp. 777-786.

C.S. Bonnet et al., "Osteoarthritis, angiogenesis and inflammation", Rheumatology 2005;44:7-16.

Thomas Pap et al., Editorial, "Linking Angiogenesis to Bone Destruction in Arthritis", Arthritis & Rheumatism, vol. 52, No. 5, May 2005, pp. 1346-1348.

Javier Mazario et al., "Cyclooxygenase-1 vs. cyclooxygenase-2 inhibitors in the induction of antinociception in rodent withdrawal reflexes", Neuropharmacology 40 (2001) 937-946.

Bailin Liang et al., Research, "Evaluation of anti-IL-6 monoclonal antibody therapy using murine type II collagen-induced arthritis", Journal of Inflammation 2009, 6:10.

Raymond N. Dubois et al., "Cyclooxygenase in biology and disease", The FASEB Journal, vol. 12, Sep. 1998. pp. 1063-1073.

Robert R. Edwards et al., Research article, "Enhanced reactivity to pain in patients with rheumatoid arthritis", Arthritis Research and Therapy, vol. 11, No. 3 http://arthritis-research.com/content/11/3/R61.

Roberto Caporali et al., Treatment of rheumatoid arthritis with anti-TNF-alpha agents; A reappraisal, Autoimmunity Reviews, 8 (2009) 274-280.

Otilia Obreja et al., Interleukin-6 in combination with its soluble IL-6 receptor sensitises rat skin nociceptors to heat, in vivo Pain 96 (2002) 57-62.

Virginia Pascual et al., "Role of interleukin-1 (IL-1) in the pathogenesis of systemic onset juvenile idiopathic arthritis and clinical response to IL-1 blockade", vol. 201, No. 9, May 2, 2005 pp. 1479-1486 www.jem.org/cgi/doi/10.1084/jem.20050473.

Mei Chen et al., "Predominance of Cyclooxygenase 1 Over Cyclooxygenase 2 in the Generation of Proinfammatory Prostaglandins in Autoantibody-Driven K/BxN Serum-Transfer Arthritis", vol. 58, No. 5, May 2008. pp. 1354-1365.

A E Koch, Report, "Angiogenesis as a target in rheumatoid arthritis", Ann Rheum Dis 2003,62(Suppl II):ii60-ii67 www.annrheumdis.com.

Michael M. Ndengele at al., "Cyclooxygenases 1 and 2 contribute to peroxynitrite-mediated inflammatory pain hypersensivity", The FASEB Journal, vol. 22, Sep. 2008, pp. 3154-3164.

Wolfgang Koppert et al., "The cyclooxygenase isozyme inhibitors parecoxib and paracetamol reduce central hyperalgesia in humans", Pain 108 (2004) 148-153.

Norihiro Nishimoto et al., "Treatment of Rheumatoid Arthritis with Humanized Anti-Interleukin-6 Receptor Antibody", vol. 50, No. 6, 2004, pp. 1761-1769.

David Yocum, MD et al., "Safety and Efficacy of Meloxicam in the Treatment of Osteoarthritis", (Reprinted) Arch Intern Med/vol. 160, Oct. 23, 2000. pp. 2947-2954 www.archinternmed.com.

* cited by examiner

USE OF 2,5-DIHYDROXYBENZENE DERIVATIVES FOR THE TREATMENT OF ARTHRITIS AND PAIN

RELATED APPLICATIONS

This application is a national stage filing under 35 U.S.C. §371 of International Application Number PCT/EP07/58446, filed Aug. 15, 2007, which claims the benefit of priority under 35 U.S.C. §119 of ES Application No. P200602217, filed Aug. 16, 2006 and of ES Application No. P200701855, filed Jul. 2, 2007. The foregoing applications, and all documents cited therein, are hereby incorporated herein by reference in their entirety.

FIELD OF THE INVENTION

The invention relates to the use of 2,5 dihydroxybenzene compounds and derivatives thereof, its pharmaceutically acceptable salts and solvates, as well as the isomers and prodrugs thereof for the treatment of certain diseases, specifically, for the treatment of hemangiomas, hemangioblastomas, benign prostatic hyperplasia, Barrett's disease, asthma, skeletal muscle and tendon repair, Crohn's disease, ulcerative colitis (proctitis, proctosigmoiditis, pancolitis), leishmaniasis, diseases associated to *Helicobacter pylori* infection, pterygium, endometriosis, ovarian hyperstimulation syndrome, polycystic kidney disease, pain, arthritis; and eye diseases associated to or that include, but not limited to, macular degeneration, corneal neovascularization or angiogenesis, iris neovascularization or angiogenesis, retinal neovascularization or angiogenesis, diabetic proliferative retinopathy and non-diabetic proliferative retinopathy, through the administration of a compound including at least one 2,5-dihydroxybenzene compound or a pharmaceutically acceptable salt thereof and, optionally, at least one therapeutic agent.

BACKGROUND OF THE INVENTION

The hemangioma is the most frequent tumor in childhood. Besides surgery which, sometimes is difficult to carry out due to the extent or localization of the tumors, there are no effective treatments approved by health authorities to treat hemangiomas. Likewise, other vascular tumors such as the hemangioblastoma are difficult to treat.

Pterygium is an angiodependant corneal disease originated due to the activation and proliferation of limbal epithelial stem cells (Dushku N, Reid T W. *Curr Eye Res*, 1994). Likewise, corneal and retinal neovascularization may cause visual impairments and blindness. Diabetic retinopathy is the main cause of blindness on people over 20.

The *Helicobacter pylori*, is a Gram negative bacteria that infects at least 50% of the world population, and may cause several gastrointestinal diseases such as chronic gastritis, gastric and duodenal ulcer and stomach cancer (Suerbaum S, Michetti P. *N Engl J Med*, 2002). *H. pylori* infections predispose to the development and progression of stomach cancer (Yeo M et al. *Gut*, 2006).

Barrett's disease is originated by gastroesophageal reflux that transforms the esophagus normal squamous epithelium into a columnar epithelium. This process may produce adenocarcinomas.

Ulcerative colitis (proctitis, proctosigmoiditis, pancolitis) is a disease that causes ulcers in the rectum and colon producing bleeding and diarrhea.

Crohn's disease is an autoimmune chronic disease producing intestinal inflammation. Even if it may affect the whole gastrointestinal tract, most frequently it affects the ileum.

Arthritis is a usually chronic condition that causes stiffness, pain and sometimes joint swelling (it includes osteoarthritis, rheumatoid arthritis, gouty arthritis, lupus-related arthritis, and the like).

Asthma is a chronic disease that affects the airways constricting them. Current therapies for asthma are partially effective, and it is still one of the main causes of infant mortality.

Endometriosis or the growth of the endometrium outside de uterus is a disease that affects 10-15% of women of reproductive age. Endometriosis is associated with dysmenorrhea, abdominal pain, dysuria; and among 30% of affected women, infertility. Nowadays there is no effective treatment for endometriosis or for benign prostatic hyperplasia (Snowartz F et al. Histol Histopathol, 2000; Boget S et al. *Eur J Endocrinol*, 2001).

Benign prostatic hyperplasia is a disease in which the prostate gland is considerably enlarged and may cause micturition-related alterations. Even if there are pharmacological treatments for benign prostatic hyperplasia, their efficacy is limited and, in the end, many patients require surgery with at least a partial resection of the gland.

Every year, in the United States, 6 million people suffer from musculoskeletal diseases, mainly, fiber breaking (Mc-Clatchey K D. *Arch Pathol Lab Med*, 2004). Regeneration of damaged muscle implies a process that frequently causes alterations in the muscular function. Currently, there are no effective therapies to treat muscle injuries.

The ovarian hyperstimulation syndrome is a iatrogenic, and potentially fatal complication produced by ovulation induction in infertility treatments. The clinical characteristics of the syndrome are produced by a severe inflammatory reaction that produces massive accumulation of extravascular fluid. Other clinical symptoms include hypercoagulability, thromboembolic conditions, respiratory distress syndrome, and death.

The polycystic kidney disease is the most common hereditary kidney disease, with a prevalence of 1:1000. The affected patients are candidates for kidney transplantation. These patients comprise from 5 to 10% of kidney transplant receivers. One characteristic of this disease is hypervascularization of the pericystic area with the formation of new blood vessels on the cyst wall, which suggests that angiogenesis is an important factor in the progression of the renal cystic disease (Bernhardt W M et al. *Am J Physiol*, 2007).

Leishmaniasis, produced by the parasitation of species of the genus *Leishmania*, is the third most important disease among vector-transmitted diseases. It is transmitted to mammals, including humans, by the bite of mosquitoes of the genus *Phlebotomus*. It is estimated that every year, there are 1.5-2 million cases of leishmaniasis worldwide, and that 350 million people are in risk of suffering from the disease. Leishmaniasis is associated to a wide variety of clinical symptoms that include, skin ulcerative lesions in the area of the bite (localized cutaneous leishmaniasis), multiple non-ulcerative nodules (diffuse cutaneous leishmaniasis), inflammation and destruction of the mucosa (mucosal leishmaniasis) and disseminated visceral infection, potentially fatal (leishmaniasis visceral) (Murray et al. *Lancet*, 2005). The current treatment for leishmaniasis comprises pentavalent antimonial salts, mainly Pentosam (sodium stibogluconate) and Glucantime (N-methylglucamine antimoniate). These treatments are associated with important side effects affecting the kidney, the liver and the heart (Ouellete M J et al. *Drug Resist*

*Updates*, 2004). Therefore, there is a considerable clinical interest in finding new, safe and efficient treatments for leishmaniasis.

Pain is an unpleasant emotional (subjective) and sensorial (objective) experience associated to a lesion. This is the main reason why patients demand medical consultation.

Therefore and in spite of the recent scientific advances and of knowledge about the etiology of many diseases described in this invention, there are not really effective treatments for those diseases.

SUMMARY OF THE INVENTION

Inventors have surprisingly found that 2,5-dihydroxybenzene derivatives, its pharmaceutically accepted salts and solvates, as well as isomers and prodrugs thereof are useful to manufacture drugs to treat hemangiomas, hemangioblastomas, benign prostatic hyperplasia, Barrett's disease, asthma, skeletal muscle and tendon repair, Crohn's disease, ulcerative colitis (proctitis, proctosigmoiditis, pancolitis), leishmaniasis, diseases associated to *Helicobacter pylori* infection, pterygium, endometriosis, ovarian hyperstimulation syndrome, polycystic kidney disease, pain, arthritis; and eye diseases associated to or that include, but not limited to, macular degeneration, corneal neovascularization or angiogenesis, iris neovascularization or angiogenesis, retinal neovascularization or angiogenesis, diabetic proliferative retinopathy and non-diabetic proliferative retinopathy Thus, a first aspect of the present invention relates to the use of a compound of Formula (I''') or pharmaceutically acceptable salt or solvate, isomer or prodrug thereof in the manufacturing of a medicament for the treatment and/or prophylaxis of arthritis and pain, wherein the compound of Formula (I''') is:

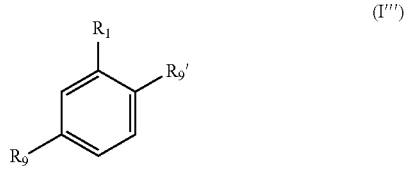

(I''')

wherein:
R$_1$ is —(CH$_2$)$_a$Y or —CH=CH—(CH$_2$)$_p$Z;
Y is —SO$_3$H, —SO$_3^-$.X$^+$, —SO$_3$R$_3$, —PO$_3$H, —PO$_3$—.X$^+$, —PO$_3$R$_3$;
Z is —SO$_3$H, —SO$_3^-$.X$^+$, —SO$_3$R$_3$, —PO$_3$H, —PO$_3$—.X$^+$, —PO$_3$R$_3$, —CO$_2$H, —CO$_2^-$.X$^+$ or —CO$_2$R$_3$;
X$^+$ is an organic cation or an inorganic cation, such that the general charge of the compound is neutral;
R$_9$ and R$_{9'}$ are independently selected from —OH and —OR$_2$, wherein when R$_9$ and R$_{9'}$ are both —OR$_2$, then said R$_9$ and R$_{9'}$ can be the same or different;
R$_2$ is a substituted or unsubstituted alkyl group, a substituted or unsubstituted aryl group, a substituted or unsubstituted alkylsulfonyl group, a substituted or unsubstituted arylsulfonyl group, a substituted or unsubstituted alkylcarbonyl group or a substituted or unsubstituted arylcarbonyl group;
R$_3$ is a substituted or unsubstituted alkyl group or a substituted or unsubstituted aryl group;
a is number selected from 0, 1, 2, 3, 4, 5 and 6;
p is an integer selected from 0, 1, 2, 3, 4, 5 and 6,
with the proviso that when Y is —SO$_3$H, —SO$_3^-$.X$^+$ or —SO$_3$R$_3$, then R$_9$ and R$_{9'}$ are independently selected from —OH and —OR$_2$, wherein at least one of R$_9$ and R$_{9'}$ is a substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group.

Another aspect of the invention relates to a method for the treatment and/or prophylaxis of any of the diseases selected from the group consisting of arthritis and pain, comprising administering to a subject in need thereof an effective amount of a 2,5-dihydroxybenzene derivative represented by Formula (I''') or a pharmaceutically acceptable salt or solvate thereof, isomer or prodrug thereof, wherein the compound of Formula (I''') is:

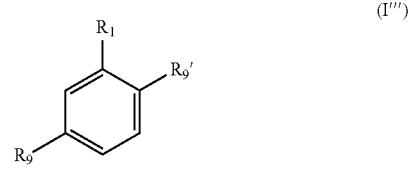

(I''')

wherein:
R$_1$ is —(CH$_2$)$_a$Y or —CH=CH—(CH$_2$)$_p$Z;
Y is —SO$_3$H, —SO$_3^-$.X$^+$, —SO$_3$R$_3$, —PO$_3$H, —PO$_3$—.X$^+$, —PO$_3$R$_3$;
Z is —SO$_3$H, —SO$_3^-$H, —SO$_3^-$RX$^+$, —SO$_3$R$_3$, —PO$_3$H, —PO$_3$—.X$^+$, —PO$_3$R$_3$, —CO$_2$H, —CO$_2^-$.X$^+$ or —CO$_2$R$_3$;
X$^+$ is an organic cation or an inorganic cation, such that the general charge of the compound is neutral;
R$_9$ and R$_{9'}$ are independently selected from —OH and —OR$_2$, wherein when R$_9$ and R$_{9'}$ are both —OR$_2$, then said R$_9$ and R$_{9'}$ can be the same or different;
R$_2$ is a substituted or unsubstituted alkyl group, a substituted or unsubstituted aryl group, a substituted or unsubstituted alkylsulfonyl group, a substituted or unsubstituted arylsulfonyl group, a substituted or unsubstituted alkylcarbonyl group or a substituted or unsubstituted arylcarbonyl group;
R$_3$ is a substituted or unsubstituted alkyl group or a substituted or unsubstituted aryl group;
a is number selected from 0, 1, 2, 3, 4, 5 and 6;
p is an integer selected from 0, 1, 2, 3, 4, 5 and 6.
with the proviso that when Y is —SO$_3$H, —SO$_3^-$.X$^+$ or —SO$_3$R$_3$, then R$_9$ and R$_{9'}$, are independently selected from —OH and —OR$_2$, wherein at least one of R$_9$ and R$_{9'}$ is a substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group.

These and other aspects of the present invention are described in detail herein.

Photographs showing the effects of a topical treatment with a cream comprising 2,5-dihydroxybenzenesulfonic (DHBS) in a child suffering from Nakagawa angioblastoma. Panel A shows the appearance of the child before treatment, and Panel B shows the child after the topical treatment with 2,5 dihydroxybenzenesulfonic (DHBS) twice a day for 1 month. A decrease in the intensity of the coloration of the hemangioblastoma may be clearly observed.

Figure 3:
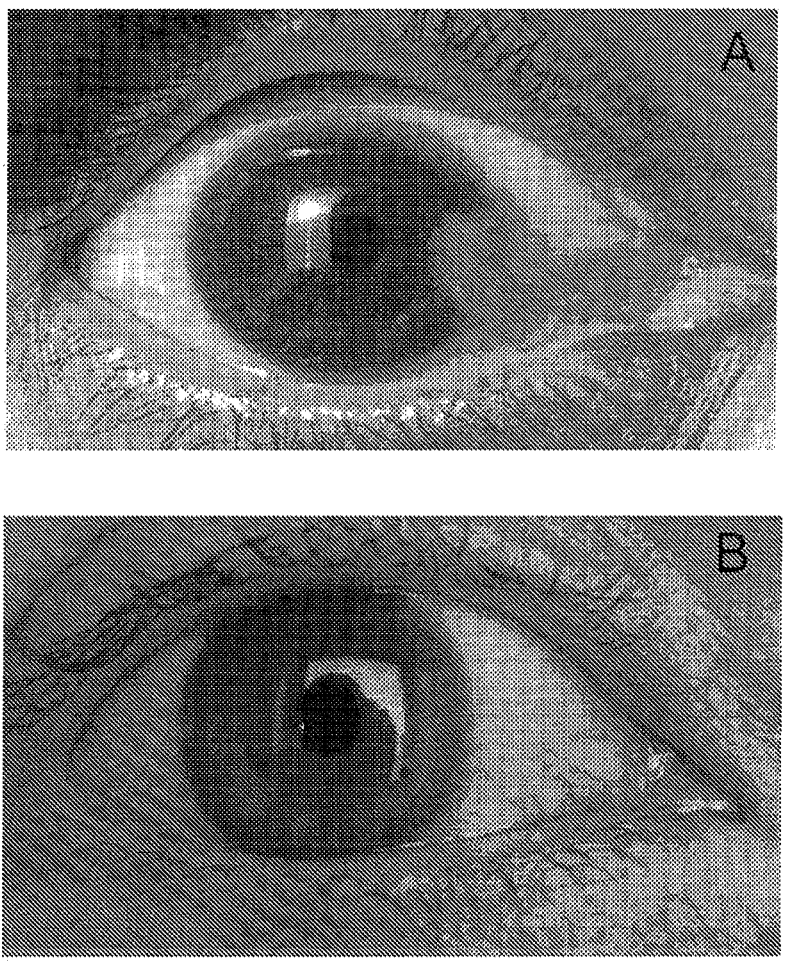

FIG. 3. Pterygium.
A) The photograph shows the presence of pterygium in a patient before the treatment.
B) The photograph shows the presence of pterygium in a patient after the topical treatment with the solution containing 2.5% of 2,5 dihydroxybenzenesulfonic acid (DHBS). The treatment consists of the application of 4 drops of said solution daily, for two weeks.

Figure 4:
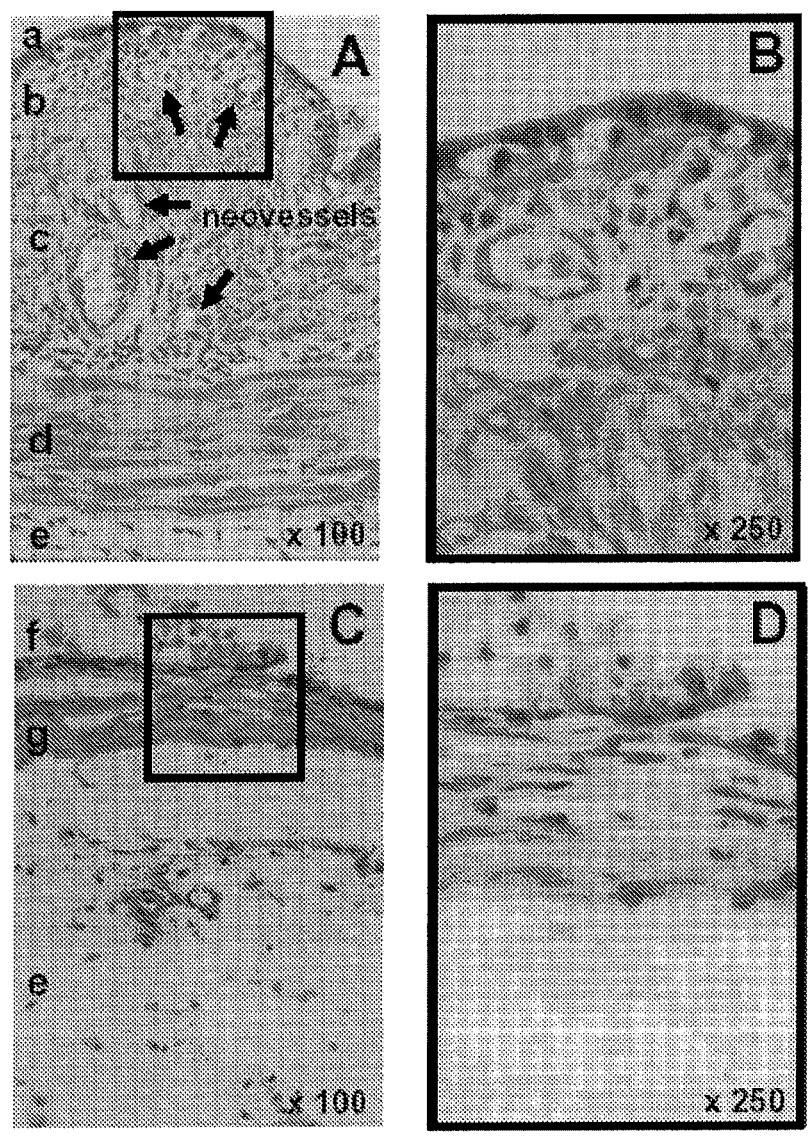

FIG. 4. Endometriosis.

Histological changes caused by 2,5-dihydroxybenzenesulfonic (DHBS) in the uterine tissue implanted in the peritoneal cavity of a rat model with endometriosis.
A) Two weeks after the autologous implantation in the peritoneal cavity of female rats, the uterine tissue revealed an apparent viability in the control rats. In these rats, the epithelial layer (a) and the stroma (b) are clearly observed in the endometrium, while longitudinal (c) and circular (d) normal layers of smooth muscle cells are observed in the myometrium adjacent to the peritoneal tissue (e). The arrows show the neovascularization.
B) Magnification of the area marked with a box in A.
C) Degeneration of the uterine tissue implanted in a rat intraperitoneally injected with 2,5-dihydroxybenzenesulfonic (DHBS) (200 mg/kg/day in 0.9% NaCl) for two weeks (C) is observed. The loss of the epithelial layer (f) and the absence of stroma in the endometrium as well as myometrium atrophy (g) adjacent to the peritoneal tissue (e) were observed in this rat. The neovascularization observed in the uterine tissue implanted in control rats (shown with arrows in A) is not present in rats treated with 2,5-dihydroxybenzenesulfonic (DHBS) (C).
D) Magnification of the area marked with a box in C.

Figure 5:
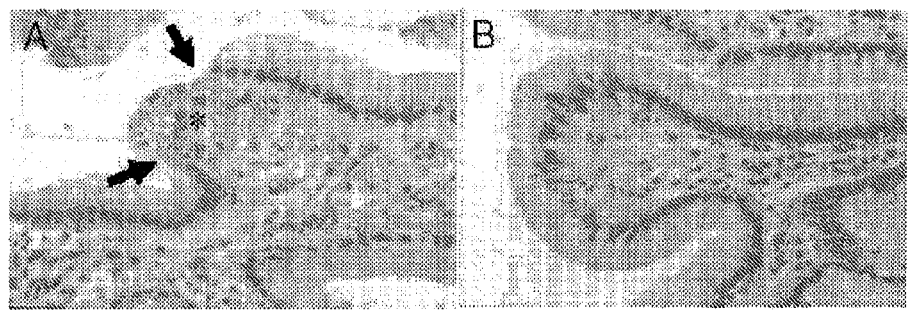

FIG. 5. *Helicobacter pylori*
A) Hematoxylin-eosin staining of the gastric mucosa of a sample obtained from a patient infected with *Helicobacter pylori* before treatment. The arrows and the asterisk indicate the formation of neovessels in the mucosa protruding the gastric lumen through the lost epithelial layer.
B) Hematoxylin-eosin staining of the gastric mucosa of a sample obtained from the same patient infected with *Helicobacter pylori* after administering 500 mg of 2,5-dihydroxybenzenesulfonate (DHBS) daily for a week. Gastric mucosa presents normal appearance.

Figure 6:
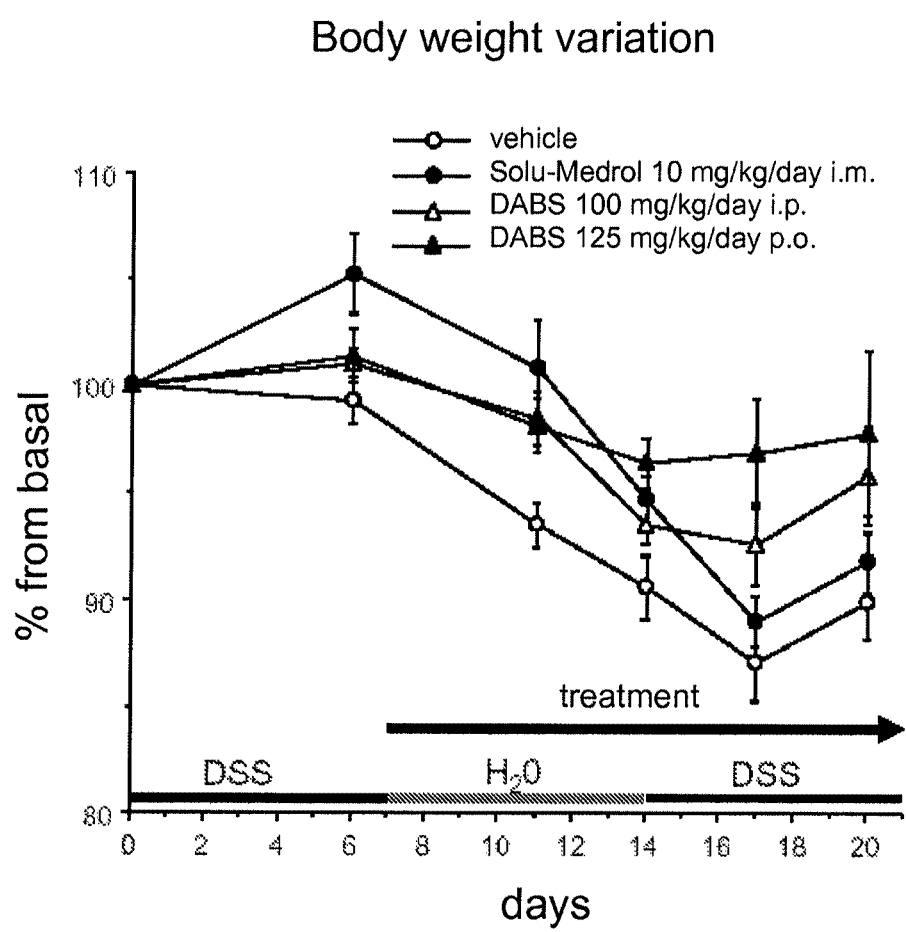

FIG. 6. Intestinal Inflammatory Disease.

Effect of potassium 2,5-diacetoxybenzene sulfonate on body weight loss in mice with experimentally induced intestinal inflammatory disease in a model applicable to the evaluation of treatments for ulcerative colitis and Crohn's disease. The mice were subject to two 7-day cycles of exposure to dextran sulfate sodium (DSS) (from day 1 to 7 and from day 14 to 21) in the drinking water separated by 7 days in which regular water was provided (from 7 to 14). One group was treated with vehicle (0.9% NaCl), another with Solu-Medrol (10 mg/kg/day i.m.), and the other two groups with potassium 2,5-diacetoxybenzene sulfonate (DABS), one of them with 100 mg/kg/day i.p. and the other with 125 mg/kg/day, orally (p.o.). The body weight was normalized on day 0. Data are expressed as the mean±SD of the percentage of the basal weight (day 0) of 10 mice per group. All the treatments had a significant effect on the body weight compared to the group treated with vehicle.

Figure 7:
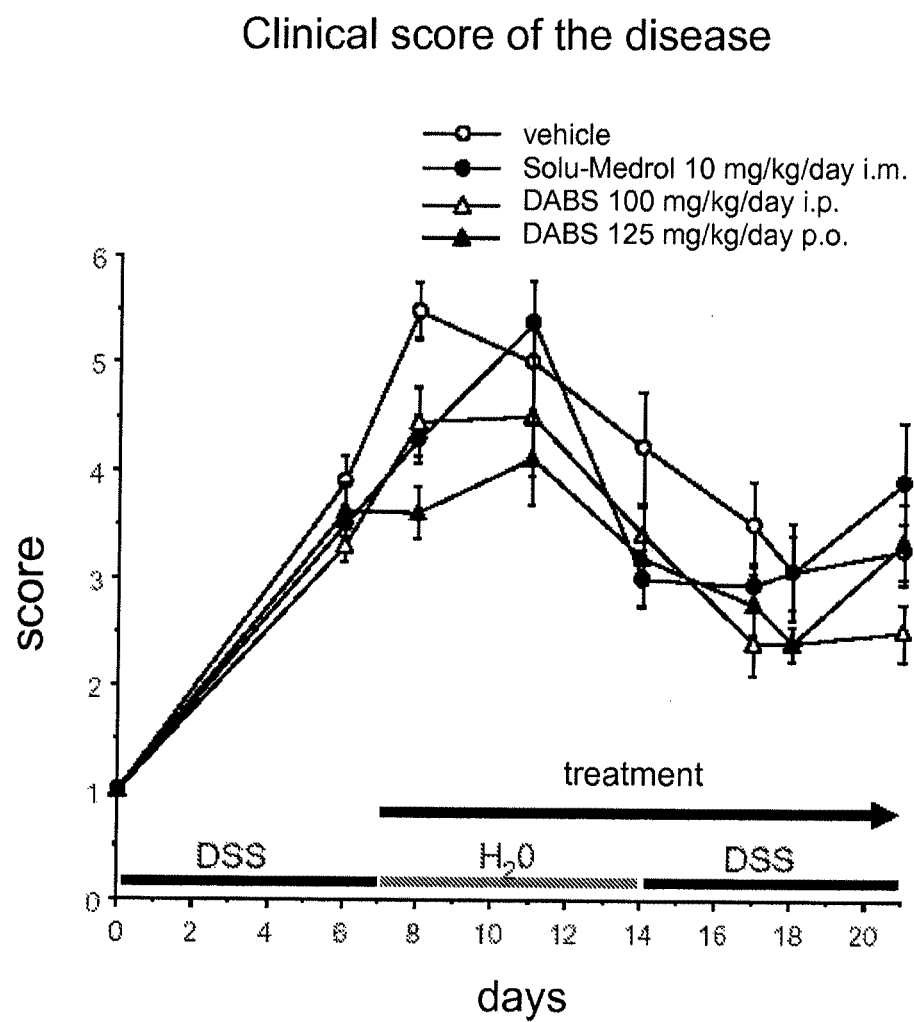

FIG. 7. Intestinal Inflammatory Disease

Effect of potassium 2,5-diacetoxybenzene sulfonate on the clinical score of the disease in mice with experimentally induced intestinal inflammatory disease in a model applicable to the evaluation of treatments for ulcerative colitis and Crohn's disease. The mice were subject to two 7-day cycles of exposure to dextran sulfate sodium (DSS) (from day 1 to 7 and from day 14 to 21) in the drinking water separated by 7 days in which regular water was provided (from 7 to 14). One group was treated with vehicle (0.9% NaCl), another with Solu-Medrol (10 mg/kg/day i.m.), and the other two groups with potassium 2,5-diacetoxybenzene sulfonate (DABS), one of them with 100 mg/kg/day i.p. and the other with 125 mg/kg/day, orally (p.o.) Data are expressed as the mean±SD of the clinical score of the disease continuously obtained from 10 mice per each group.

FIG. 8. Asthma

Effect of potassium 2,5-diacetoxybenzene sulfonate (DABS) on bronchoconstriction in asthmatic mice treated with methacholine. All the mice were exposed to nebulized methacholine (MC; 5 and 20 mg/ml). Bronchoconstriction was determined as the enhanced pause. ($P_{enh}$), calculated as described in the corresponding example (example 13). As control, the background and the exposure to nebulized saline (0.9% NaCl) are shown. * p<0.05 vs. saline. The groups of mice treated with Combivent or DABS do not show a significant increase of the $P_{enh\ enh}$ after exposure to MC.

FIG. 9. Asthma

Effect of potassium 2,5-diacetoxybenzene sulfonate (DABS) on the inflammatory cell count in the bronchoalveolar lavage (BAL) in asthmatic mice. The data are expressed as mean±SEM of the total number of detected cells in the BAL of the right lung of each animal. * p<0.05, *** p<0.001 vs. group treated with vehicle.

Figure 10:
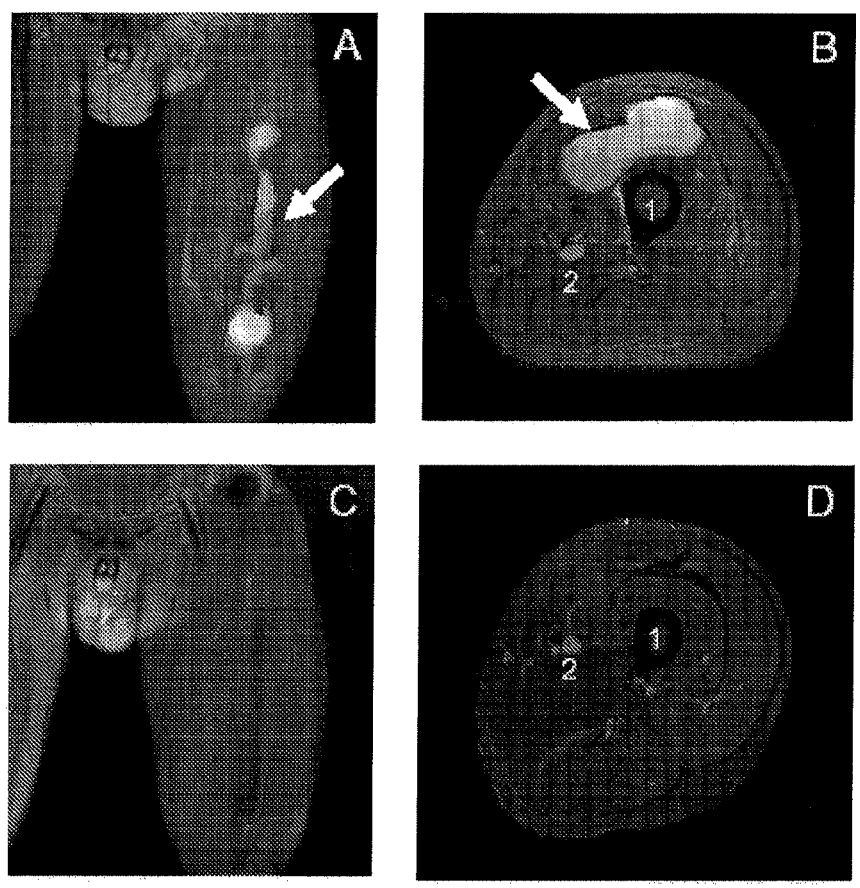

FIG. 10. Skeletal Muscle.

A and B are, respectively, front and cross sectional magnetic resonance images (MRI) showing the breaking of the left quadriceps in a patient, immediately before treatment. The presence of a large hematoma, indicated by arrows, may be observed. C and D are, respectively, front and cross sectional MRI showing the quadriceps of the same patient after treatment with 2,5-dihydroxybenzene sulfonic acid (DHBS) (500 mg/day p.o. for two weeks). It may be observed that the hematoma has disappeared. 1 indicates the femur and 2 indicates the femoral vessels.

Figure 11:
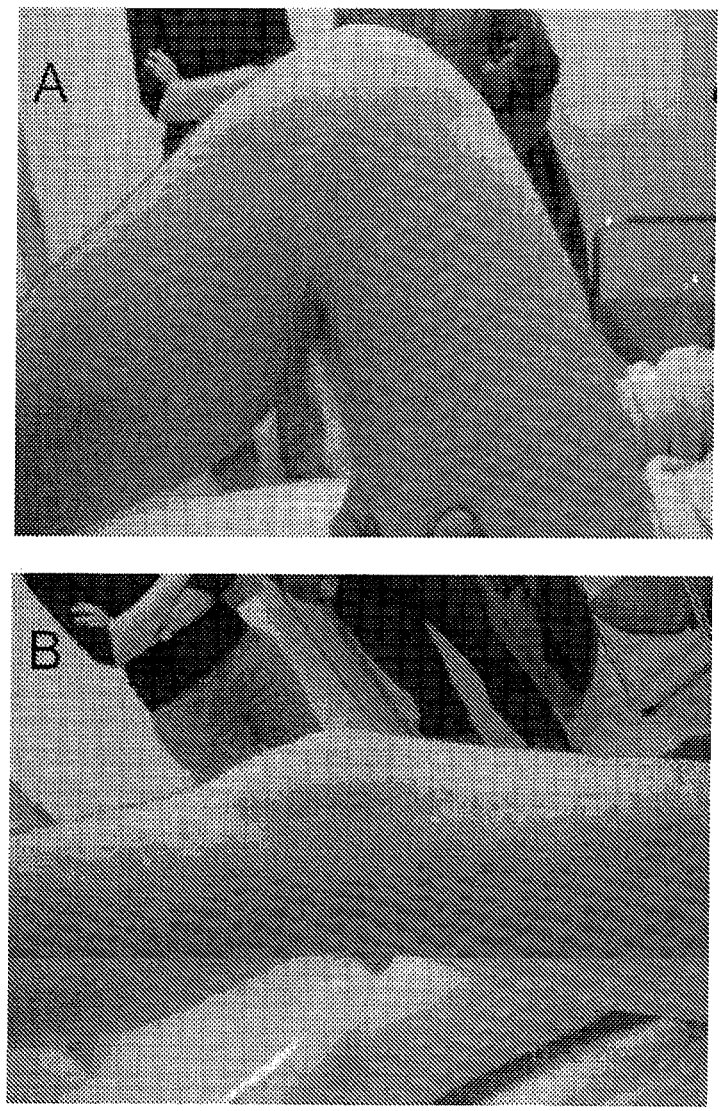

FIG. 11. Skeletal Muscle.

Images showing an almost complete flexion (A) and extension (B) capacity of the right lower limb in a patient (the same to which correspond the images of FIG. 10) with quadriceps breaking, after two weeks of oral treatment with 2,5 dihydroxybenzene sulfonic acid (DHBS) (500 mg/day).

Figure 12:
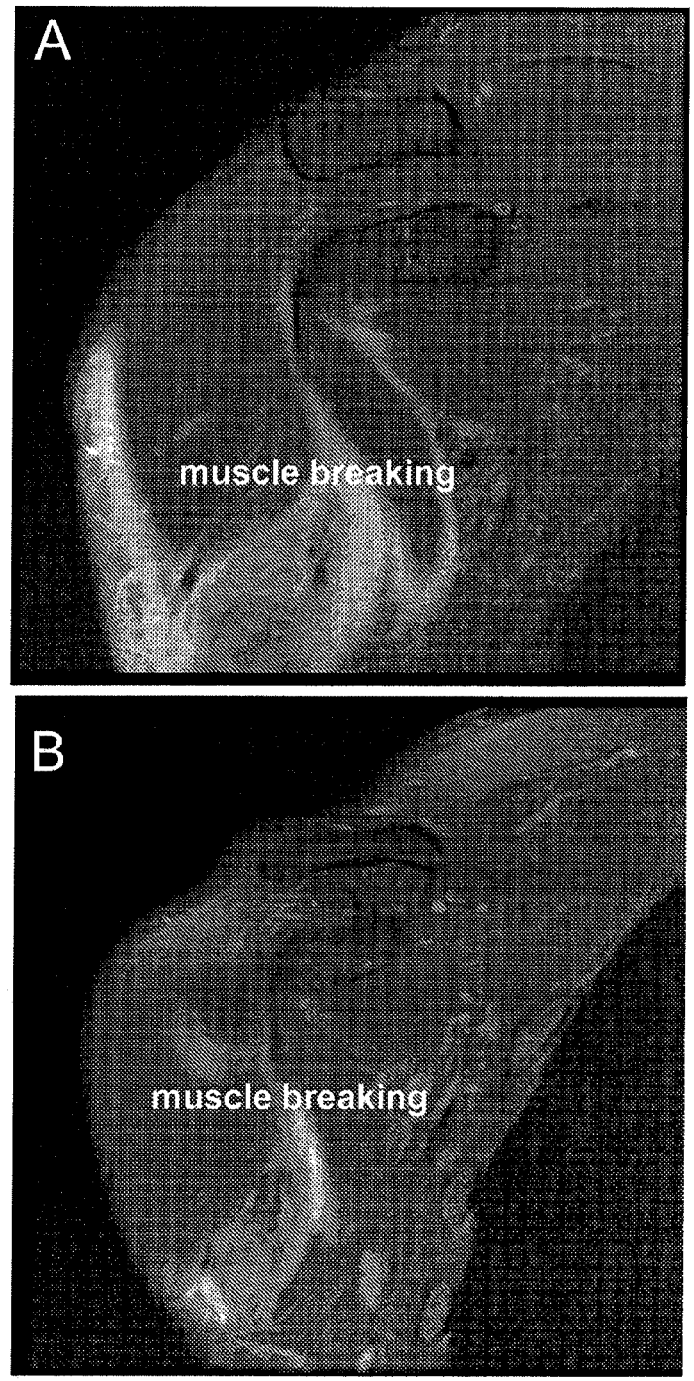

FIG. 12. Skeletal Muscle.

A is a Magnetic Resonance Image (MRI) of a patient showing the breaking of the right arm brachial biceps one day after the lesion and immediately before the treatment. B is the MRI of the same patient after being treated with 2,5-dihydroxybenzene sulfonic acid (DHBS) (1500 mg/day p.o. for 20 days) A remarkable reduction in the size of the lesion may be observed.

Figure 13:
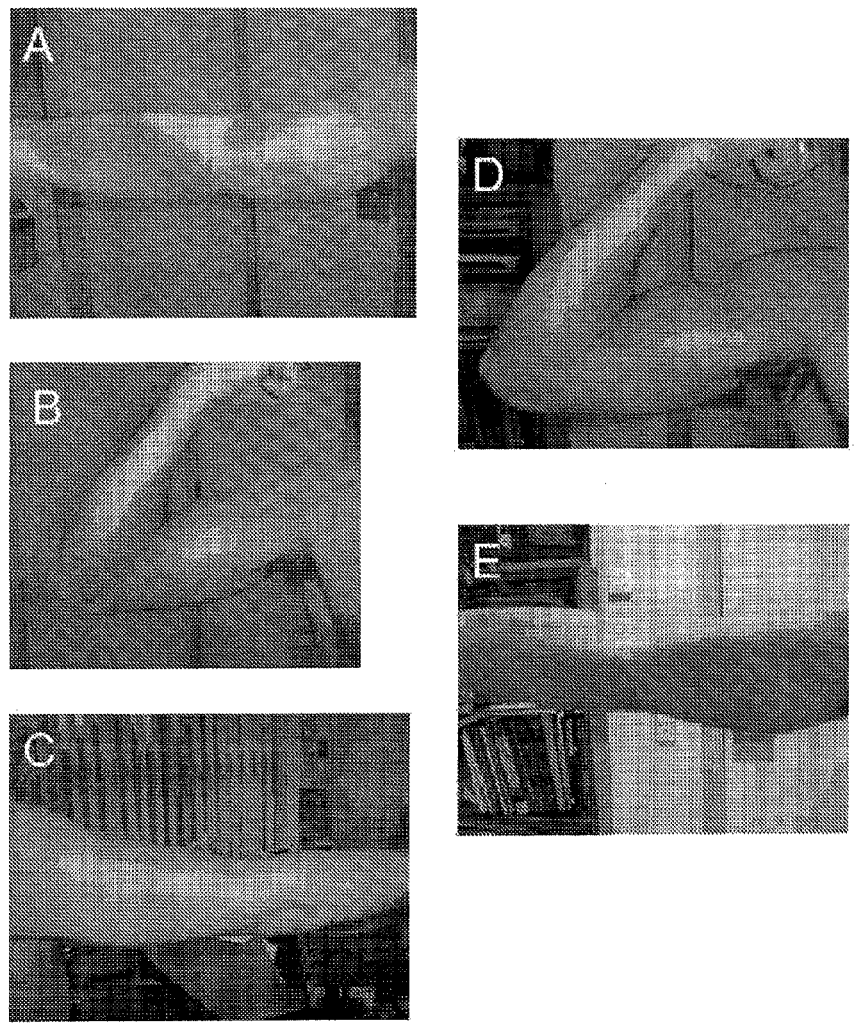

FIG. 13. Skeletal Muscle.

Images show the clinical manifestation of the patient referred to in FIG. 12. Before the treatment (1 day after the lesion) a large hematoma (A) and limited flexion (B) and extension (C) of the elbow are observed. After 20 days of oral treatment with 2,5-dihydroxybenzene sulfonic acid (DHBS) (1500 mg/day) the hematoma has disappeared and the flexion (D) and extension (E) capacity of the elbow have been recovered.

Figure 14:
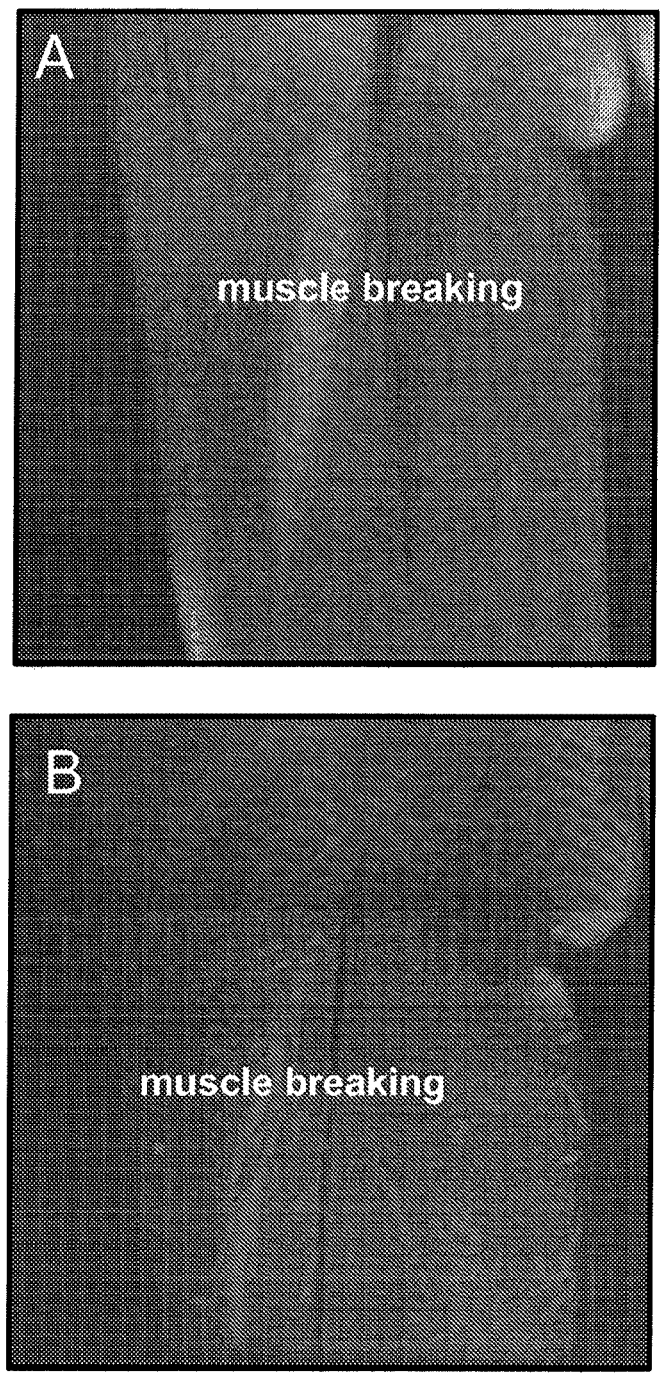

FIG. 14. Skeletal Muscle.

It is a Magnetic Resonance Image (MRI) of a patient showing the breaking of left leg semitendinosus muscle 9 days after the lesion and immediately before starting the treatment. B is the MRI of the same patient after being treated with 2,5-dihydroxybenzene sulfonic acid (DHBS) (1500 mg/day p.o. for 11 days) A remarkable reduction in the size of the lesion may be observed.

Figure 15:
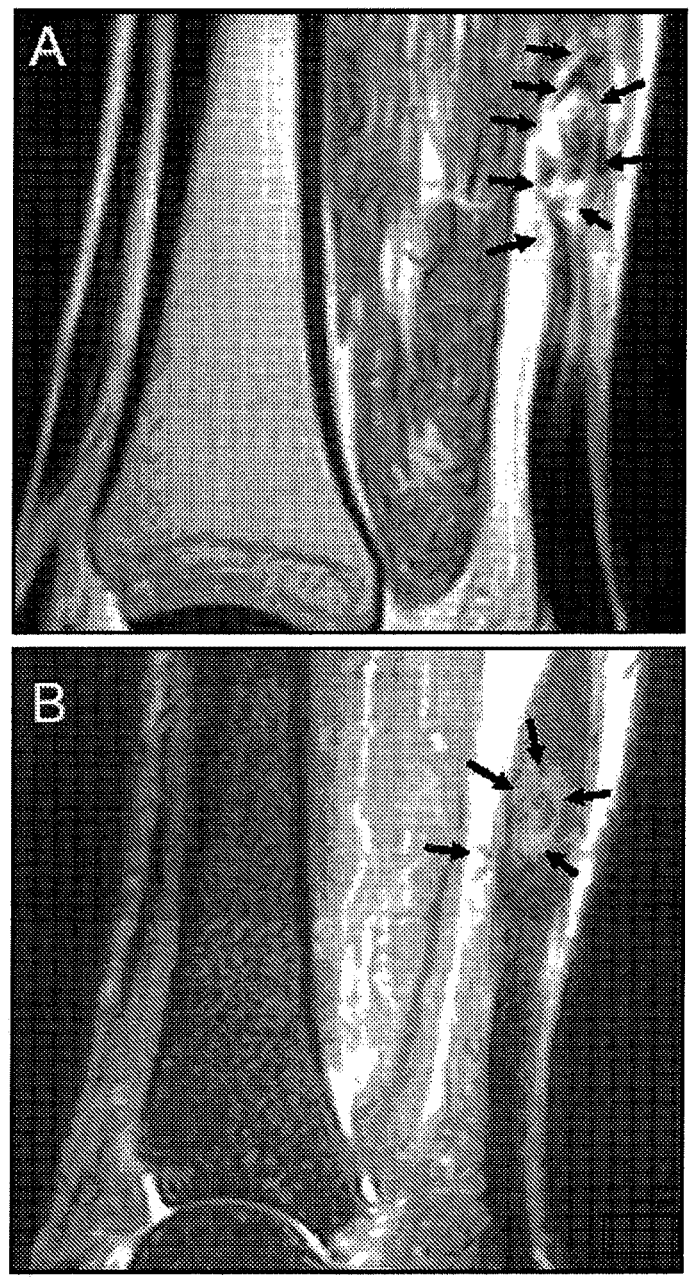

FIG. 15. Skeletal Muscle.

A is a Magnetic Resonance Image (MRI) of a patient showing the Achilles tendon rupture just before being treated. B is the MRI of the same patient after being treated with 2,5-dihydroxybenzene sulfonic acid (DHBS) (1500 mg/day p.o. for 2 months) A remarkable reduction in the size of the lesion may be observed (marked with arrows in both images).

Figure 16:
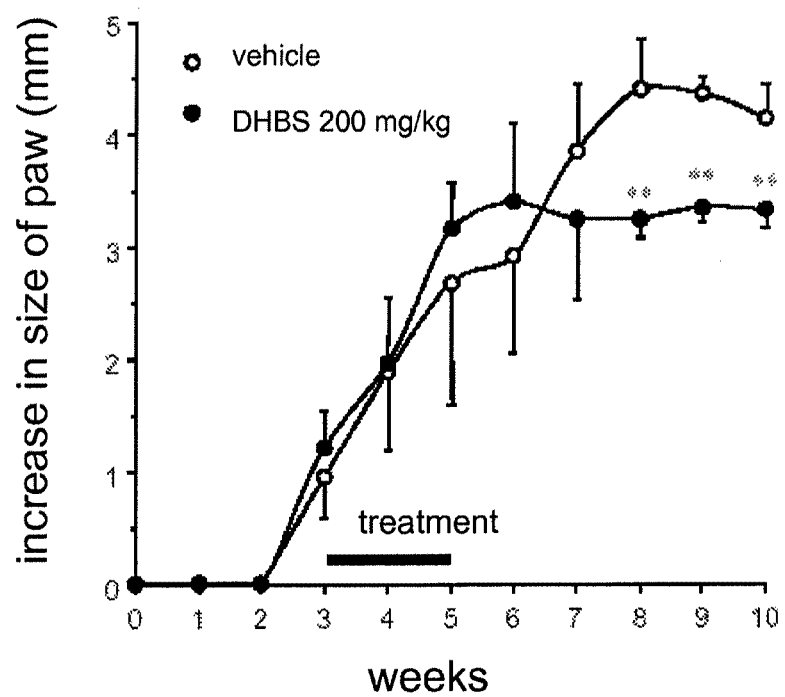

FIG. 16. Leishmaniasis.

Reduction in the size of the lesion caused by massive inoculation of *Leishmania major* promastigotes in the plantar pad of the back paw of BALB/c female mice after the daily intraperitoneal treatment with potassium 2,5-dihydroxybenzenesulfonate (DHBS, 200 mg/kg) for 14 days from the third week after infection. The vehicle group consisted of infected animals that received daily injections of saline (0.9% NaCl) during the same period as DHBS. Results are expressed as the mean±the standard deviation of the increases in size of the inoculated paw (right) compared to the non-inoculated paw (left) in mm obtained with a Vernier caliper each week from 0 to 10. ** indicates p<0.01 vs. the vehicle-treated group by a Student t-test. 6 animals were used for each group.

Figure 17:
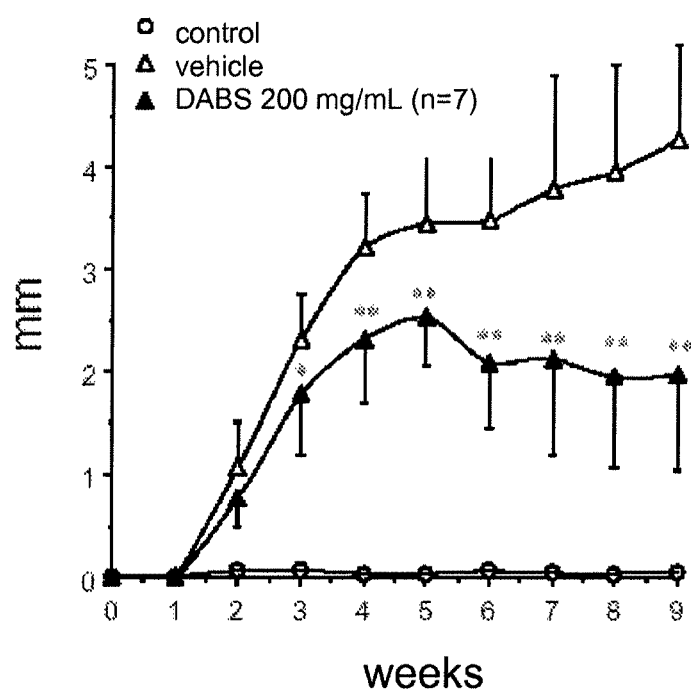

FIG. 17. Leishmaniasis.

Reduction in the size of the lesion caused by massive inoculation of *Leishmania major* promastigotes in the plantar pad of the back paw of BALB/c female mice after the daily intraperitoneal treatment with potassium 2,5-diacetoxybenzenesulfonate (DABS, 200 mg/kg) from the moment of the infection. The vehicle group consisted of infected animals that received daily injections of saline (0.9% NaCl) from the moment of the infection, while the control group consisted of non-infected animals. Results are expressed as the mean±the standard deviation of the increases in size of the inoculated paw (right) compared to the non-inoculated paw (left) in mm obtained with a Vernier caliper each week from 0 to 9. * indicates p<0.05 vs. the vehicle group by a Student t-test. 7 animals were used for each group.

Figure 18:
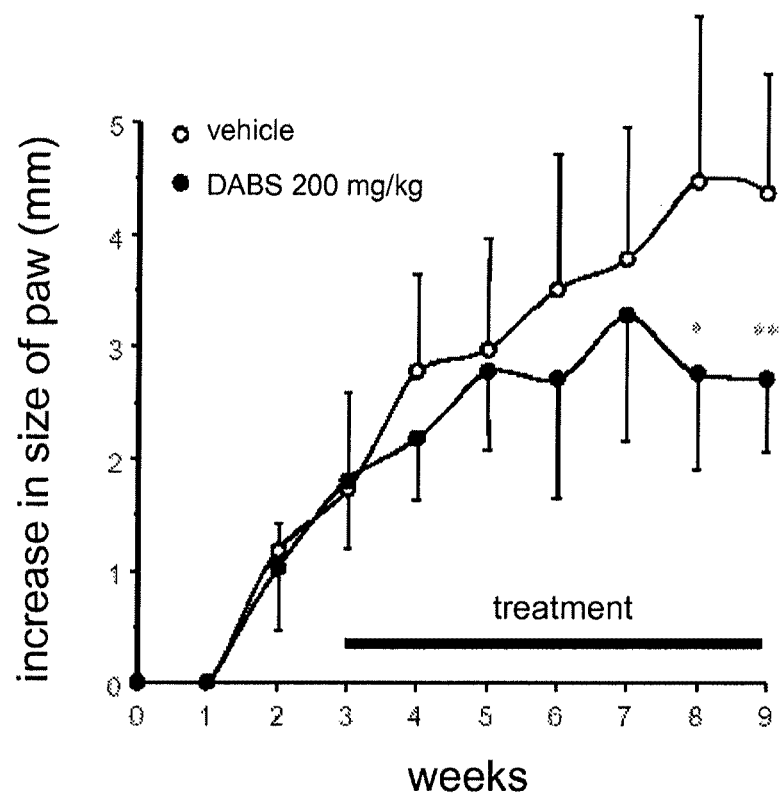

FIG. 18. Leishmaniasis.

Reduction in the size of the lesion caused by massive inoculation of *Leishmania major* promastigotes in the plantar pad of the back paw of BALB/c female mouse after the daily intreperitoneal treatment with potassium 2,5-diacetoxybenzenesulfonate (DABS, 200 mg/kg) from the third week after the infection. The vehicle group consisted of infected animals that received daily injections of saline (0.9% NaCl) from the third week after the infection. Results are expressed as the mean±the standard deviation of the increases in size of the inoculated paw (right) compared to the non-inoculated paw (left) in mm obtained with a Vernier caliper each week from 0 to 9. * indicates p<0.05 vs. the vehicle group by a Student t-test. 7 animals were used for each group.

Figure 19:
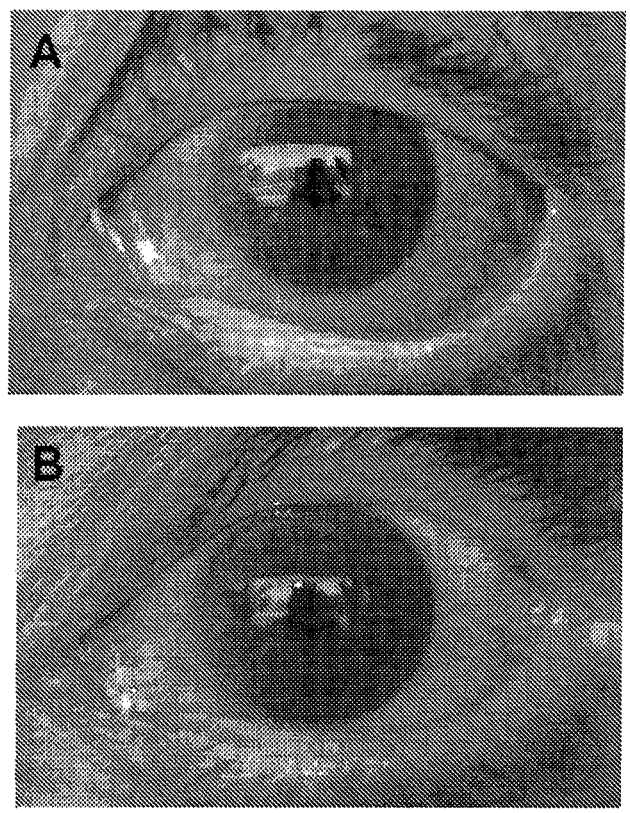

FIG. 19. Corneal Neovascularization.

The application of 2,5-dihydroxybenzoic acid (gentisic acid) for 19 days produced a noticeable reduction in the degree of corneal vascularization. Photographs showing the presence of corneal neovascularization in a patient before being treated (A) and after 19 days of topical application of a solution containing 5% of potassium 2,5-dihydroxybenzoate (B). The treatment consisted of daily topical application of 4 drops of such solution.

Figure 20:
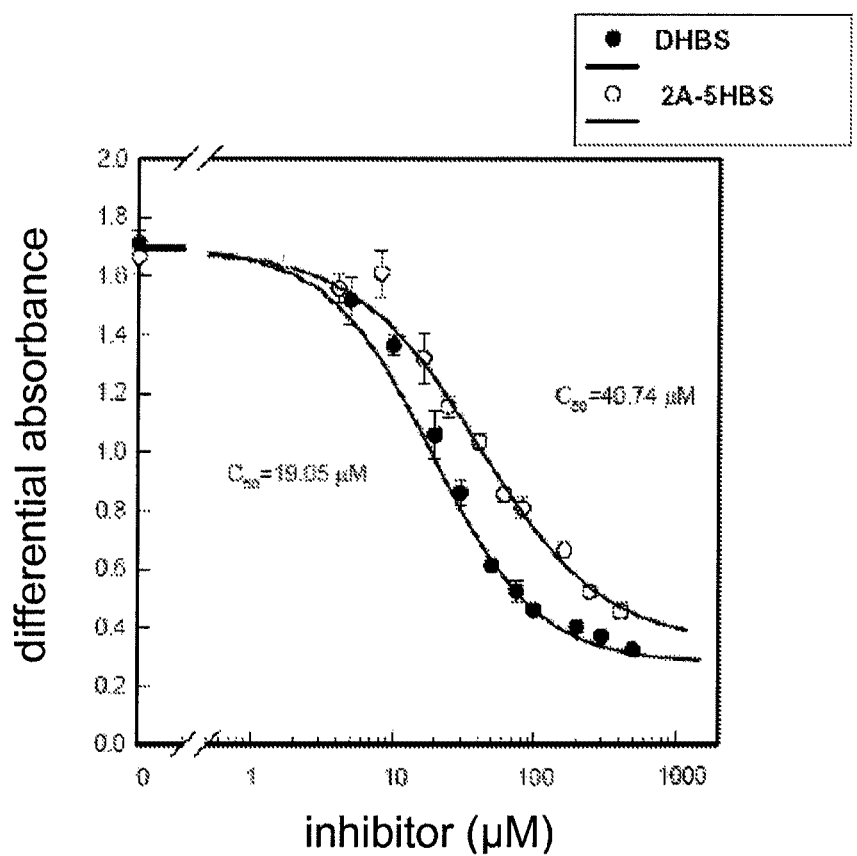

FIG. 20. Inhibition of the mitogenesis induced by fibroblast growth factor-1 in Balb/c 3T3 fibroblasts quiescent cultures by calcium 2-acetoxy-5-hydroxybenzenesulfonate (2A-5HBS) and potassium 2,5-dihydroxybenzenesulfonate (DHBS).

Figure 21:
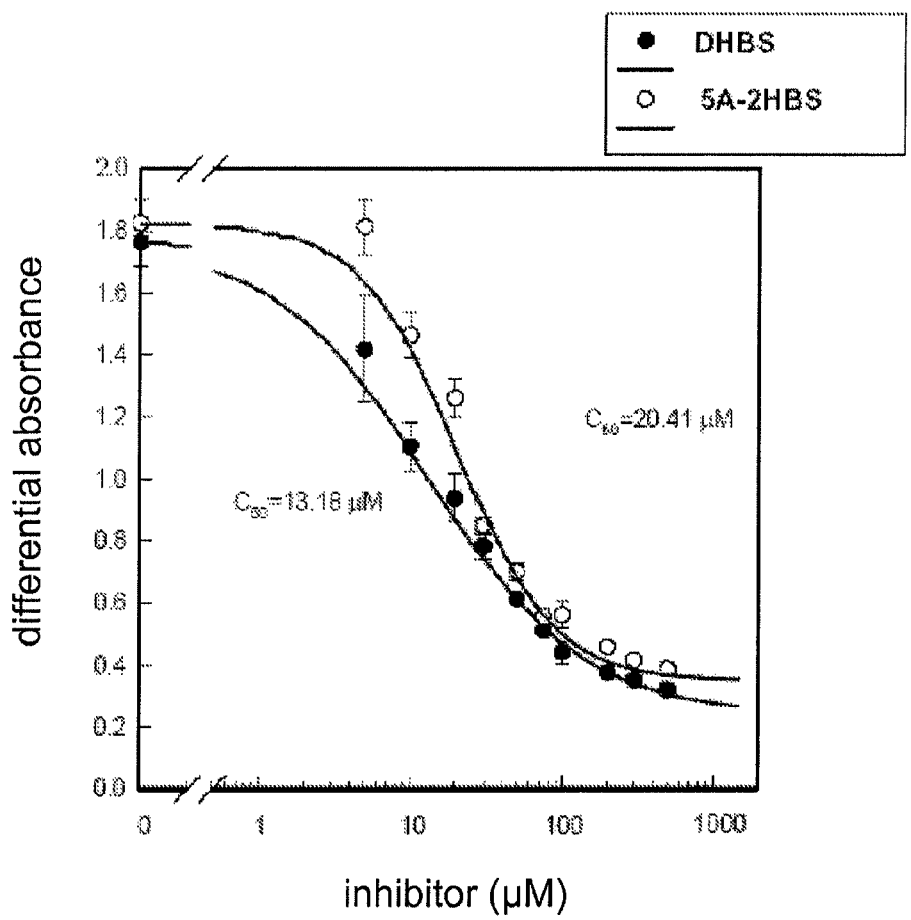

FIG. 21. Inhibition of the mitogenesis induced by fibroblast growth factor-1 in Balb/c 3T3 fibroblasts quiescent cultures by potassium 5-acetoxy-2-hydroxybenzenesulfonate (5A-2HBS) and potassium 2,5-dihydroxybenzenesulfonate (DHBS).

Figure 22:
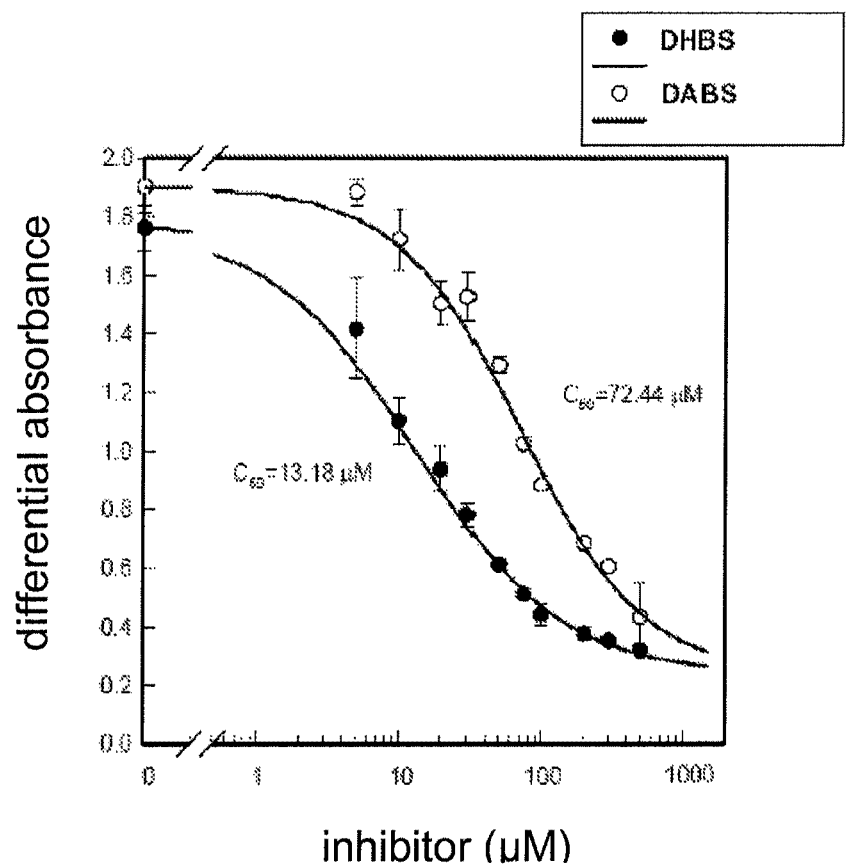

FIG. 22. Inhibition of the mitogenesis induced by fibroblast growth factor-1 in Balb/c 3T3 fibroblasts quiescent cultures by potassium 2,5-diacetoxybenzene sulfonate (DABS) and potassium 2,5-dihydroxybenzene sulfonate (DHBS).

Figure 23:
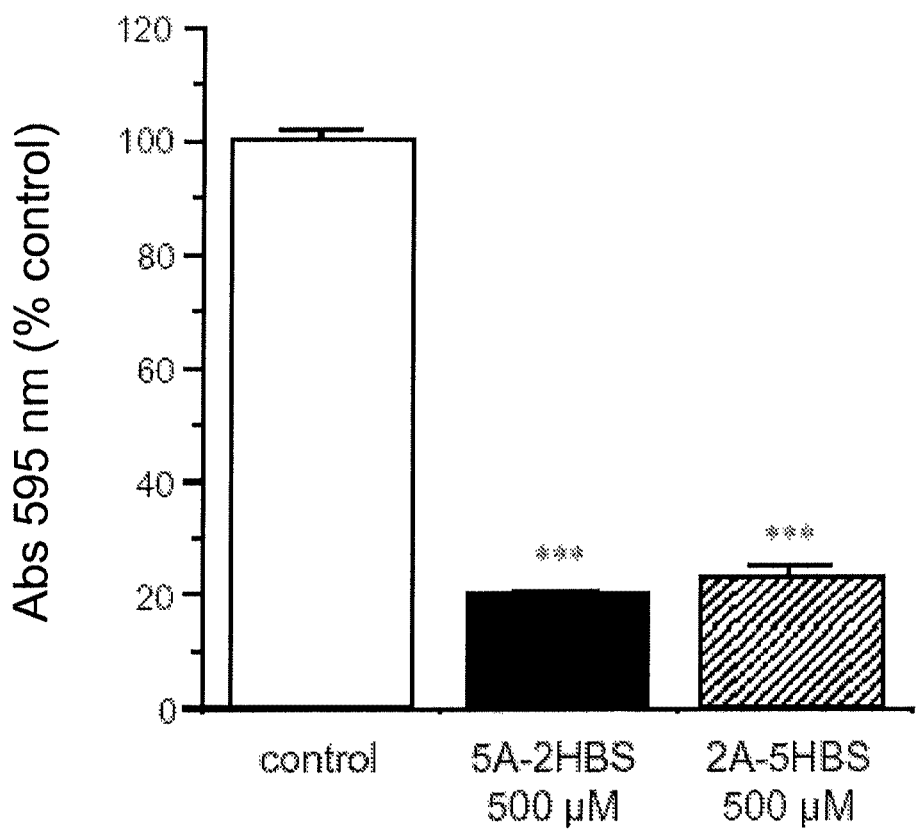

FIG. 23. Shows the effect of the treatment with potassium 5-acetoxy-2-hydroxybenzenesulfonate (5A-2HBS) and the potassium 2-acetoxy-5-hydroxybenzenesulfonate (2A-5HBS) on the proliferation of rat C6 glioma cells. 5A-2HBS and 2A-5HBS were administered or not (control) after seeding C6 cells in 24 well plates ($10^4$ per well) until they were fixed 48 hours later. Data are expressed as the mean±SEM of the percentage of absorbance at 595 nm obtained in control cultures, which is proportional to the number of cells stained with crystal violet. Data were obtained from 3 cultures for each treatment and 6 control cultures. The white bar represents the value of the control cells, whereas the black bar shows the value in presence of 5A-2HBS (500 µM), and the striped bar shows the value in the presence of 2A-5HBS (500 µM). *** indicates p<0.001 with respect to control by a one-factor analysis of variance (ANOVA) followed by a Student-Newmann-Keuls post-analysis.

Figure 24:
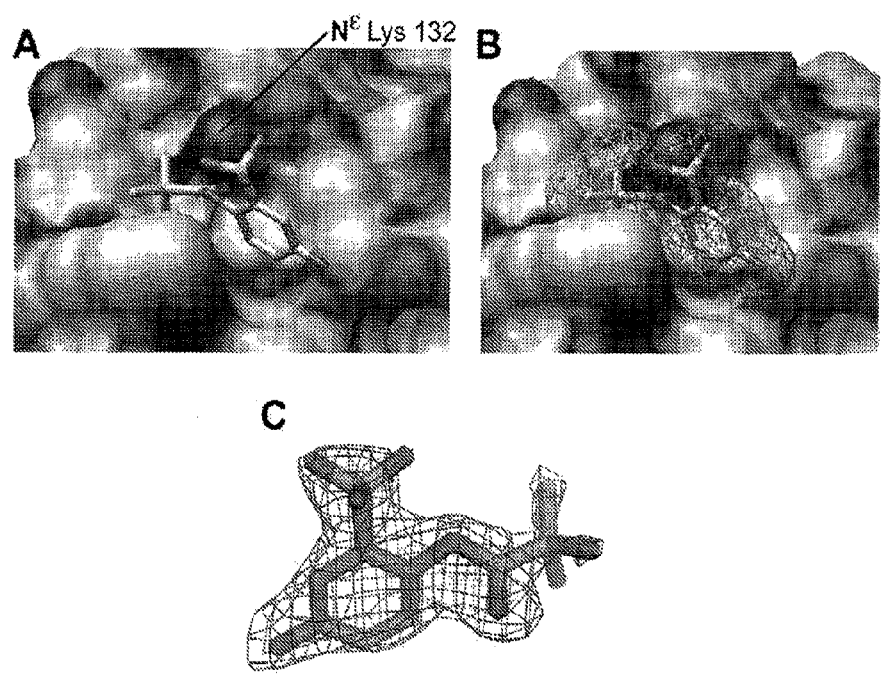

FIG. 24. 2-acetoxy-5-hydroxybenzenesulfonic acid co-crystallized with fibroblast growth factor-1. The electronic density of the compound, contoured at 1σ (panel C), allows locating and determining the orientation of the compound with respect to the protein (panels A and B), as well as asserting that the compound conserves the acetoxyl group in position 2 when it binds to the protein. The compound occupies a place that is very close to that described occupied by 2,5-dihydroxybenzenesulfonic acid, the aromatic ring of which forms a cation-σ bond with the $N^\epsilon$ group of lysine 132, which is marked in panel A as reference. Panel B shows, in the form of a mesh, the Van der Waals volume of 2-acetoxy-5-hydroxybenzenesulfonic acid, superimposed with its representation in the form of rods. In panels A and B, the protein surface is colored according to its electrostatic potential (light grey: negative charge; dark grey: positive charge; white: lack of charge).

Figure 25:
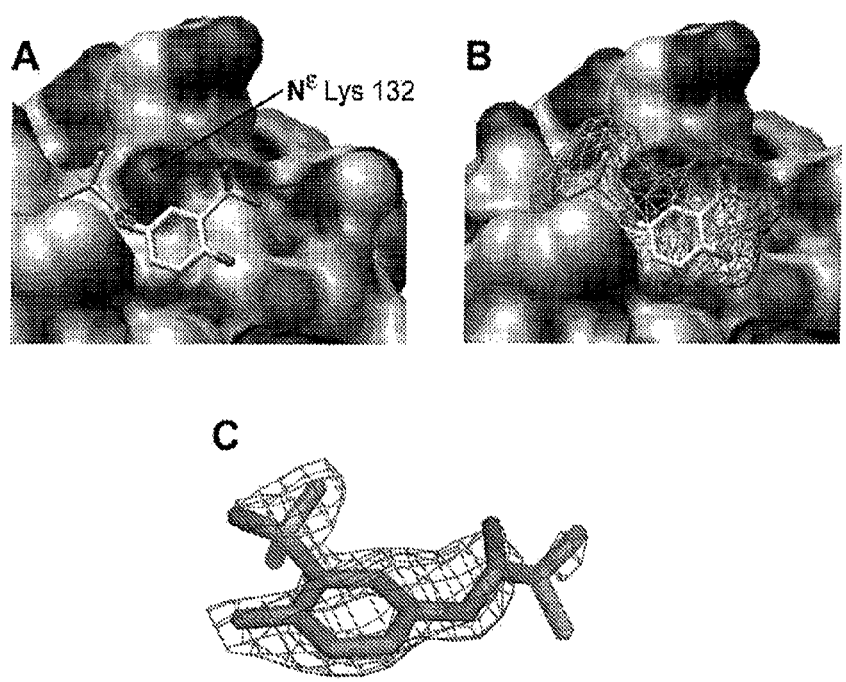

FIG. 25. 5-acetoxy-2-hydroxybenzenesulfonic acid co-crystallized with fibroblast growth factor-1. The electronic density of the compound, contoured at 1σ (panel C), allows locating and determining the orientation of the compound with respect to the protein (panels A and B), as well as asserting that the compound conserves the acetoxyl group in position 5 when it binds to the protein. The compound occupies a place that is very close to that described occupied by 2,5-dihydroxybenzenesulfonic acid, the aromatic ring of which forms a cation-π bond with the $N^\epsilon$ group of lysine 132, which is marked in panel A as reference. Panel B shows, in the form of a mesh, the Van der Waals volume of 2-acetoxy-5-hydroxybenzenesulfonic acid, superimposed with its representation in the form of rods. In panels A and B, the protein surface is colored according to its electrostatic potential (light grey: negative charge; dark grey: positive charge; white: lack of charge).

Figure 26:
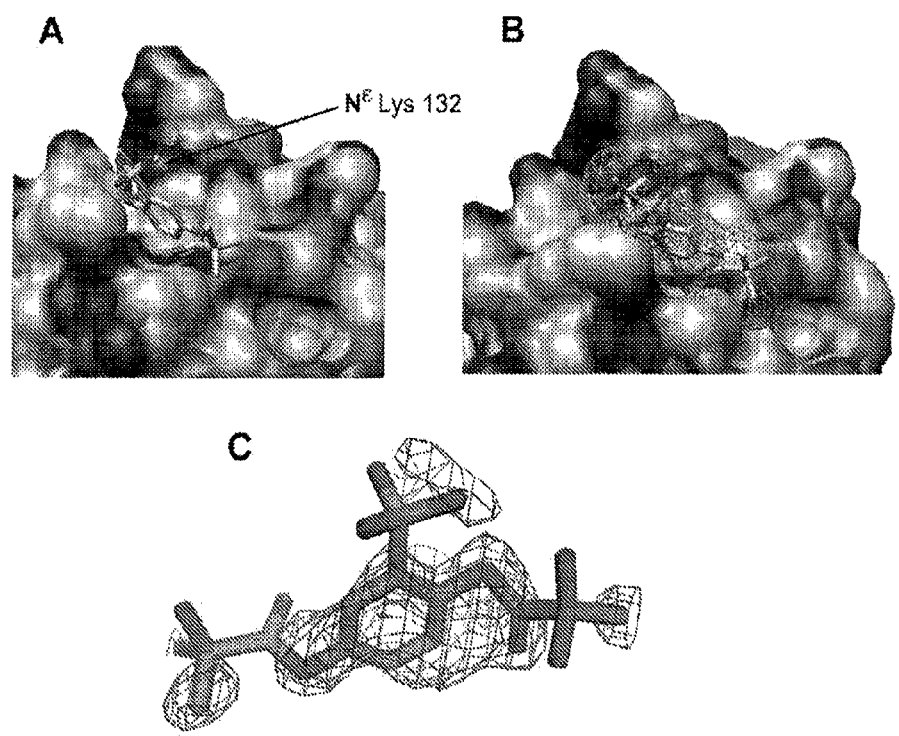

FIG. 26. 2,5-diacetoxybenzenesulfonic acid co-crystallized with fibroblast growth factor-1. The electronic density of the compound, contoured at $1\sigma$ (panel C), allows locating and determining the orientation of the compound with respect to the protein (panels A and B), as well as asserting that the compound conserves the acetoxyl groups in positions 2 and 5 when it binds to the protein. The compound occupies a place that is very close to that described occupied by 2,5-dihydroxybenzenesulfonic acid, the aromatic ring of which forms a cation-$\pi$ bond with the $N^\epsilon$ group of lysine 132, which is marked in panel A as reference. Panel B shows, in the form of a mesh, the Van der Waals volume of 2,5-diacetoxybenzenesulfonic acid, superimposed with its representation in the form of rods. In panels A and B, the protein surface is colored according to its electrostatic potential (light grey: negative charge; dark grey: positive charge; white: lack of charge).

Figure 27:
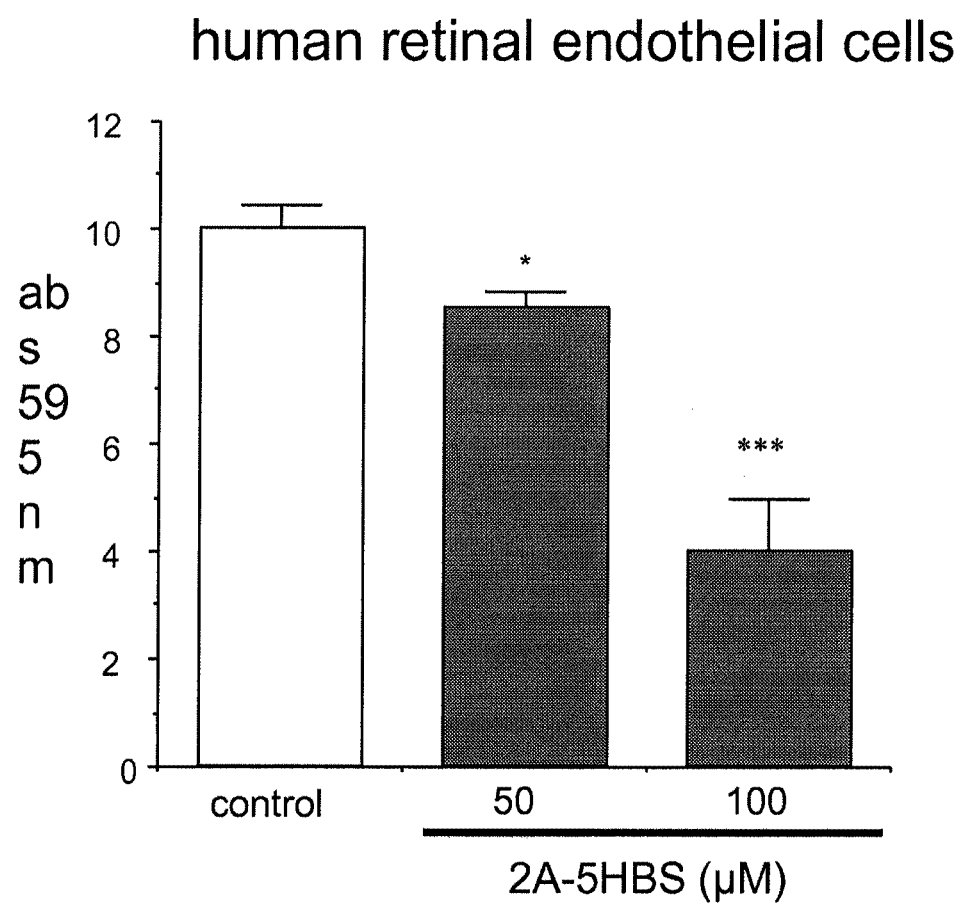

FIG. 27 shows the effect of the treatment with potassium 2-acetoxy-5-hydroxybenzene sulfonate (2-monoacetylated dobesilate; 2A-5HBS) on the proliferation of human endothelial retinal cells (HREC). 2A-5HBS was administered or not administered (control) after seeding the HREC in 24-well plates ($7.5 \times 10^3$ per well) until they were fixed after 72 hours. The data are expressed as the mean±SEM of the percentage of the absorbance at 595 nm obtained in the control cultures, which is proportional to the number of cells stained with crystal violet. The data were obtained from 6 cultures for each treatment in two separate experiments. The white bar represents the value of the control cells, whereas the gray bars show the value in the presence of 2A-5HBS (500 and 1000 μM). * indicates $p<0.05$, *** $p<0.001$ with respect to the control by means of a single-factor analysis of variance (ANOVA) followed by a Student-Newman-Keuls post-analysis.

Figure 28:
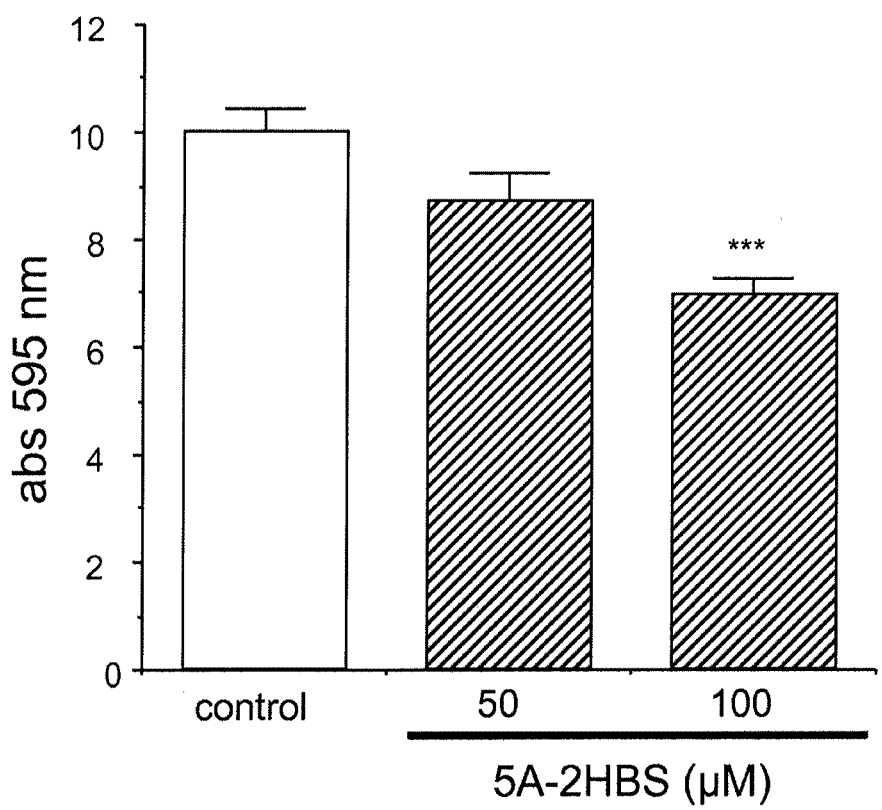

FIG. 28 shows the effect of the treatment with potassium 5-acetoxy-2-hydroxybenzene sulfonate (5-monoacetylated dobesilate; 5A-2HBS) on the proliferation of human endothelial retinal cells (HREC). 5A-2HBS was administered or not administered (control) after seeding the HREC in 24-well plates ($7.5 \times 10^3$ per well) until they were fixed after 72 hours. The data are expressed as the mean±SEM of the percentage of the absorbance at 595 nm obtained in the control cultures, which is proportional to the number of cells stained with crystal violet. The data were obtained from 6 cultures for each treatment in two separate experiments. The white bar represents the value of the control cells, whereas the striped bars show the value in the presence of 5A-2HBS (500 and 1000 μM). *** indicates $p<0.001$ with respect to the control by means of a single-factor analysis of variance (ANOVA) followed by a Student-Newman-Keuls post-analysis.

Figure 29:
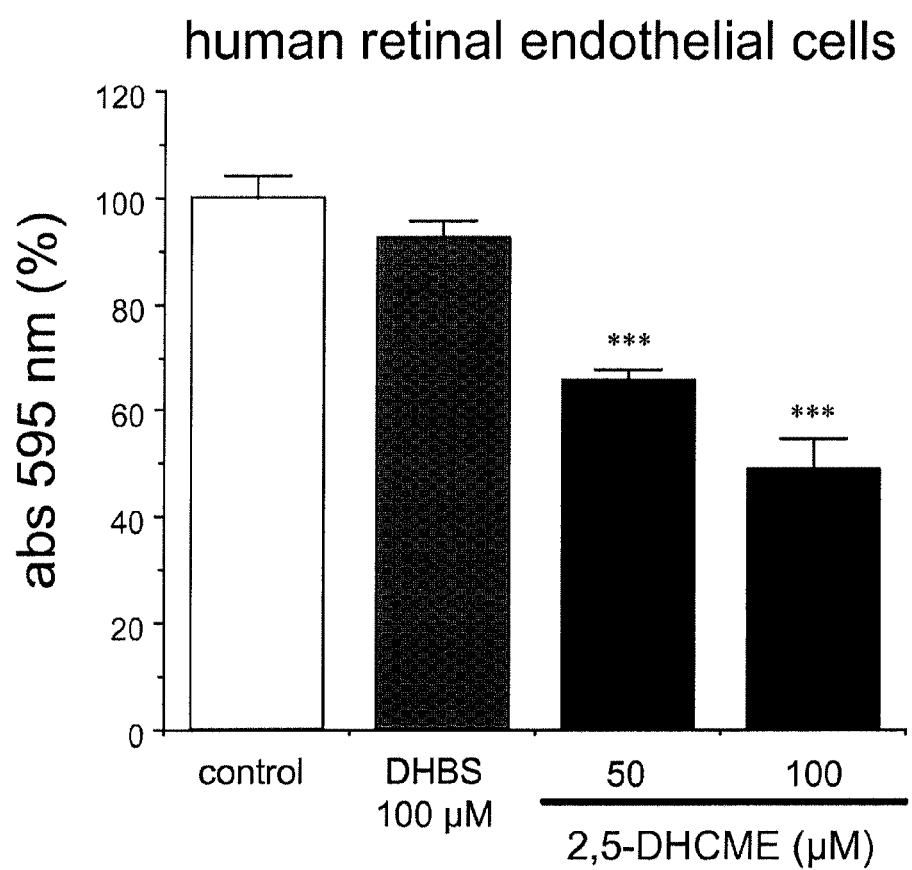

FIG. 29 shows the effect of the treatment with 2,5-dihydroxycinnamic acid methyl ester (2,5-DHCME) and calcium 2,5-dihydroxybenzenesulfonate (DHBS) on the proliferation of human endothelial retinal cells (HREC). 2,5-DHCME was administered or not administered (control) after seeding the HREC in 24-well plates ($7.5 \times 10^3$ per well) until they were fixed after 72 hours. The data are expressed as the mean±SEM of the percentage of the absorbance at 595 nm obtained in the control cultures, which is proportional to the number of cells stained with crystal violet. The data were obtained from 6 cultures for each treatment in two separate experiments. The white bar represents the value of the control cells, whereas the chequered bar shows the value in the presence of DHBS (100 μM) and the black bars show the value in the presence of 2,5-DHCME (50 and 100 μM). *** indicates $p<0.001$ with respect to the control by means of a single-factor analysis of variance (ANOVA) followed by a Student-Newman-Keuls post-analysis.

DETAILED DESCRIPTION OF THE INVENTION

As used in the description, it must be understood that, unless otherwise specified, the following terms shall have the meanings set forth below:

The term "patient" refers to animals, preferably mammals, and more preferably humans, and includes males and females, children and adults.

The expression "effective amount" refers to the amount of the compound and/or composition effective to achieve the desired purpose.

The terms "treat" or "treatment" refer to the use of the compounds or compositions of the present invention, prophylactically to avoid the symptoms of the disease or disorder, or therapeutically to improve an existing condition.

The term "therapeutic agent" includes any active agent that can be used to treat or prevent a disease described herein. "Therapeutic agents" include but are not limited to corticosteroids, antibiotics, analgesics, alpha-adrenergic blockers, beta-adrenergic agonists, anticholinergics, inhibitors of 5-alpha-reductase, antiandrogens, oral contraceptives, immunomodulators, immunosuppressants, anti-angiogenics, bronchodilators, leukotriene modifiers, aminosalicylates, anesthetics, non-steroidal anti-inflammatories, antiparasitics, antioxidants, proton pump inhibitors, H2-receptor antagonists, therapy of the solubilized interleukin receptor, intramuscular gold, cytotoxics, chemotherapy agents, and combinations of two or more thereof.

A therapeutic agent includes pharmaceutically acceptable salts thereof, prodrugs and pharmaceutical derivatives thereof.

The term "hemangioma" refers to a vascular tumor that appears during childhood.

The term "hemangioblastoma" refers to another vascular tumor that appears during childhood.

The term "pterygium" refers to a corneal disease.

The term "endometriosis" refers to the growth of endometrial tissue outside the uterus.

The term "prostate benign hyperplasia" refers to a disease in which the prostate gland increases considerably and may cause micturition-related alterations.

The term "*Helicobacter pylori*" refers to a bacteria that produces gastrointestinal symptoms.

The term "Barrett's disease" refers to a metaplasia/dysplasia process of the esophagic epithelium.

The term "ulcerative colitis (proctitis, proctosigmoiditis, pancolitis)" refers to a disease that causes ulcers in the rectum and colon producing bleeding and diarrhea.

The term "Crohn's disease" refers to an autoimmune chronic disease producing intestinal inflammation. Even if it may affect the whole gastrointestinal tract, most frequently it affects the ileum.

The term "pain" refers to an unpleasant emotional (subjective) and sensorial (objective) experience associated to an injury.

The term "asthma" refers to a chronic disease that affects the airways, constricting them.

The term "arthritis" refers to a condition, usually chronic, that causes stiffness, pain and sometimes joint swelling; it includes osteoarthritis, rheumatoid arthritis, polyarthritis, gouty arthritis, lupus-related arthritis, psoriasis-related arthritis, and the like).

The term "skeletal muscle diseases" refers to lesions thereof, like breakings and traumas.

The term "ovarian hyperstimulation syndrome" refers to a complication of fertility treatments characterized by a severe inflammatory reaction and an increase of vascular permeability.

The term "polycystic kidney disease" refers to a hereditary disease that affects the kidney and predisposes the need of a renal transplant.

The term "leishmaniasis" refers to the parastitation by species of *Leishmania* genus in human and pets that causes a disease affecting the skin, mucosa o visceras.

The term "corneal and retinal neo-vascularization" refers to the formation of new blood vessels invading the cornea or that appear in the retine and that may cause visual impairment and blindness. For example, diabetic retinopathy.

The term "topical" refers to the administration of a compound by applying it on the body surface and includes, but is not limited to, the transdermal administration and the administration through the mucosa.

The term "transdermal" refers to the administration of a compound that enters into the bloodstream through the skin.

The expression "through the mucosa" refers to the administration of a compound that enters into the bloodstream through the mucous tissue.

The term "parenteral" refers to the administration of a compound by means of a subcutaneous, intravenous, intramuscular, intracardiac, intradermic, intraperitoneal, intrathecal or intrasternal injection; and also includes local or systemic infusion techniques.

The expression "penetration enhancement" or "permeation enhancement" refers to an increase in the permeability of the skin or mucous tissue to a pharmacologically active compound such that it increases the rate and/or amount of said compound that penetrates into, or through the skin or mucous tissue.

"Excipients" or "vehicles" refers to the vehicle materials suitable for compound administration and include any such material known in the art such as, for example, any liquid, gel, solvent, liquid diluent, solubilizer, or the like, which is non-toxic and which does not interact harmfully with any component of the composition.

The expression "sustained release" refers to the release of an active compound and/or composition such that the blood levels of the active compound are maintained within a desirable therapeutic range over a period of time. The sustained release formulation may be prepared using any conventional known method by a skilled in the art in order to obtain the desired release characteristics.

The term "ester derivative of a compound of formula (I)" refers to the compound of formula (I) wherein at least one of $R_9$ and $R_{9'}$ is an ester group. For example, the ester derivative of 2,5-dihydroxybenzene sulfonic acid or dobesilate ester derivative refers to the compound 2,5-dihydroxybenzene sulfonic acid (dobesilate) wherein at least one of the hydroxyl groups has been esterified.

The term "ester of a compound of formula (I)" refers to an ester of the sulfonic or carboxylic acid group at position 1. For example, the ester of 2,5-dihydroxybenzensulfonic acid or ester of dobesilate refers to an ester of the sulfonic acid group at position 1.

In the definitions of the compounds described herein, the following terms mean:

"Alkyl" means a linear or branched chain hydrocarbon radical comprising carbon atoms and hydrogen, with no unsaturations, with one to twelve, preferably one to eight, more preferably one to six carbon atoms, bound to the rest of the molecule by a single bond, for example, methyl, ethyl, n-propyl, i-propyl, n-butyl, t-butyl, n-pentyl, etc.

"Alkenyl" refers to a linear or branched chain hydrocarbon radical comprising carbon atoms and hydrogen atoms, containing at least one unsaturation, with two to twelve, preferably two to eight, more preferably two to six carbon atoms, bound to the rest of the molecule by a single bond.

"Cycloalkyl" refers to a saturated carbocyclic ring having between three and eight, preferably three to six carbon atoms. They may exhibit a bridged structure. Suitable cycloalkyl groups include, but are not limited to, cycloalkyl groups such as cyclopropyl, cyclobutyl, cyclopentyl or cyclohexyl.

"Aryl" refers to an aromatic hydrocarbon radical containing from six to ten carbon atoms such as phenyl or naphthyl.

"Aralkyl" refers to an aryl group bound to the rest of the molecule by an alkyl group such as benzyl and phenetyl.

"Heterocycle" refers to a stable 3 to 15-membered ring comprised of carbon atoms and between one and five heteroatoms selected from the group consisting of nitrogen, oxygen and sulfur, preferably a 4 to 8-membered ring with one, two, three or four heteroatoms, more preferably a 5 or 6-membered ring with one, two or three heteroatoms. For the purpose of the present invention, the heterocycle may be a monocyclic, bicyclic or tricyclic ring system that may include fused ring systems; bridged structures; and the nitrogen, carbon or sulfur atoms in the heterocyclic radical may be optionally oxidized; the nitrogen atom may be optionally quaternized; and the heterocyclic radical may be partially or completely saturated or it may be aromatic. Examples of such heterocycles include, but are not limited to, azepines, benzimidazole, benzothiazole, furan, isothiazole, imidazole, indole, piperidine, piperazine, purine, quinoline, thiadiazol, tetrahydrofuran.

Unless otherwise specified, the alkyl, cycloalkyl, alkenyl, alkynyl, aryl, aralkyl and heterocycle radicals may be optionally substituted by one, two or three substituents such as halo, alkyl, alkenyl, alkynyl, cycloalkyl, hydroxy, alkoxy, sulfoxy, O-Benzyl, O-Benzoyl, carboxyl, alkylcarboxyl, arylcarboxyl, alkylcarbonyl, arylcarbonyl, cyano, carbonyl, acyl, alkoxycarbonyl, amino, alkylamino, dialkylamino, arylamino, diarylamino, alkylarylamino, imino, alkylsulphinyl, amidyl, carbamoyl, sulfonamido, nitro, nitrite, nitrate, thionitrate and carboxamido.

The term "alkoxycarbonyl" refers to a compound having the formula —C(=O)O—, wherein the C-terminal is bound to the molecule and the O-terminal is bound to a carbon atom to form an ester function. Said carbon atom may be part of an alkyl, alkenyl, cycloalkyl, alkynyl, aryl, aralkyl or heterocyclic group.

The term "alkoxycarbonylalkyl" refers to a compound of the previously defined formula —C(=O)O—, wherein the C-terminal binds to a molecule through an alkyl group. The terms "aryloxy- arylalkoxy- or alkylaryloxy-carbonylalkyl" will be understood similarly to "alkoxycarbonylalkyl".

The term "arylalkyl" refers to an aryl radical, as defined herein, bound to an alkyl radical, as defined herein. The exemplary arylalkyl groups include benzyl, phenylethyl, 4-hydroxybenzyl, 3-fluorobenzyl, 2-fluorophenylethyl and the like.

The term "alkylaryl" refers to an alkyl group, as defined herein, to which an aryl group is bound, as defined herein. The exemplary alkylaryl groups include benzyl, phenylethyl, hydroxybenzyl, fluorobenzyl, fluorophenylethyl, and the like.

The term "alkylsulfonyl" refers to a $R_{50}$—S(O)$_2$—, wherein $R_{50}$ is a lower alkyl group, as defined herein.

The term "arylsulfonyl" refers to $R_{55}$—S(O)$_2$—, wherein $R_{55}$ is an aryl group, as defined herein.

The term "alkylsulphinyl" refers to $R_{55}$—S(O)—, wherein $R_{55}$ is an aryl group, as defined herein.

The term "arylsulphinyl" refers to $R_{55}$—S(O)—, wherein $R_{55}$ is an aryl group, as defined herein.

The term "sulfonamide" refers to —S(O)$_2$—N($R_{51}$)($R_{57}$), wherein $R_{51}$ and $R_{57}$ are each independently a hydrogen atom, an alkyl group, an aryl group, heterocycle, as defined herein, or else $R_{51}$ and $R_{57}$ together form a heterocyclic ring, a cycloalkyl group or a bridged cycloalkyl group, as defined herein.

The term "alkylsulfonamido" refers to a sulfonamido group, as defined herein, bound to an alkyl group, as defined herein.

The term "arylsulfonamido" refers to a sulfonamido group, as defined herein, bound to an aryl group, as defined herein.

The term "alkylcarbonyl" refers to $R_{52}$—C(O)$_2$—, wherein $R_{52}$ is an alkyl group, as defined herein.

The term "arylcarbonyl" refers to the $R_{55}$—S(O)— radical, wherein $R_{55}$ is an aryl group, as defined herein.

The term "carboxamide" refers to the —C(O)N($R_{52}$)($R_{58}$) radical, wherein $R_{52}$ and $R_{58}$ are each independently a hydrogen atom, an alkyl group, an aryl group or an heterocyclic group, as defined herein, or else $R_{51}$ and $R_{57}$ together form an heterocyclic ring, a cycloalkyl group, or a bridged cycloalkyl group, as defined herein.

The term "carboxylic ester" refers to —C(O)OR$_{59}$, wherein $R_{59}$ is an alkyl group an aryl group or an heterocyclic group, as defined herein.

The term "alcoxyalkyl" refers to an alcoxy group, as defined herein, bound to an alkyl group, as defined herein. Examples of alcoxyalkyl groups are methoxymethyl, methoxyethyl, isopropoximethyl and the like.

The term "amine" refers to any organic compound containing at least one basic nitrogen atom.

The term "organic cation" refers to a positively charged organic ion. The exemplary organic cations include ammonium cations unsubstituted or substituted with alkyl, primary, secondary o tertiary amines, alkylamines, arylamines, cyclic amines, N,N'-dibenzylethylenediamine, and the like.

The term "inorganic cation" refers to a positively charged metal ion. The exemplary inorganic cations include Group I metal cations such as sodium, potassium, magnesium, calcium and the like.

The term "prodrug" refers to compounds that rapidly convert in vivo into pharmacologically active compounds. Prodrug design is generally studied in Hardma et al. (eds.), Goodman and Gilman's The Pharmacological Basis of Therapeutics, 9th ed., pages 11-16 (1996). A detailed study is disclosed in Higuchi et al., Prodrugs as Novel Delivery Systems, vol. 14, ASCD Symposium Series, y en Roche (ed.), Bioreversible Carriers in Drug Design, American Pharmaceutical Association and Pergamon Press (1987).

The compounds of the invention having one or more asymmetric carbon atoms may exist as optically pure enantiomers, pure diastereomers, mixtures of enantiomers, mixtures of diastereomers, racemic mixtures of enantiomers, diastereomeric racemates or mixtures of diastereomeric racemates. It should be clearly understood that the invention contemplates and includes these isomers and mixtures thereof within its scope.

According to a first aspect, the present invention refers to the use of a compound of Formula (I) or pharmaceutically acceptable salt or solvate, isomers or prodrugs thereof in the manufacturing of a medicament for the treatment and/or prophylaxis of hemangiomas or hemangioblastomas, where the compound of Formula (I):

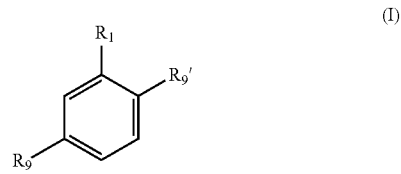

wherein:
$R_1$ is —(CH$_2$)$_a$Y or —CH=CH—(CH$_2$)$_p$Y;
Y is —SO$_3$H, —SO$_3^-$.X$^+$, —SO$_3$R$_3$, —PO$_3$H, —PO$_3$—.X$^+$, —PO$_3$R$_3$, —CO$_2$H, —CO$_2^-$.X$^+$ or —CO$_2$R$_3$;
X$^+$ is an organic cation or an inorganic cation, such that the general charge of the compound is neutral;
$R_9$ and $R_{9'}$ are individually selected from —OH and —OR$_2$; wherein when $R_9$ and $R_{9'}$ are both —OR$_2$, then said $R_9$ and $R_{9'}$, can be the same or different;
$R_2$ is a substituted or unsubstituted alkyl group, a substituted or unsubstituted aryl group, a substituted or unsubstituted arylalkyl group, a substituted or unsubstituted alkylsulfonyl group, a substituted or unsubstituted arylsulfonyl group, a substituted or unsubstituted alkylarylsulfonyl group, a substituted or unsubstituted arylalkysulfonyl group, a substituted or unsubstituted aryloxyalkyl group, a substituted or unsubstituted alkylcarbonyl group or an arylcarbonyl group, a carboxyl group, a substituted or unsubstituted alkoxycarbonyl group, a substituted or unsubstituted carboxyalkyl group, in particular —CH$_2$—COOH, or a substituted or unsubstituted alkoxy- aryloxy- arylalkoxy- or alkylaryloxy-carbonylalkyl, in particular —CH$_2$—COOR$_3$;
$R_3$ is a lower alkyl group, an aryl group, an arylalkyl group or an alkylaryl group;
a is number selected from 0, 1, 2, 3, 4, 5 and 6;
p is an integer selected from 0, 1, 2, 3, 4, 5 and 6.

In a particular embodiment, 2,5-dihydroxybenzene derivatives of the invention or any of the pharmaceutically acceptable salts thereof are those that are represented by Formula (I) comprising dobesilate esters derivatives or pharmaceutically acceptable salts or esters thereof for the treatment of hemangiomas or hemangioblastomas.

The X$^+$ cation in the Compounds of Formula (I) may be any physiologically acceptable cation known by a skilled in the art and includes, but is not limited to, those described in Heinrich Stahl, Camille G. Wermuth (eds.), "Handbook of Pharmaceutical Salts Properties, Selections and Use", Verlag Helvetica Chimica Acta, Zurich, Switzerland, Wiley-VCH, Weinheim, Germany, 2002; the disclosures of which are incorporated herein by reference in their entirety. The X$^+$ cation is selected in such a way that the total charge of the compounds of Formula (I) is neutral.

In a particular embodiment of the invention in the compound of formula (I) Y is selected from –SO$_3$H, —SO$_3^-$.X$^+$, —SO$_3$R$_3$, —CO$_2$H, —CO$_2^-$.X$^+$ and —CO$_2$R$_3$.

In another particular embodiment, in the compound of formula (I) at least one of $R_9$ and $R_{9'}$ are, independently, a substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group.

In another particular embodiment, $R_2$ is selected from methylcarbonyl, phenylsulfonyl, 4-methylphenylsulfonyl, benzylsulfonyl, benzyl and phenyl.

In another embodiment of the invention, $R_2$ is selected from acetyl (—C(O)CH$_3$), tosyl (—SO$_2$—C$_6$H$_4$—CH$_3$) and p-chlorophenoxyisobutyryl (—C(O)—C(CH$_3$)$_2$—O—C$_6$H$_4$Cl).

In another embodiment, $R_3$ is selected from methyl, ethyl, isopropyl and C$_6$H$_5$—, more particularly from methyl and ethyl.

In one embodiment of the invention, the inorganic cation is sodium, potassium, lithium, calcium, or magnesium.

In another embodiment of the invention, the organic cation is [NH$_{4-p}$R$_p$]$^+$: wherein p is in each case selected independently from an integer number from 0 to 4, both included; and R is an alkyl group of one to six carbon atoms such as, for example, methyl, ethyl, n-propyl, i-propyl, n-butyl, t-butyl, or n-pentyl.

In another embodiment of the invention, the organic cations are a diethylamine [H$_2$N$^+$(C$_2$H$_5$)$_2$], piperazine or pyridine group.

In other embodiments of the invention, the compounds of Formula (I) and pharmaceutically acceptable salts thereof are:

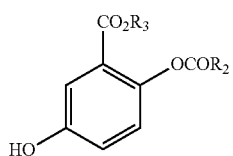
(15)
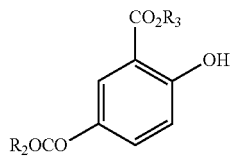
(16)
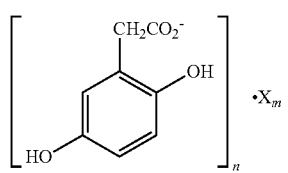
(17)
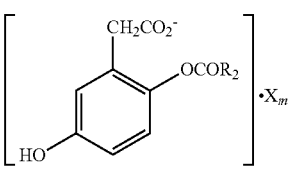
(18)
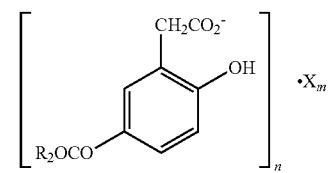
(19)
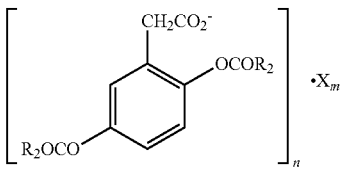
(20)
(21)
(22)
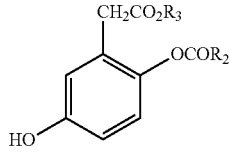
(23)
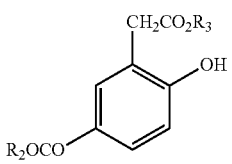
(24)
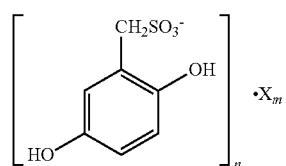
(25)
(26)
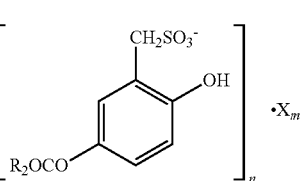
(27)
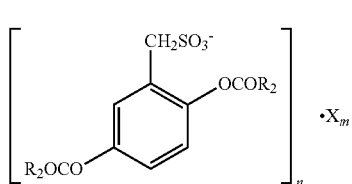
(28)
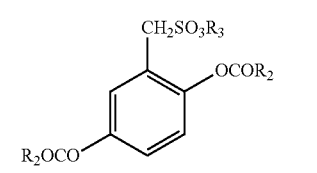
(29)
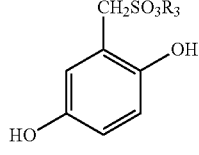
(30)
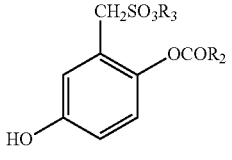
(31)
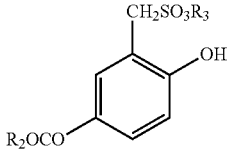
(32)

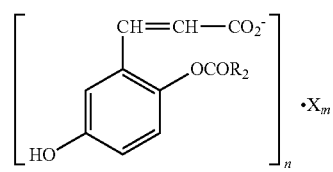
(33)

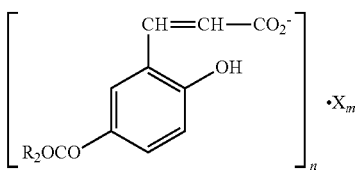
(34)

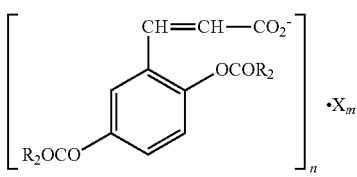
(35)

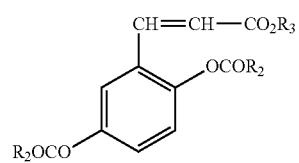
(36)

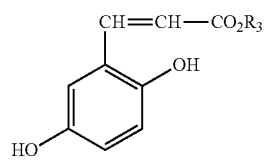
(37)

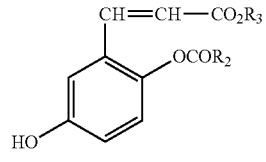
(38)

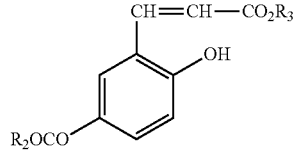
(39)

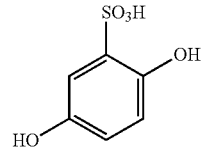
(40)

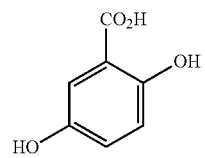
(41)

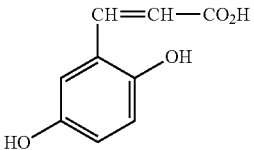
(42)

wherein:
n is an integer selected from 1 and 2;
m is an integer selected from 1 and 2; and
X, $R_2$ and $R_3$ are as defined herein.

In one preferred embodiment, the compound of Formula (I) is selected from the group consisting of:
2,5-dihydroxybenzenesulfonic acid (Dobesilate),
5-hydroxy-2-{[(4-methylphenyl)sulfonyl]oxy}benzenesulfonic acid;
2-hydroxy-5-{[(4-methylphenyl)sulfonyl]oxy}benzenesulfonic acid;
2,5-bis{[(4-methylphenyl)sulfonyl]oxy}benzenesulfonic acid;
2-(acetyloxy)-5-hydroxybenzenesulfonic acid;
5-(acetyloxy)-2-hydroxybenzenesulfonic acid;
2,5-bis(acetyloxy)benzenesulfonic acid;
2-(benzyloxy)-5-hydroxybenzenesulfonic acid;
5-(benzyloxy)-2-hydroxybenzenesulfonic acid;
2,5-bis(benzyloxy)benzenesulfonic acid;
2,5-dihydroxybenzene homosulfonic acid (homodobesilate)
5-hydroxy-2-{[(4-methylphenyl)sulfonyl]oxy}benzenehomosulfonic acid;
2-hydroxy-5-{[(4-methylphenyl)sulfonyl]oxy}benzenehomosulfonic acid;
2,5-bis{[(4-methylphenyl)sulfonyl]oxy}benzenehomosulfonic acid;
2-(acetyloxy)-5-hydroxybenzenehomosulfonic acid;
5-(acetyloxy)-2-hydroxybenzenehomosulfonic acid;
2,5-bis(acetyloxy)benzenehomosulfonic acid;
2-(benzyloxy)-5-hydroxybenzenehomosulfonic acid;
5-(benzyloxy)-2-hydroxybenzenehomosulfonic acid;
2,5-bis(benzyloxy)benzenehomosulfonic acid;
2,5-dihydroxybenzoic acid (gentisic acid),
5-hydroxy-2-{[(4-methylphenyl)sulfonyl]oxy}benzoic acid;
2-hydroxy-5-{[(4-methylphenyl)sulfonyl]oxy}benzoic acid;
2,5-bis{[(4-methylphenyl)sulfonyl]oxy}benzoic acid;
2-(acetyloxy)-5-hydroxybenzoic acid;
5-(acetyloxy)-2-hydroxybenzoic acid;
2,5-bis(acetyloxy)benzoic acid;
2-(benzyloxy)-5-hydroxybenzoic acid;
5-(benzyloxy)-2-hydroxybenzoic acid;
2,5-bis(benzyloxy)benzoic acid;
2,5-dihydroxyhomobenzoic acid (homogentisic acid),
5-hydroxy-2-{[(4-methylphenyl)sulfonyl]oxy}homobenzoic acid;
2-hydroxy-5-{[(4-methylphenyl)sulfonyl]oxy}homobenzoic acid;
2,5-bis{[(4-methylphenyl)sulfonyl]oxy}homobenzoic acid;
2-(acetyloxy)-5-hydroxyhomobenzoic acid;
5-(acetyloxy)-2-hydroxyhomobenzoic acid;
2,5-bis(acetyloxy) homobenzoic acid;
2-(benzyloxy)-5-hydroxyhomobenzoic acid;
5-(benzyloxy)-2-hydroxyhomobenzoic acid;
2,5-bis(benzyloxy) homobenzoic acid;
3-(2,5-dihydroxyphenyl)-2-propenoic acid (2,5-dihydroxycinnamic acid);
3-(5-hydroxy-2-{[(4-methylphenyl)sulfonyl]oxy}phenyl)-2-propenoic acid;
3-(2-hydroxy-5-{[(4-methylphenyl)sulfonyl]oxy}phenyl)-2-propenoic acid;

3-(2,5-bis{[(4-methylphenyl)sulfonyl]oxy}phenyl)-2-propenoic acid;
3-(2-(acetyloxy)-5-hydroxyphenyl)-2-propenoic acid;
3-(5-(acetyloxy)-2-hydroxyphenyl)-2-propenoic acid;
3-(2,5-bis(acetyloxy)phenyl)-2-propenoic acid;
3-(2-(benzyloxy)-5-hydroxyphenyl)-2-propenoic acid;
3-(5-(benzyloxy)-2-hydroxyphenyl)-2-propenoic acid;
3-(2,5-bis(benzyloxy)phenyl)-2-propenoic acid;
and pharmaceutically acceptable salts and solvates thereof, isomers, prodrugs and esters.

In another particular embodiment, the compounds of Formula (I) are in the form of esters at position 1, in particular methyl and ethyl esters.

Preferred compounds of formula I are those selected from 2-(acetyloxy)-5-hydroxybenzenesulfonic acid; 5-(acetyloxy)-2-hydroxybenzenesulfonic acid and 2,5-bis(acetyloxy)benzenesulfonic acid.

Other preferred compounds of Formula (I) are those selected from the group consisting of:
calcium 2,5-dihydroxybenzenesulfonate (calcium Dobesilate);
potassium 2,5-dihydroxybenzenesulfonate (potassium Dobesilate);
magnesium 2,5-dihydroxybenzenesulfonate (magnesium Dobesilate);
diethylamine 2,5-dihydroxybenzenesulfonate (Ethamsylate).

The invention provides compositions comprising at least one compound of Formula (I) and at least one additional therapeutic agent, including but not limited to chemotherapeutic agent, a corticosteroid, an antibiotic, an analgesic, an antiandrogen, an immunomodulator, an anti-angiogenic, including anti-VEGF, anti-FGF, anti-EGF and anti-HGF; inhibitors of tyrosin-kinase receptors, protein kinase C inhibitors, a non-steroidal anti-inflammatory, a therapy of the solubilized interleukin receptor, a cytotoxic, an antioxidant and combinations of two or more thereof.

The compounds of Formula (I) can optionally be used together with one or more additional therapeutic agents, such as chemotherapeutic agent, a corticosteroid, an antibiotic, an analgesic, an antiandrogen, an immunomodulator, an anti-angiogenic, including anti-VEGF, anti-FGF, anti-EGF and anti-HGF; inhibitors of tyrosin-kinase receptors, protein kinase C inhibitors, a non-steroidal anti-inflammatory, a therapy of the solubilized interleukin receptor, a cytotoxic, an antioxidant and combinations of two or more thereof.

In a second aspect, the present invention relates to the use of a compound of Formula (I') or pharmaceutically acceptable salt or solvate, isomer or prodrug thereof in the manufacturing of a medicament for the treatment and/or prophylaxis of any of the diseases selected from the group consisting of benign prostatic hyperplasia, Barrett's disease, asthma, skeletal muscle and tendon repair, Crohn's disease, ulcerative colitis and leishmaniasis, wherein the compound of Formula (I'):

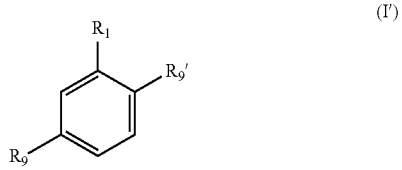

wherein:
$R_1$ is —$(CH_2)_a Y$ (or —CH=CH—$(CH_2)_p Y$;
$Y$ is —$SO_3H$, —$SO_3^-.X^+$, —$SO_3R_3$, —$PO_3H$, —$PO_3^-.X^+$, —$PO_3R_3$, —$CO_2H$, —$CO_2^-.X^+$ or —$CO_2R_3$;

$X^+$ is an organic cation or an inorganic cation, such that the general charge of the compound is neutral;
$R_9$ and $R_{9'}$ are independently selected from —OH and —$OR_2$, wherein when $R_9$ and $R_{9'}$, are both —$OR_2$, then said $R_9$ and $R_{9'}$, can be the same or different;
$R_2$ is a substituted or unsubstituted alkyl group, a substituted or unsubstituted aryl group, a substituted or unsubstituted arylalkyl group, a substituted or unsubstituted alkylsulfonyl group, a substituted or unsubstituted arylsulfonyl group, a substituted or unsubstituted alkylarylsulfonyl group, a substituted or unsubstituted arylalkysulfonyl group, a substituted or unsubstituted aryloxyalkyl group, a substituted or unsubstituted alkylcarbonyl group or an arylcarbonyl group, a carboxyl group, a substituted or unsubstituted alkoxycarbonyl group, a substituted or unsubstituted carboxyalkyl group, in particular —$CH_2$—COOH, or a substituted or unsubstituted alkoxyaryloxy- arylalkoxy- or alkylaryloxy-carbonylalkyl, in particular —$CH_2$—$COOR_3$;
$R_3$ is a substituted or unsubstituted alkyl group or a substituted or unsubstituted aryl group;
a is number selected from 0, 1, 2, 3, 4, 5 and 6;
p is an integer selected from 0, 1, 2, 3, 4, 5 and 6.

In a particular embodiment, 2,5-dihydroxybenzene derivatives of the invention or any of the pharmaceutically acceptable salts thereof are those that are represented by Formula (I') comprising dobesilate esters derivatives or pharmaceutically acceptable salts or esters thereof for the treatment of benign prostatic hyperplasia, Barrett's disease, asthma, skeletal muscle and tendon repair, Crohn's disease, ulcerative colitis or leishmaniasis.

The $X^+$ cation in the Compounds of Formula (I') may be any physiologically acceptable cation known by a skilled in the art and includes, but is not limited to, those described in Heinrich Stahl, Camille G. Wermuth (eds.), "Handbook of Pharmaceutical Salts Properties, Selections and Use", Verlag Helvetica Chimica Acta, Zurich, Switzerland, Wiley-VCH, Weinheim, Germany, 2002; the disclosures of which are incorporated herein by reference in their entirety. The $X^+$ cation is selected in such a way that the total charge of the compounds of Formula (I') is neutral.

In a particular embodiment of the invention in the compound of formula (I') Y is selected from –$SO_3H$, —$SO_3^-.X^+$, —$SO_3R_3$, —$CO_2H$, —$CO_2^-.X^+$ and —$CO_2R_3$.

In another particular embodiment, in the compound of formula (I') at least one of $R_9$ and $R_{9'}$ are, independently, a substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group.

In another particular embodiment, $R_2$ is selected from methylcarbonyl, phenylsulfonyl, 4-methylphenylsulfonyl, benzylsulfonyl, benzyl and phenyl.

In another embodiment of the invention, $R_2$ is selected from acetyl (—C(O)CH$_3$), tosyl (—SO$_2$—C$_6$H$_4$—CH$_3$) and p-chlorophenoxyisobutyryl (—C(O)—C(CH$_3$)$_2$—O—C6H$_4$Cl).

In another embodiment, $R_3$ is selected from methyl, ethyl, isopropyl and C$_6$H$_5$—, more particularly from methyl and ethyl.

In one embodiment of the invention, the inorganic cation is sodium, potassium, lithium, calcium, or magnesium.

In another embodiment of the invention, the organic cation is [NH$_{4-p}$R$_p$]$^+$: wherein p is in each case selected independently from an integer number from 0 to 4, both included; and R is an alkyl group of one to six carbon atoms such as, for example, methyl, ethyl, n-propyl, i-propyl, n-butyl, t-butyl, or n-pentyl.

In another embodiment of the invention, the organic cations are a diethylamine [$H_2N^+(C_2H_5)_2$], piperazine or pyridine group.

In other embodiments of the invention, the compounds of Formula (I') and pharmaceutically acceptable salts thereof are:

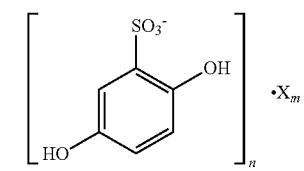
(1)

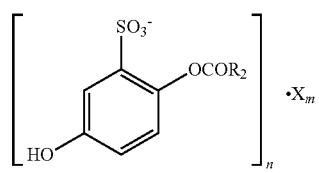
(2)

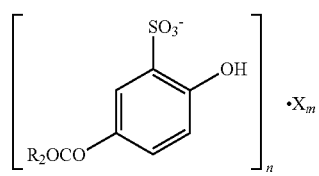
(3)

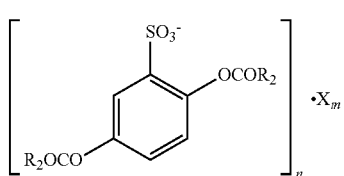
(4)

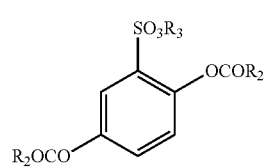
(5)

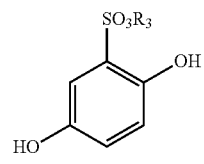
(6)

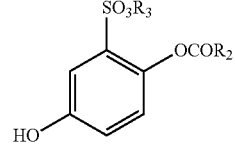
(7)

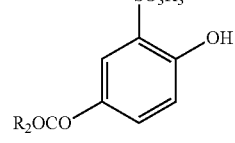
(8)

-continued

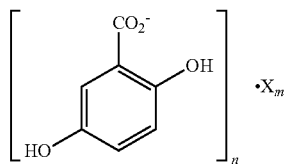
(9)

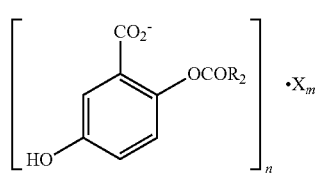
(10)

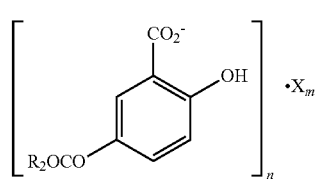
(11)

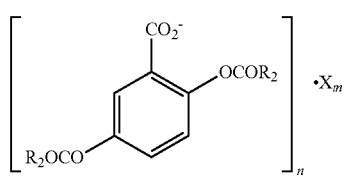
(12)

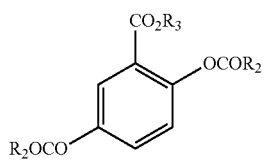
(13)

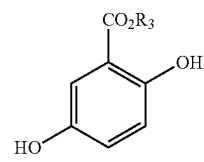
(14)

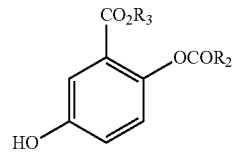
(15)

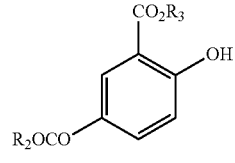
(16)

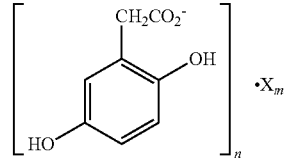
(17)

(18) 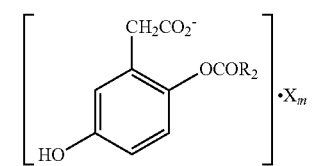
(19) 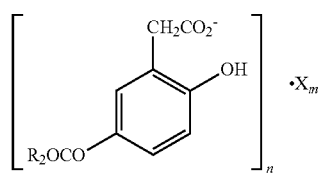
(20) 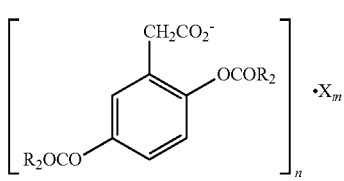
(21) 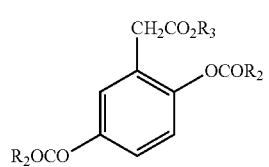
(22) 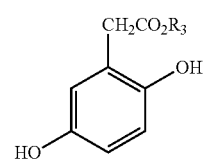
(23) 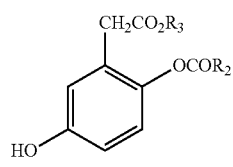
(24) 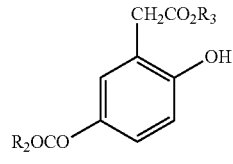
(25) 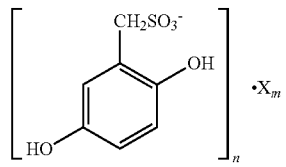
(26) 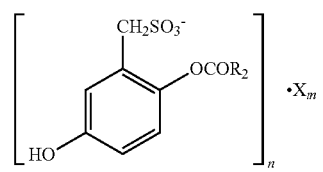
(27) 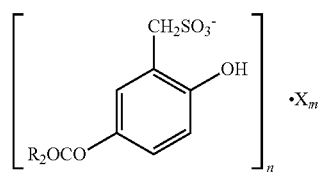
(28) 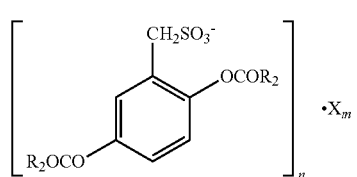
(29) 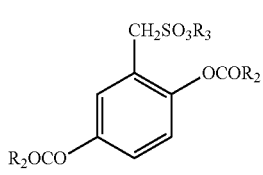
(30) 
(31) 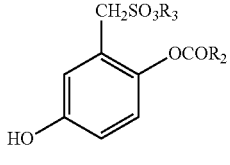
(32) 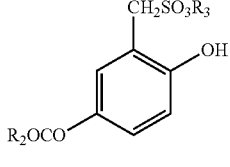
(33) 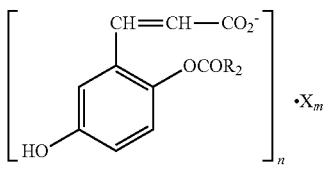
(34) 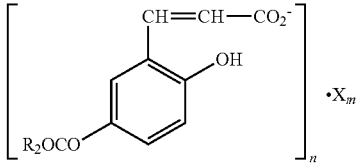
(35) 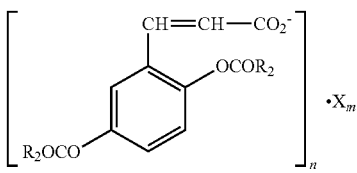

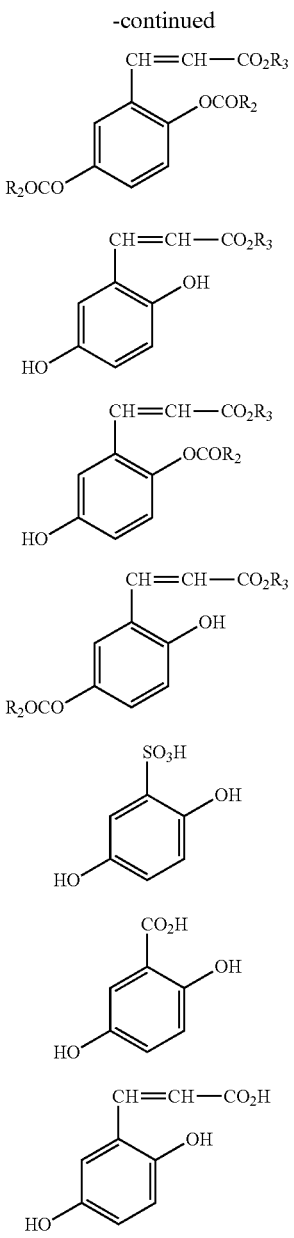

(36)
(37)
(38)
(39)
(40)
(41)
(42)

wherein:
n is an integer selected from 1 and 2;
m is an integer selected from 1 and 2; and
X, $R_2$ and $R_3$ are as defined herein.

In one preferred embodiment, the compound of Formula (I') is selected from the group consisting of:
2,5-dihydroxybenzenesulfonic acid (Dobesilate),
5-hydroxy-2-{[(4-methylphenyl)sulfonyl]oxy}benzenesulfonic acid;
2-hydroxy-5-{[(4-methylphenyl)sulfonyl]oxy}benzenesulfonic acid;
2,5-bis{[(4-methylphenyl)sulfonyl]oxy}benzenesulfonic acid;
2-(acetyloxy)-5-hydroxybenzenesulfonic acid;
5-(acetyloxy)-2-hydroxybenzenesulfonic acid;
2,5-bis(acetyloxy)benzenesulfonic acid;
2-(benzyloxy)-5-hydroxybenzenesulfonic acid;
5-(benzyloxy)-2-hydroxybenzenesulfonic acid;
2,5-bis(benzyloxy)benzenesulfonic acid;
2,5-dihydroxybenzene homosulfonic acid (homodobesilate)
5-hydroxy-2-{[(4-methylphenyl)sulfonyl]oxy}benzenehomosulfonic acid;
2-hydroxy-5-{[(4-methylphenyl)sulfonyl]oxy}benzenehomosulfonic acid;
2,5-bis{[(4-methylphenyl)sulfonyl]oxy}benzenehomosulfonic acid;
2-(acetyloxy)-5-hydroxybenzenehomosulfonic acid;
5-(acetyloxy)-2-hydroxybenzenehomosulfonic acid;
2,5-bis(acetyloxy)benzenehomosulfonic acid;
2-(benzyloxy)-5-hydroxybenzenehomosulfonic acid;
5-(benzyloxy)-2-hydroxybenzenehomosulfonic acid;
2,5-bis(benzyloxy)benzenehomosulfonic acid;
2,5-dihydroxybenzoic acid (gentisic acid),
5-hydroxy-2-{[(4-methylphenyl)sulfonyl]oxy}benzoic acid;
2-hydroxy-5-{[(4-methylphenyl)sulfonyl]oxy}benzoic acid;
2,5-bis{[(4-methylphenyl)sulfonyl]oxy}benzoic acid;
2-(acetyloxy)-5-hydroxybenzoic acid;
5-(acetyloxy)-2-hydroxybenzoic acid;
2,5-bis(acetyloxy)benzoic acid;
2-(benzyloxy)-5-hydroxybenzoic acid;
5-(benzyloxy)-2-hydroxybenzoic acid;
2,5-bis(benzyloxy)benzoic acid;
2,5-dihydroxyhomobenzoic acid (homogentisic acid),
5-hydroxy-2-{[(4-methylphenyl)sulfonyl]oxy}homobenzoic acid;
2-hydroxy-5-{[(4-methylphenyl)sulfonyl]oxy}homobenzoic acid;
2,5-bis{[(4-methylphenyl)sulfonyl]oxy}homobenzoic acid;
2-(acetyloxy)-5-hydroxyhomobenzoic acid;
5-(acetyloxy)-2-hydroxyhomobenzoic acid;
2,5-bis(acetyloxy) homobenzoic acid;
2-(benzyloxy)-5-hydroxyhomobenzoic acid;
5-(benzyloxy)-2-hydroxyhomobenzoic acid;
2,5-bis(benzyloxy) homobenzoic acid;
3-(2,5-dihydroxyphenyl)-2-propenoic acid (2,5-dihydroxycinnamic acid);
3-(5-hydroxy-2-{[(4-methylphenyl)sulfonyl]oxy}phenyl)-2-propenoic acid;
3-(2-hydroxy-5-{[(4-methylphenyl)sulfonyl]oxy}phenyl)-2-propenoic acid;
3-(2,5-bis{[(4-methylphenyl)sulfonyl]oxy}phenyl)-2-propenoic acid;
3-(2-(acetyloxy)-5-hydroxyphenyl)-2-propenoic acid;
3-(5-(acetyloxy)-2-hydroxyphenyl)-2-propenoic acid;
3-(2,5-bis(acetyloxy)phenyl)-2-propenoic acid;
3-(2-(benzyloxy)-5-hydroxyphenyl)-2-propenoic acid;
3-(5-(benzyloxy)-2-hydroxyphenyl)-2-propenoic acid;
3-(2,5-bis(benzyloxy)phenyl)-2-propenoic acid;
and pharmaceutically acceptable salts and solvates thereof, isomers, prodrugs and esters.

In another particular embodiment, the compounds of Formula (I') are in the form of esters at position 1, in particular methyl and ethyl esters.

Preferred compounds of formula (I') are those selected from 2-(acetyloxy)-5-hydroxybenzenesulfonic acid; 5-(acetyloxy)-2-hydroxybenzenesulfonic acid and 2,5-bis(acetyloxy)benzenesulfonic acid.

Other preferred compounds of Formula (I') are those selected from the group consisting of:
calcium 2,5-dihydroxybenzenesulfonate (calcium Dobesilate);
potassium 2,5-dihydroxybenzenesulfonate (potassium Dobesilate);
magnesium 2,5-dihydroxybenzenesulfonate (magnesium Dobesilate);

diethylamine 2,5-dihydroxybenzenesulfonate (Ethamsylate).

The invention provides compositions comprising at least one compound of Formula (I') and at least one additional therapeutic agent, including but not limited to a chemotherapeutic agent, a corticosteroid, an antibiotic, an analgesic, an alpha-adrenergic blocker, a beta-adrenergic agonist, an anticholinergic, an inhibitor of 5-alpha-reductase, an antiandrogen, an oral contraceptive, an immunomodulator, an immunosuppressant, an anti-angiogenic, a bronchodilator, a leukotriene modifier, an aminosalicylate, an anesthetic, a non-steroidal anti-inflammatory, an antiparasitic, a proton pump inhibitor, an H2-receptor antagonist, a therapy of the solubilized interleukin receptor, intramuscular gold, a cytotoxic, an antioxidant and combinations of two or more thereof.

The compounds of Formula (I') can optionally be used together with one or more additional therapeutic agents, such as a chemotherapeutic agent, a corticosteroid, an antibiotic, an analgesic, an alpha-adrenergic blocker, a beta-adrenergic agonist, an anticholinergic, an inhibitor of 5-alpha-reductase, an antiandrogen, an oral contraceptive, an immunomodulator, an immunosuppressant, an anti-angiogenic, a bronchodilator, a leukotriene modifier, an aminosalicylate, an anesthetic, a non-steroidal anti-inflammatory, an antiparasitic, a proton pump inhibitor, an H2-receptor antagonist, a therapy of the solubilized interleukin receptor, intramuscular gold, a cytotoxic, an antioxidant and combinations of two or more thereof.

In a third aspect, the present invention relates to the use of a compound of Formula (I″) or pharmaceutically acceptable salt or solvate, isomer or prodrug thereof in the manufacturing of a medicament for the treatment and/or prophylaxis of any of the diseases selected from the group consisting of diseases associated to *Helicobacter pylori* infection, pterygium, endometrosis, ovarian hyperstimulation syndrome and polycystic kidney disease, wherein the compound of Formula (I″) is:

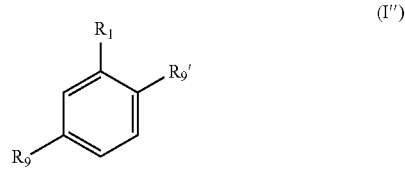

(I″)

wherein:
$R_1$ is —$(CH_2)_a Y$ (or —CH═CH—$(CH_2)_p Y$;
Y is —$SO_3H$, —$SO_{3g-}.X^+$, —$SO_3R_3$, —$PO_3H$, —$PO_3$—$.X^+$, —$PO_3R_3$, —$CO_2H$, —$CO_2^-.X^+$ or —$CO_2R_3$;
$X^+$ is an organic cation or an inorganic cation, such that the general charge of the compound of formula (I) is neutral;
$R_9$ and $R_{9'}$ are individually selected from —OH and —$OR_2$; wherein when $R_9$ and $R_{9'}$ are both —$OR_2$, then said $R_9$ and $R_{9'}$ can be the same or different;
$R_2$ is a substituted or unsubstituted alkyl group, a substituted or unsubstituted aryl group, a substituted or unsubstituted arylalkyl group, a substituted or unsubstituted alkylsulfonyl group, a substituted or unsubstituted arylsulfonyl group, a substituted or unsubstituted alkylarylsulfonyl group, a substituted or unsubstituted arylalkysulfonyl group, a substituted or unsubstituted aryloxyalkyl group, a substituted or unsubstituted alkylcarbonyl group or an arylcarbonyl group, a carboxyl group, a substituted or unsubstituted alkoxycarbonyl group, a substituted or unsubstituted carboxyalkyl group, in particular —$CH_2$—COOH, or a substituted or unsubstituted alkoxyaryloxy- arylalkoxy- or alkylaryloxy-carbonylalkyl, in particular —$CH_2$—$COOR_3$;
$R_3$ is a substituted or unsubstituted alkyl group or a substituted or unsubstituted aryl group;
a is number selected from 0, 1, 2, 3, 4, 5 and 6;
p is an integer selected from 0, 1, 2, 3, 4, 5 and 6;
with the proviso that when Y is —$SO_3H$, —$SO_3^-.X^+$ or —$SO_3R_3$, then $R_9$ and $R_{9'}$ are independently selected from —OH and —$OR_2$, wherein at least one of $R_9$ and $R_{9'}$ is a substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group.

In a particular embodiment, 2,5-dihydroxybenzene derivatives of the invention or any of the pharmaceutically acceptable salts thereof are those that are represented by Formula (I″) comprising dobesilate esters derivatives or pharmaceutically acceptable salts or esters thereof for the treatment of diseases associated to *Helicobacter pylori* infection, pterygium, endometrosis, ovarian hyperstimulation syndrome or polycystic kidney disease.

The $X^+$ cation in the Compounds of Formula (I″) may be any physiologically acceptable cation known by a skilled in the art and includes, but is not limited to, those described in Heinrich Stahl, Camille G. Wermuth (eds.), "Handbook of Pharmaceutical Salts Properties, Selections and Use", Verlag Helvetica Chimica Acta, Zurich, Switzerland, Wiley-VCH, Weinheim, Germany, 2002; the disclosures of which are incorporated herein by reference in their entirety. The $X^+$ cation is selected in such a way that the total charge of the compounds of Formula (I″) is neutral.

In a particular embodiment of the invention in the compound of formula (I″) Y is selected from –$SO_3H$, —$SO_3^-.X^+$, —$SO_3R_3$, —$CO_2H$, —$CO_2^-.X^+$ and —$CO_2R_3$.

In another particular embodiment, in the compound of formula (I″) at least one of $R_9$ and $R_{9'}$ are, independently, a substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group.

In another particular embodiment, $R_2$ is selected from methylcarbonyl, phenylsulfonyl, 4-methylphenylsulfonyl, benzylsulfonyl, benzyl and phenyl In another embodiment of the invention, $R_2$ is selected from acetyl (—$C(O)CH_3$), tosyl (—$SO_2$—$C_6H_4$—$CH_3$) and p-chlorophenoxyisobutyryl (—$C(O)$—$C(CH_3)_2$—O—C6H4Cl).

In another embodiment, $R_3$ is selected from methyl, ethyl, isopropyl and $C_6H_{5-5}$ more particularly from methyl and ethyl.

In one embodiment of the invention, the inorganic cation is sodium, potassium, lithium, calcium, or magnesium.

In another embodiment of the invention, the organic cation is $[NH_{4-p}R_p]^+$: wherein p is in each case selected independently from an integer number from 0 to 4, both included; and R is an alkyl group of one to six carbon atoms such as, for example, methyl, ethyl, n-propyl, i-propyl, n-butyl, t-butyl, or n-pentyl.

In another embodiment of the invention, the organic cations are a diethylamine
$[H_2N^+(C_2H_5)_2]$, piperazine or pyridine group.
In other embodiments of the invention, the compounds of Formula (I") and pharmaceutically acceptable salts thereof are:
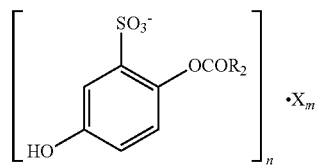
(1)
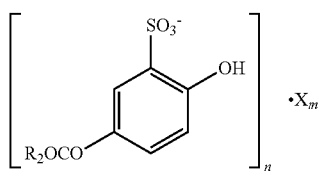
(2)
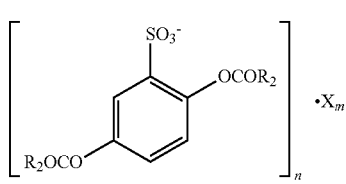
(3)
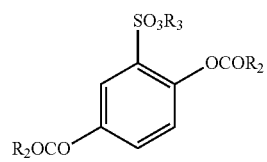
(4)
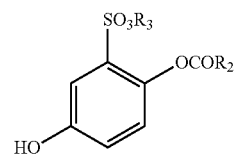
(5)
(6)
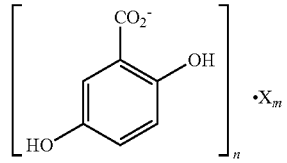
(7)
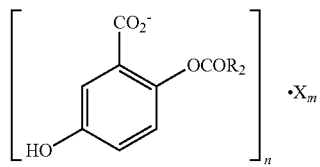
(8)
-continued
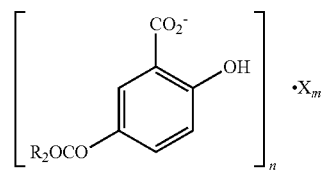
(9)
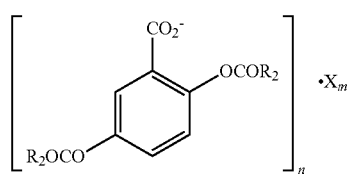
(10)
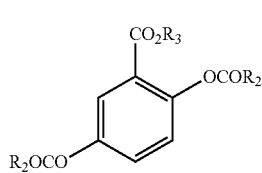
(11)
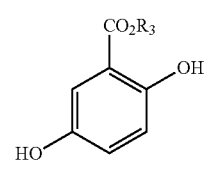
(12)
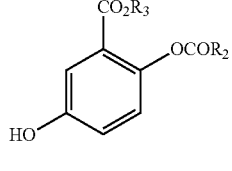
(13)
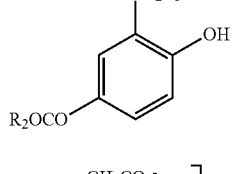
(14)
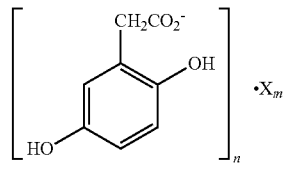
(15)
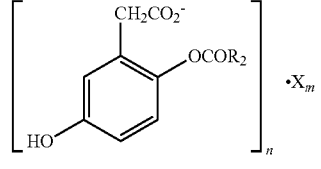
(16)
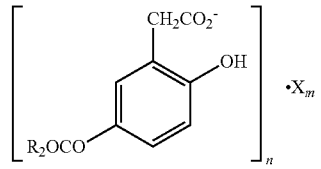
(17)

-continued
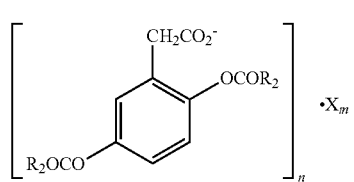 (18)
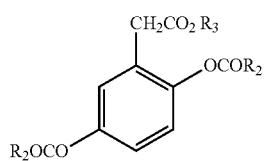 (19)
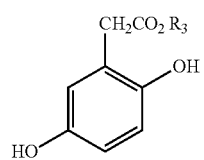 (20)
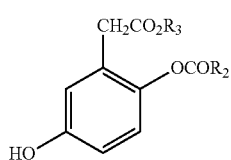 (21)
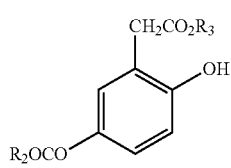 (22)
 (23)
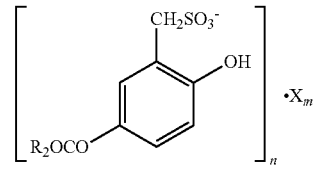 (24)
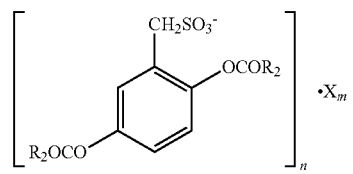 (25)
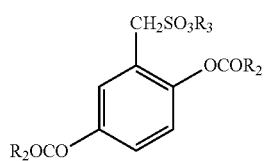 (26)
-continued
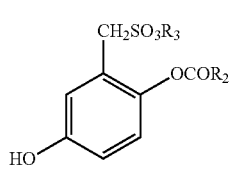 (27)
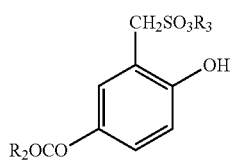 (28)
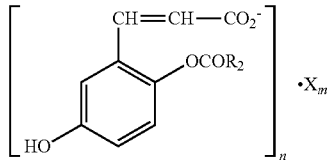 (29)
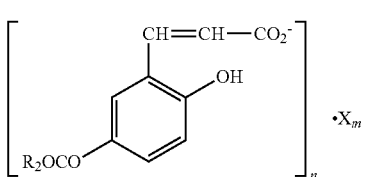 (30)
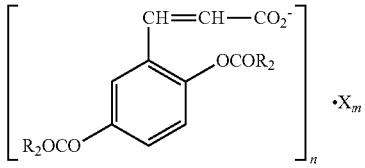 (31)
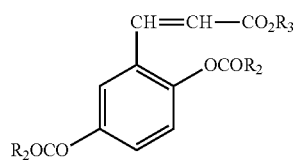 (32)
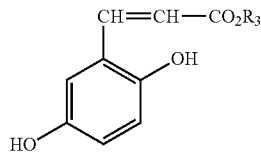 (33)
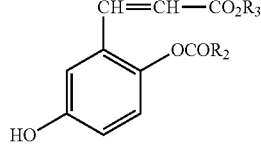 (34)
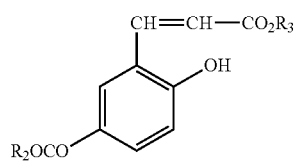 (35)

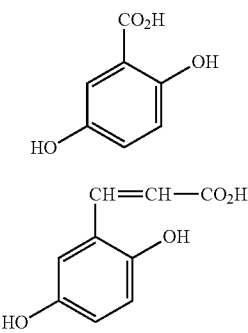

wherein:
n is an integer selected from 1 and 2;
m is an integer selected from 1 and 2; and
X, $R_2$ and $R_3$ are as defined herein.

In one preferred embodiment, the compound of Formula (I″) is selected from the group consisting of:
5-hydroxy-2-{[(4-methylphenyl)sulfonyl]oxy}benzenesulfonic acid;
2-hydroxy-5-{[(4-methylphenyl)sulfonyl]oxy}benzenesulfonic acid;
2,5-bis{[(4-methylphenyl)sulfonyl]oxy}benzenesulfonic acid;
2-(acetyloxy)-5-hydroxybenzenesulfonic acid;
5-(acetyloxy)-2-hydroxybenzenesulfonic acid;
2,5-bis(acetyloxy)benzenesulfonic acid;
5-hydroxy-2-{[(4-methylphenyl)sulfonyl]oxy}benzenehomosulfonic acid;
2-hydroxy-5-{[(4-methylphenyl)sulfonyl]oxy}benzenehomosulfonic acid;
2,5-bis{[(4-methylphenyl)sulfonyl]oxy}benzenehomosulfonic acid;
2-(acetyloxy)-5-hydroxybenzenehomosulfonic acid;
5-(acetyloxy)-2-hydroxybenzenehomosulfonic acid;
2,5-bis(acetyloxy)benzenehomosulfonic acid;
2,5-dihydroxybenzoic acid (gentisic acid),
5-hydroxy-2-{[(4-methylphenyl)sulfonyl]oxy}benzoic acid;
2-hydroxy-5-{[(4-methylphenyl)sulfonyl]oxy}benzoic acid;
2,5-bis{[(4-methylphenyl)sulfonyl]oxy}benzoic acid;
2-(acetyloxy)-5-hydroxybenzoic acid;
5-(acetyloxy)-2-hydroxybenzoic acid;
2,5-bis(acetyloxy)benzoic acid;
2-(benzyloxy)-5-hydroxybenzoic acid;
5-(benzyloxy)-2-hydroxybenzoic acid;
2,5-bis(benzyloxy)benzoic acid;
2,5-dihydroxyhomobenzoic acid (homogentisic acid),
5-hydroxy-2-{[(4-methylphenyl)sulfonyl]oxy}homobenzoic acid;
2-hydroxy-5-{[(4-methylphenyl)sulfonyl]oxy}homobenzoic acid;
2,5-bis{[(4-methylphenyl)sulfonyl]oxy}homobenzoic acid;
2-(acetyloxy)-5-hydroxyhomobenzoic acid;
5-(acetyloxy)-2-hydroxyhomobenzoic acid;
2,5-bis(acetyloxy) homobenzoic acid;
2-(benzyloxy)-5-hydroxyhomobenzoic acid;
5-(benzyloxy)-2-hydroxyhomobenzoic acid;
2,5-bis(benzyloxy) homobenzoic acid;
3-(2,5-dihydroxyphenyl)-2-propenoic acid (2,5-dihydroxycinnamic acid);
3-(5-hydroxy-2-{[(4-methylphenyl)sulfonyl]oxy}phenyl)-2-propenoic acid;
3-(2-hydroxy-5-{[(4-methylphenyl)sulfonyl]oxy}phenyl)-2-propenoic acid;
3-(2,5-bis{[(4-methylphenyl)sulfonyl]oxy}phenyl)-2-propenoic acid;
3-(2-(acetyloxy)-5-hydroxyphenyl)-2-propenoic acid;
3-(5-(acetyloxy)-2-hydroxyphenyl)-2-propenoic acid;
3-(2,5-bis(acetyloxy)phenyl)-2-propenoic acid;
3-(2-(benzyloxy)-5-hydroxyphenyl)-2-propenoic acid;
3-(5-(benzyloxy)-2-hydroxyphenyl)-2-propenoic acid;
3-(2,5-bis(benzyloxy)phenyl)-2-propenoic acid;
and pharmaceutically acceptable salts and solvates thereof, isomers, prodrugs and esters.

In another particular embodiment, the compounds of Formula (I″) are in the form of esters at position 1, in particular methyl and ethyl esters.

Preferred compounds of formula (I″) are those selected from 2-(acetyloxy)-5-hydroxybenzenesulfonic acid; 5-(acetyloxy)-2-hydroxybenzenesulfonic acid and 2,5-bis(acetyloxy)benzenesulfonic acid.

The invention provides compositions comprising at least one compound of Formula (I″) and at least one additional therapeutic agent, including but not limited to a chemotherapeutic agent, a corticosteroid, an antibiotic, an analgesic, an alpha-adrenergic blocker, a beta-adrenergic agonist, an anticholinergic, an inhibitor of 5-alpha-reductase, an antiandrogen, an oral contraceptive, an immunomodulator, an immunosuppressant, an anti-angiogenic, a bronchodilator, a leukotriene modifier, an aminosalicylate, an anesthetic, a non-steroidal anti-inflammatory, an antiparasitic, a proton pump inhibitor, an H2-receptor antagonist, a therapy of the solubilized interleukin receptor, intramuscular gold, a cytotoxic, an antioxidant and combinations of two or more thereof.

The compounds of Formula (I″) can optionally be used together with one or more additional therapeutic agents, such as a chemotherapeutic agent, a corticosteroid, an antibiotic, an analgesic, an alpha-adrenergic blocker, a beta-adrenergic agonist, an anticholinergic, an inhibitor of 5-alpha-reductase, an antiandrogen, an oral contraceptive, an immunomodulator, an immunosuppressant, an anti-angiogenic, a bronchodilator, a leukotriene modifier, an aminosalicylate, an anesthetic, a non-steroidal anti-inflammatory, an antiparasitic, a proton pump inhibitor, an H2-receptor antagonist, a therapy of the solubilized interleukin receptor, intramuscular gold, a cytotoxic, an antioxidant and combinations of two or more thereof.

In a fourth aspect, the present invention relates to the use of a compound of Formula (I‴) or pharmaceutically acceptable salt or solvate, isomer or prodrug thereof in the manufacturing of a medicament for the treatment and/or prophylaxis of arthritis or pain, wherein the compound of Formula (I‴):

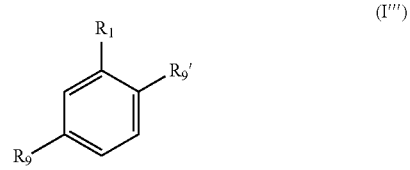

wherein:
$R_1$ is —$(CH_2)_a$Y or —CH=CH—$(CH_2)_p$Z;
Y is —$SO_3H$, —$SO_3^-.X^+$, —$SO_3R_3$, —$PO_3H$, —$PO_3^-.X^+$, —$PO_3R_3$;

Z is —SO$_3^-$.X$^+$, —SO$_3$R$_3$, —SO$_3$R$_3$, —PO$_3$—X$^+$, —PO$_3$—X$^+$, —PO$_3$R$_3$, —CO$_2$H, —CO$_2^-$.X$^+$ or —CO$_2$R$_3$;

X$^+$ is an organic cation or an inorganic cation, such that the general charge of the compound is neutral;

R$_9$ and R$_{9'}$ are independently selected from —OH and —OR$_2$, wherein when R$_9$ and R$_{9'}$ are both —OR$_2$, then said R$_9$ and R$_{9'}$ can be the same or different;

R$_2$ is a substituted or unsubstituted alkyl group, a substituted or unsubstituted aryl group, a substituted or unsubstituted arylalkyl group, a substituted or unsubstituted alkylsulfonyl group, a substituted or unsubstituted arylsulfonyl group, a substituted or unsubstituted alkylarylsulfonyl group, a substituted or unsubstituted arylalkysulfonyl group, a substituted or unsubstituted aryloxyalkyl group, a substituted or unsubstituted alkylcarbonyl group or an arylcarbonyl group, a carboxyl group, a substituted or unsubstituted alkoxycarbonyl group, a substituted or unsubstituted carboxyalkyl group, in particular —CH$_2$—COOH, or a substituted or unsubstituted alkoxy-aryloxy- arylalkoxy- or alkylaryloxy-carbonylalkyl, in particular —CH$_2$—COOR$_3$;

R$_3$ is a substituted or unsubstituted alkyl group or a substituted or unsubstituted aryl group;

a is number selected from 0, 1, 2, 3, 4, 5 and 6;

p is an integer selected from 0, 1, 2, 3, 4, 5 and 6, with the proviso that when Y is —SO$_3$H, —SO$_3^-$.X$^+$ or —SO$_3$R$_3$, then R$_9$ and R$_{9'}$ are independently selected from —OH and —OR$_2$, wherein at least one of R$_9$ and R$_{9'}$ is a substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group.

In a particular embodiment, 2,5-dihydroxybenzene derivatives of the invention or any of the pharmaceutically acceptable salts thereof are those that are represented by Formula (I) comprising dobesilate esters derivatives or pharmaceutically acceptable salts or esters thereof for the treatment of arthritis or pain.

The X$^+$ cation in the Compounds of Formula (I''') may be any physiologically acceptable cation known by a skilled in the art and includes, but is not limited to, those described in Heinrich Stahl, Camille G. Wermuth (eds.), "Handbook of Pharmaceutical Salts Properties, Selections and Use", Verlag Helvetica Chimica Acta, Zurich, Switzerland, Wiley-VCH, Weinheim, Germany, 2002; the disclosures of which are incorporated herein by reference in their entirety. The X$^+$ cation is selected in such a way that the total charge of the compounds of Formula (I''') is neutral.

In a particular embodiment of the invention Y in the compound of formula (I''') is selected from –SO$_3$H, —SO$_3^-$.X$^+$ and —SO$_3$R$_3$.

In another particular embodiment, Z in the compound of formula (I''') is selected from —CO$_2$H, —CO$_2^-$.X$^+$ and —CO$_2$R$_3$.

In another particular embodiment, in the compound of formula (I''') at least one of R$_9$ and R$_{9'}$ are, independently, a substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group.

In another particular embodiment, R$_2$ is selected from methylcarbonyl, phenylsulfonyl, 4-methylphenylsulfonyl, benzylsulfonyl, benzyl and phenyl In another embodiment of the invention, R$_2$ is selected from acetyl (—C(O)CH$_3$), tosyl (—SO$_2$—C$_6$H$_4$—CH$_3$) and p-chlorophenoxyisobutyryl (—C(O)—C(CH$_3$)$_2$—O—C6H$_4$Cl).

In another embodiment, R$_3$ is selected from methyl, ethyl, isopropyl and C$_6$H$_5$—, more particularly from methyl and ethyl.

In one embodiment of the invention, the inorganic cation is sodium, potassium, lithium, calcium, or magnesium.

In another embodiment of the invention, the organic cation is [NH$_{4-p}$R$_p$]$^+$: wherein p is in each case selected independently from an integer number from 0 to 4, both included; and R is an alkyl group of one to six carbon atoms such as, for example, methyl, ethyl, n-propyl, i-propyl, n-butyl, t-butyl, or n-pentyl.

In another embodiment of the invention, the organic cations are a diethylamine [H$_2$N$^+$(C$_2$H$_5$)$_2$], piperazine or pyridine group.

In other embodiments of the invention, the compounds of Formula (I''') and pharmaceutically acceptable salts thereof are:

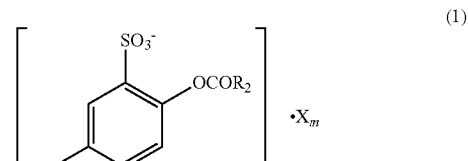
(1)

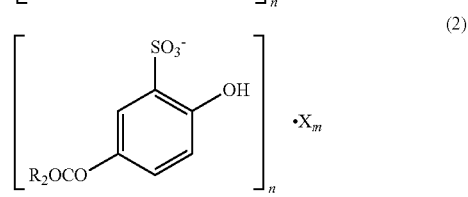
(2)

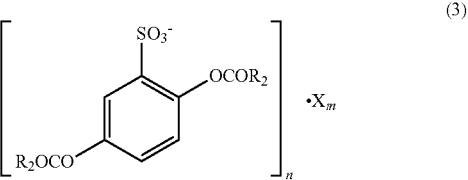
(3)

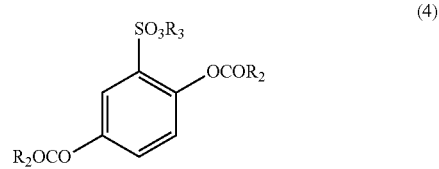
(4)

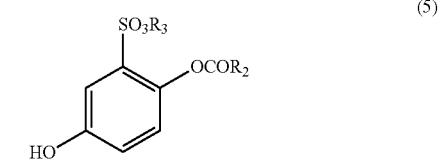
(5)

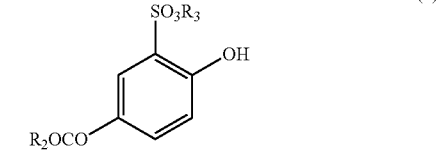
(6)

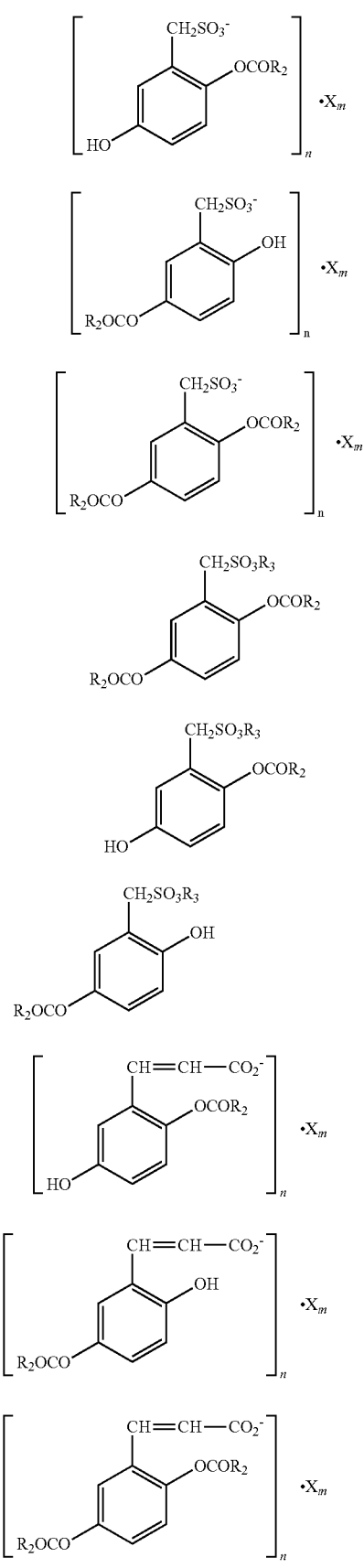

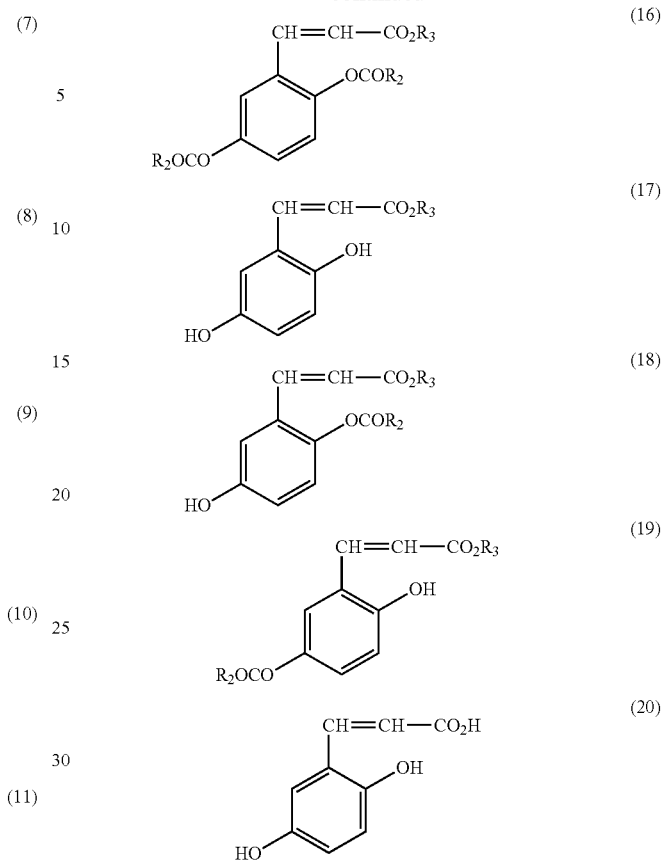

wherein:
n is an integer selected from 1 and 2;
m is an integer selected from 1 and 2; and
X, $R_2$ and $R_3$ are as defined herein.

In one preferred embodiment, the compound of Formula (I''') is selected from the group consisting of:
5-hydroxy-2-{[(4-methylphenyl)sulfonyl]oxy}benzenesulfonic acid;
2-hydroxy-5-{[(4-methylphenyl)sulfonyl]oxy}benzenesulfonic acid;
2,5-bis{[(4-methylphenyl)sulfonyl]oxy}benzenesulfonic acid;
2-(acetyloxy)-5-hydroxybenzenesulfonic acid;
5-(acetyloxy)-2-hydroxybenzenesulfonic acid;
2,5-bis(acetyloxy)benzenesulfonic acid;
5-hydroxy-2-{[(4-methylphenyl)sulfonyl]oxy}benzenehomosulfonic acid;
2-hydroxy-5-{[(4-methylphenyl)sulfonyl]oxy}benzenehomosulfonic acid;
2,5-bis{[(4-methylphenyl)sulfonyl]oxy}benzenehomosulfonic acid;
2-(acetyloxy)-5-hydroxybenzenehomosulfonic acid;
5-(acetyloxy)-2-hydroxybenzenehomosulfonic acid;
2,5-bis(acetyloxy)benzenehomosulfonic acid;
3-(2,5-dihydroxyphenyl)-2-propenoic acid (2,5-dihydroxycinnamic acid);
3-(5-hydroxy-2-{[(4-methylphenyl)sulfonyl]oxy}phenyl)-2-propenoic acid;
3-(2-hydroxy-5-{[(4-methylphenyl)sulfonyl]oxy}phenyl)-2-propenoic acid;
3-(2,5-bis{[(4-methylphenyl)sulfonyl]oxy}phenyl)-2-propenoic acid;

3-(2-(acetyloxy)-5-hydroxyphenyl)-2-propenoic acid;
3-(5-(acetyloxy)-2-hydroxyphenyl)-2-propenoic acid;
3-(2,5-bis(acetyloxy)phenyl)-2-propenoic acid;
3-(2-(benzyloxy)-5-hydroxyphenyl)-2-propenoic acid;
3-(5-(benzyloxy)-2-hydroxyphenyl)-2-propenoic acid;
3-(2,5-bis(benzyloxy)phenyl)-2-propenoic acid;
and pharmaceutically acceptable salts, solvates and prodrugs thereof.

In another particular embodiment, the compounds of Formula (I''') are in the form of esters at position 1, in particular methyl and ethyl esters.

Preferred compounds of formula (I''') are those selected from 2-(acetyloxy)-5-hydroxybenzenesulfonic acid; 5-(acetyloxy)-2-hydroxybenzenesulfonic acid and 2,5-bis(acetyloxy)benzenesulfonic acid.

In a particular embodiment, the arthritis is selected from osteoarthritis, rheumatoid arthritis, polyarthritis, gouty arthritis, lupus-related arthritis, psoriasis-related arthritis, infectious arthritis, including viral, parasitic and bacterial arthtritis.

The invention provides compositions comprising at least one compound of Formula (I''') and at least one additional therapeutic agent, including but not limited to a chemotherapeutic agent, a corticosteroid, an antibiotic, an analgesic, an alpha-adrenergic blocker, a beta-adrenergic agonist, an anticholinergic, an inhibitor of 5-alpha-reductase, an antiandrogen, an immunomodulator, an immunosuppressant, an anti-angiogenic such as anti VEGF, anti FGF, anti HGF and anti EFG; a leukotriene modifier, an aminosalicylate, an anesthetic, a non-steroidal anti-inflammatory, an antiparasitic, a therapy of the solubilized interleukin receptor, intramuscular gold, a cytotoxic, an antioxidant, and combinations of two or more thereof.

The compounds of Formula (I''') can optionally be used together with one or more additional therapeutic agents, such as a chemotherapeutic agent, a corticosteroid, an antibiotic, an analgesic, an alpha-adrenergic blocker, a beta-adrenergic agonist, an anticholinergic, an inhibitor of 5-alpha-reductase, an antiandrogen, an immunomodulator, an immunosuppressant, an anti-angiogenic such as anti VEGF, anti FGF, anti HGF and anti EFG; a leukotriene modifier, an aminosalicylate, an anesthetic, a non-steroidal anti-inflammatory, an antiparasitic, a therapy of the solubilized interleukin receptor, intramuscular gold, a cytotoxic, an antioxidant, and combinations of two or more thereof.

In a fifth aspect, the present invention relates to the use of a compound of Formula ($I^{IV}$) or pharmaceutically acceptable salt or solvate, isomer or prodrug thereof in the manufacturing of a medicament for the treatment and/or prophylaxis of any of the diseases selected from the group consisting of macular degeneration, corneal neovascularization or angiogenesis, iris neovascularization or angiogenesis, retinal neovascularization or angiogenesis, diabetic proliferative retinopathy and non-diabetic proliferative retinopathy, wherein the compound of Formula ($I^{IV}$):

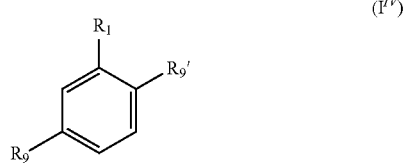

($I^{IV}$)

wherein:
$R_1$ is —$(CH_2)_a Y$ or —CH=CH—$(CH_2)_p Y$;
Y is —$SO_3H$, —$SO_3^-.X^+$, —$SO_3R_3$, —$PO_3H$, —$PO_3^-.X^+$, —$PO_3R_3$, —$CO_2^-.X^+$ or —$CO_2R_3$;

$X^+$ is an organic cation or an inorganic cation, such that the general charge of the compound is neutral;
$R_9$ and $R_{9'}$ are independently selected from —OH and —$OR_2$, wherein when $R_9$ and $R_{9'}$ are both —$OR_2$, then said $R_9$ and $R_{9'}$ can be the same or different;
$R_2$ is a substituted or unsubstituted alkyl group, a substituted or unsubstituted aryl group, a substituted or unsubstituted arylalkyl group, a substituted or unsubstituted alkylsulfonyl group, a substituted or unsubstituted arylsulfonyl group, a substituted or unsubstituted alkylarylsulfonyl group, a substituted or unsubstituted arylalkysulfonyl group, a substituted or unsubstituted aryloxyalkyl group, a substituted or unsubstituted alkylcarbonyl group or an arylcarbonyl group, a carboxyl group, a substituted or unsubstituted alkoxycarbonyl group, a substituted or unsubstituted carboxyalkyl group, in particular —$CH_2$—COOH, or a substituted or unsubstituted alkoxy- aryloxy- arylalkoxy- or alkylaryloxy-carbonylalkyl, in particular —$CH_2$—$COOR_3$;
$R_3$ is a substituted or unsubstituted alkyl group or a substituted or unsubstituted aryl group;
a is number selected from 0, 1, 2, 3, 4, 5 and 6;
p is an integer selected from 0, 1, 2, 3, 4, 5 and 6,
with the proviso that when Y is —$SO_3H$, or —$SO_3^-.X^+$ or —$SO_3R_3$, then $R_9$ and $R_{9'}$ are independently selected from —OH and —$OR_2$, wherein at least one of $R_9$ and $R_{9'}$ is a substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group.

In a particular embodiment, 2,5-dihydroxybenzene derivatives of the invention or any of the pharmaceutically acceptable salts thereof are those that are represented by Formula ($I^{IV}$) comprising dobesilate esters derivatives or pharmaceutically acceptable salts or esters thereof for the treatment of macular degeneration, corneal neovascularization or angiogenesis, iris neovascularization or angiogenesis, retinal neovascularization or angiogenesis, diabetic proliferative retinopathy and non-diabetic proliferative retinopathy.

The $X^+$ cation in the Compounds of Formula ($I^{IV}$) may be any physiologically acceptable cation known by a skilled in the art and includes, but is not limited to, those described in Heinrich Stahl, Camille G. Wermuth (eds.), "Handbook of Pharmaceutical Salts Properties, Selections and Use", Verlag Helvetica Chimica Acta, Zurich, Switzerland, Wiley-VCH, Weinheim, Germany, 2002; the disclosures of which are incorporated herein by reference in their entirety. The $X^+$ cation is selected in such a way that the total charge of the compounds of Formula ($I^{IV}$) is neutral.

In a particular embodiment of the invention, in the compound of formula ($I^{IV}$) Y is selected from –$SO_3H$, —$SO_3^-.X^+$, —$SO_3R_3$, —$CO_2H$, —$CO_2^-.X^+$ and —$CO_2R_3$.

In another particular embodiment, in the compound of formula ($I^{IV}$) at least one of $R_9$ and $R_{9'}$, are, independently, a substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group.

In another particular embodiment, $R_2$ is selected from methylcarbonyl, phenylsulfonyl, 4-methylphenylsulfonyl, benzylsulfonyl, benzyl and phenyl In another embodiment of the invention, $R_2$ is selected from acetyl (—$C(O)CH_3$), tosyl (—$SO_2$—$C_6H_4$—$CH_3$) and p-chlorophenoxyisobutyryl (—$C(O)$—$C(CH_3)_2$—O—$C6H_4Cl$).

In another embodiments, $R_3$ is selected from methyl, ethyl, isopropyl and $C_6H_5$—, more particularly from methyl and ethyl.

In one embodiment of the invention, the inorganic cation is sodium, potassium, lithium, calcium, or magnesium.

In another embodiment of the invention, the organic cation is $[NH_{4-p}R_p]^+$: wherein p is in each case selected independently from an integer number from 0 to 4, both included; and R is an alkyl group of one to six carbon atoms such as, for example, methyl, ethyl, n-propyl, i-propyl, n-butyl, t-butyl, or n-pentyl.

In another embodiment of the invention, the organic cations are a diethylamine $[H_2N^+(C_2H_5)_2]$, piperazine or pyridine group.

In other embodiments of the invention, the compounds of Formula ($I^{IV}$) and pharmaceutically acceptable salts thereof are:

(1)

(2)

(3)

(4)

(5)

(6)

(7)

-continued (8)

(9)

(10)

(11)

(12)

(13)

(14)

(15)

(16)

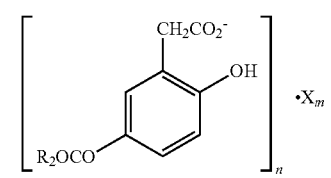 (17)
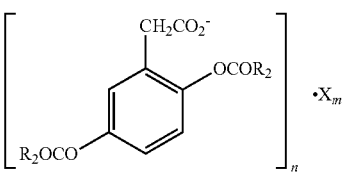 (18)
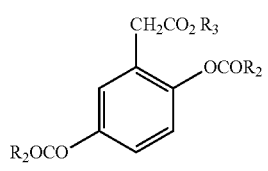 (19)
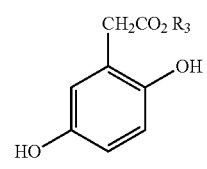 (20)
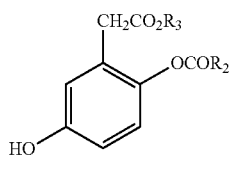 (21)
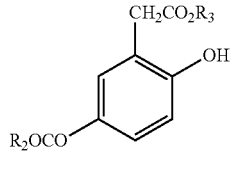 (22)
 (23)
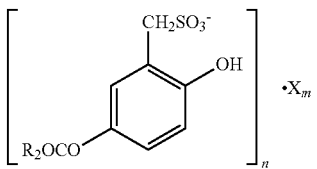 (24)
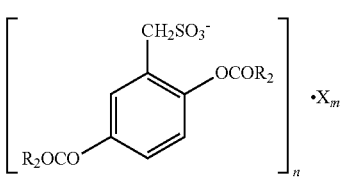 (25)
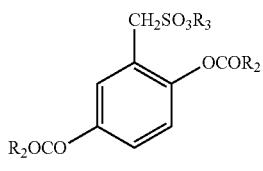 (26)
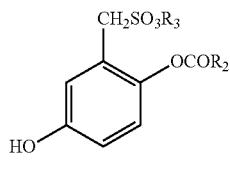 (27)
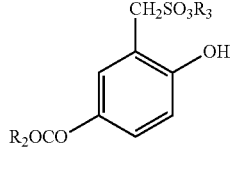 (28)
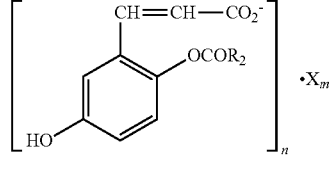 (29)
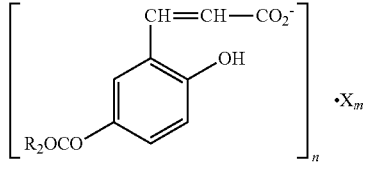 (30)
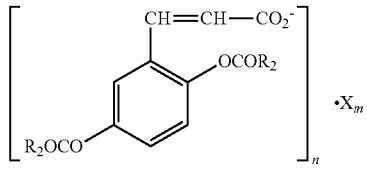 (31)
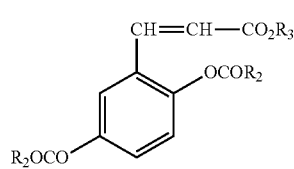 (32)
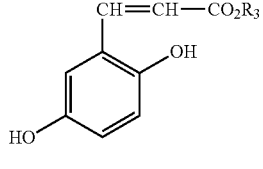 (33)
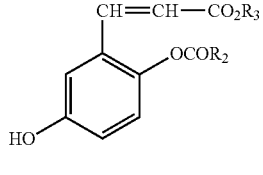 (34)

-continued

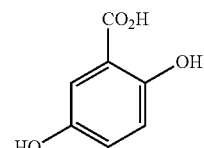  (35)

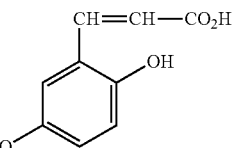  (36)

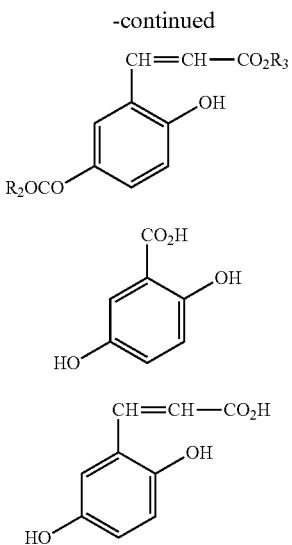  (37)

wherein:
n is an integer selected from 1 and 2;
m is an integer selected from 1 and 2; and
X, $R_2$ and $R_3$ are as defined herein.

In one preferred embodiment, the compound of Formula ($I^{IV}$) is selected from the group consisting of:
5-hydroxy-2-{[(4-methylphenyl)sulfonyl]oxy}benzenesulfonic acid;
2-hydroxy-5-{[(4-methylphenyl)sulfonyl]oxy}benzenesulfonic acid;
2,5-bis{[(4-methylphenyl)sulfonyl]oxy}benzenesulfonic acid;
2-(acetyloxy)-5-hydroxybenzenesulfonic acid;
5-(acetyloxy)-2-hydroxybenzenesulfonic acid;
2,5-bis(acetyloxy)benzenesulfonic acid.
5-hydroxy-2-{[(4-methylphenyl)sulfonyl]oxy}benzenehomosulfonic acid;
2-hydroxy-5-{[(4-methylphenyl)sulfonyl]oxy}benzenehomosulfonic acid;
2,5-bis{[(4-methylphenyl)sulfonyl]oxy}benzenehomosulfonic acid;
2-(acetyloxy)-5-hydroxybenzenehomosulfonic acid;
5-(acetyloxy)-2-hydroxybenzenehomosulfonic acid;
2,5-bis(acetyloxy)benzenehomosulfonic acid.
2,5-dihydroxybenzoic acid (gentisic acid),
5-hydroxy-2-{[(4-methylphenyl)sulfonyl]oxy}benzoic acid;
2-hydroxy-5-{[(4-methylphenyl)sulfonyl]oxy}benzoic acid;
2,5-bis{[(4-methylphenyl)sulfonyl]oxy}benzoic acid;
2-(acetyloxy)-5-hydroxybenzoic acid;
5-(acetyloxy)-2-hydroxybenzoic acid;
2,5-bis(acetyloxy)benzoic acid;
2-(benzyloxy)-5-hydroxybenzoic acid;
5-(benzyloxy)-2-hydroxybenzoic acid;
2,5-bis(benzyloxy)benzoic acid;
2,5-dihydroxyhomobenzoic acid (homogentisic acid),
5-hydroxy-2-{[(4-methylphenyl)sulfonyl]oxy}homobenzoic acid;
2-hydroxy-5-{[(4-methylphenyl)sulfonyl]oxy}homobenzoic acid;
2,5-bis{[(4-methylphenyl)sulfonyl]oxy}homobenzoic acid;
2-(acetyloxy)-5-hydroxyhomobenzoic acid;
5-(acetyloxy)-2-hydroxyhomobenzoic acid;
2,5-bis(acetyloxy) homobenzoic acid;
2-(benzyloxy)-5-hydroxyhomobenzoic acid;
5-(benzyloxy)-2-hydroxyhomobenzoic acid;
2,5-bis(benzyloxy) homobenzoic acid;
3-(2,5-dihydroxyphenyl)-2-propenoic acid (2,5-dihydroxycinnamic acid);
3-(5-hydroxy-2-{[(4-methylphenyl)sulfonyl]oxy}phenyl)-2-propenoic acid;
3-(2-hydroxy-5-{[(4-methylphenyl)sulfonyl]oxy}phenyl)-2-propenoic acid;
3-(2,5-bis{[(4-methylphenyl)sulfonyl]oxy}phenyl)-2-propenoic acid;
3-(2-(acetyloxy)-5-hydroxyphenyl)-2-propenoic acid;
3-(5-(acetyloxy)-2-hydroxyphenyl)-2-propenoic acid;
3-(2,5-bis(acetyloxy)phenyl)-2-propenoic acid;
3-(2-(benzyloxy)-5-hydroxyphenyl)-2-propenoic acid;
3-(5-(benzyloxy)-2-hydroxyphenyl)-2-propenoic acid;
3-(2,5-bis(benzyloxy)phenyl)-2-propenoic acid;
and pharmaceutically acceptable salts, solvates and prodrugs thereof.

In another particular embodiment, the compounds of Formula ($I^{IV}$) are in the form of esters at position 1, in particular methyl and ethyl esters.

Preferred compounds of formula ($I^{IV}$) are those selected from 2-(acetyloxy)-5-hydroxybenzenesulfonic acid; 5-(acetyloxy)-2-hydroxybenzenesulfonic acid and 2,5-bis(acetyloxy)benzenesulfonic acid.

The invention provides compositions comprising at least one compound of Formula ($I^{IV}$) and at least one additional therapeutic agent, including but not limited to a chemotherapeutic agent, a corticosteroid, an antibiotic, an analgesic, an alpha-adrenergic blocker, an alpha-adrenergic agonist, a beta-adrenergic agonist, an anticholinergic, an inhibitor of 5-alpha-reductase, an androgen, an immunomodulator, an immunosuppressant, an anti-angiogenic such as anti VEGF, anti FGF, anti HGF and anti EFG; a leukotriene modifier, an aminosalicylate, an anesthetic, a non-steroidal anti-inflammatory, an antiparasitic, a therapy of the solubilized interleukin receptor, a cytotoxic, an antioxidant and combinations of two or more thereof.

The compounds of Formula ($I^{IV}$) can optionally be used together with one or more additional therapeutic agents, such as a chemotherapeutic agent, a corticosteroid, an antibiotic, an analgesic, an alpha-adrenergic blocker, an alpha-adrenergic agonist, a beta-adrenergic agonist, an anticholinergic, an inhibitor of 5-alpha-reductase, an androgen, an immunomodulator, an immunosuppressant, an anti-angiogenic as anti VEGF, anti FGF, anti HGF and anti EFG; a leukotriene modifier, an aminosalicylate, an anesthetic, a non-steroidal anti-inflammatory, an antiparasitic, a therapy of the solubilized interleukin receptor, a cytotoxic, an antioxidant and combinations of two or more thereof.

The compounds of Formula (I), (I'), (I''), (I''') and ($I^{IV}$) may be synthesized by a skilled in the art using conventional or commercially available methods. The synthesis of the compounds of Formula (I), (I'), (I''), (I''') and ($I^{IV}$) is disclosed in, for example, U.S. Pat. No. 5,082,941; and "The Merck Index" 13th. edition, Merck & Co., R. Railway, NJ., USA, 2001; U.S. Pat. Nos. 5,082,841, 4,814,110, 4,613,332 and 4,115,648; the disclosures which are incorporated herein by reference in their entirety.

Compounds of Formula (I), (I'), (I''), (I''') and ($I^{IV}$) also may be in the form of solvates, particularly in the form of hydrates. The preparation of the compounds of Formula (I), (I'), (I''), (I''') and ($I^{IV}$), as well as the solvates thereof may be carried out by one skilled in the art using conventional methods and commercially available reagents.

Even if it has been previously mentioned in one of the preferred embodiments with respect to the definition of $X^+$ cation, the scope of the present invention encompasses any salt thereof, especially any pharmaceutically acceptable salt of the compound. The phrase "pharmaceutically acceptable salts" includes metal salts or the addition salts that may be used in pharmaceutical forms. For example, the pharmaceutically acceptable salts of the compounds provided herein may be acid addition salts, base addition salts or metal salts and they may be synthesized from the parenteral compounds containing a base or acid residue using conventional chemical processes. Generally, those salts are prepared, for example, by the reaction of free base or acid forms of these compounds with a stoichiometric amount of the appropriate base or acid in water or in an organic solvent, or in a mixture of both. Generally, non aqueous mediums such as ether, ethyl acetate, ethanol, isopropanol or acetonitrile are preferred. The examples of acid addition salts include addition salts of mineral acids such as, for example, hydrochloride, bromhydrate, iodide hydrate, sulfate, nitrate, phosphate, addition salts of organic acids such as, for example, acetate, maleate, fumarate, citrate, oxalate, succinate, tartrate, malate, mandelate, methanesulfonate and p-toluenesulfonate. The examples of alkali addition salts include inorganic salts such as, for example, ammonium salts and organic alkaline salts such as, for example, diethylamine, ethylenediamine, ethanolamine, N,N-dialkylenethanolamine, triethanolamine, glutamine and basic amino acid salts. The examples of metal salts include, for example, sodium, potassium, calcium, magnesium, aluminum, and lithium salts.

The term "pharmaceutically acceptable" refers to physiologically tolerable molecular entities and compositions which do not typically produce an allergic or similar adverse reaction, such as gastric upset, dizziness, and the like, when administered to a human. Preferably, as used herein, the term "pharmaceutically acceptable" means that it is approved by a regulatory agent of the Federal or a state government or listed in the U.S. Pharmacopeia or other generally recognized pharmacopoeia as suitable for use in animals, and more particularly, in humans.

It would be obvious to those skilled in the art that the scope of the present invention also encompasses salts that are not pharmaceutically acceptable as possible media to obtain pharmaceutically acceptable salts.

As used herein, the term "solvate" shall refer to any form of the active compound according to the invention that exhibits another molecule (most probably, a polar solvent) bound to it through a non-covalent bond. Examples of solvates include hydrates and alcoholates, preferably, $C_1$-$C_6$ alcoholates, for example, methanolate.

The pharmaceutically acceptable salts of Formula (I), (I'), (I''), (I''') and ($I^{IV}$) may be prepared from organic or inorganic acids or basis by conventional methods by the reaction of the appropriate acid or base with the compound.

In a particular embodiment of the invention, the 2,5-dihydroxybenzene derivatives of the invention may be optionally used in combinations with each other. In this manner and as an example, it is possible to combine the gentisic with the homogentisic or an ester of dobesilate ester with the homogentisic, and the like, in the same or in a different ratio. Said combinations may be in the same formulation or in formulations that would be used sequentially.

In some embodiments, the invention provides a composition comprising an ester derivative from those of Formula (I), (I'), (I''), (I''') or ($I^{IV}$), in particular a dobesilate ester derivatie, such as 2-acetyloxy-5-hydroxybenzenesulfonic acid, 5-acetyloxy-2-hydroxybenzenesulfonic acid, or 2,5-bis-acetyloxybenzenesulfonic acid. In some embodiments, it will be desirable to formulate a composition of the invention with an active principle such as a dobesilate ester derivative, for example, wherein the ester shows more therapeutic efficacy than the original compound in the treatment or prevention of a condition described herein. In other embodiments, the invention includes the use of a dobesilate ester derivative as a prodrug, for example, to treat a condition described herein, wherein the ester derivative is metabolized to the original compound in a patient to achieve therapeutic efficacy in the patient.

The compounds of Formulas (I), (I'), (I''), (I''') and ($I^{IV}$) also may be in the form of solvates, particularly in the form of hydrates. The preparation of the compounds of Formulas (I), (I'), (I''), (I''') and ($I^{IV}$) as well as their solvates may be synthesized by one skilled in the art using conventional methods and commercially available reagents. The 2,5-dihydroxybenzene compounds of Formulas (I), (I'), (I''), (I''') and ($I^{IV}$) are preferably formulated in the form of potassium, calcium, magnesium and ethylamine salts. The scope of the present invention encompasses any pharmaceutically acceptable salt of the compound. The phrase "pharmaceutically acceptable salts" includes metal salts or the addition salts that may be used in pharmaceutical forms. The pharmaceutically acceptable salts of 2,5-dihydroxybenzene compounds of Formulas (I), (I'), (I''), (I''') and ($I^{IV}$) may be prepared from organic or inorganic acids or bases by conventional methods by the reaction of the appropriate acid or base with the compound.

In the methods of the present invention, the compounds of Formulas (I), (I'), (I''), (I''') or ($I^{IV}$) may be used at a level from about 1 mg/kg of weight to about 200 mg/kg of weight without evidencing toxicity.

Corticosteroids include, but are not limited to, both topical (in creams, unguents, ointments, or gels) and systemic, intra-articular and inhaled, topical corticoids, such as, triamcinolone acetate, and the like, systemic corticoids, such as for example, prednisone, and the like.

Immunosuppresants and chemiotherapy agents include, but are not limited to, topical or systemic, such as, cyclosporine, methotrexate, azathioprine, leflunomide, and vincristine.

Immunomodulators including, but not limited to, Interferon alpha.

Leukotriene modifiers include, but are not limited to, for example, montelukast, zafirlukast, zileuton, cromolyn, nedocromil.

Aminosalicylates including, but not limited to, sulfasalazine, sulfapyridine, olsalazine, mesalamine, balsalazide; antihistamines, such as, diphenhydramine, hydroxizine, and the like.

Antiangiogenics such as bevacizumab.

Bismuth salts.

Proton pump inhibitors include, but are not limited to, omeprazole, lansoprazole, pantoprazole.

H2-receptor antagonists include, but are not limited to, cimetidine, ranitidine.

Anti-parasitic, such as hydrochloroquine.

Analgesics, such as, codeine, dihydrocodeine, morphine, oxycodone.

Antimicrobial compounds include, but are not limited to, macrolides, such as, for example, azithromycin, clarithromycin, dirithromycin, erythromycin, milbemycin, troleandomycin, and the like; monobactams, such as, for example, aztreonam, and the like; tetracyclines, such as, for example, demeclocycline, doxycycline, minocycline, oxytetracycline, tetracycline, and the like; aminoglycosides, such as, for example, amikacin, gentamicin, kanamycin, neomycin, netilmicin, paromomycin, streptomycin, tobramycin, and the like; carbacephems, such as, for example, loracarbef, and the like; carbapenems such as, for example, ertapenem, imipenem, meropenem, and the like; penicillins, such as, for example, amoxicillin, ampicillin, azlocillin, carbenicillin, cloxacillin, dicloxacillin, flucloxacillin, mezlocillin, nafcillin, penicillin, piperacillin, ticarcillin, and the like; polypeptides, such as, for example, bacitracin, colistin, polymyxin B, and the like; beta-lactamase inhibitors; cephalosporins, such as, for example, cefaclor, cefamandol, cefoxitin, cefprozil, cefuroxime, cefixime, cefdinir, cefditoren, cefoperazone, cefotaxime, cefpodoxime, cefadroxil, ceftazidime, ceftibuten, ceftizoxime, ceftriaxone, cefazolin, cefixime, cefalexin, cefepime, and the like; quinolones, such as, for example, ciprofloxacin, enoxacin, gatifloxacin, levofloxacin, lomefloxacin, moxifloxacin, norfloxacin, ofloxacin, trovafloxacin, and the like; streptogramins; sulfonamides, such as, for example, mefanide, prontosil, sulfacetamide, sulfamethizole, sulfanilamide, sulfasalazine, sulfisoxazole, trimethoprim, trimethoprim-sultamethoxazole, and the like; and the combination drugs such as for example, sulfamethoxazole and trimethoprim, and the like. Suitable antimicrobial compounds of the invention are described more fully in the literature, such as in Goodman and Gilman, The Pharmacological Basis of Therapeutics (9th Edition), McGraw-Hill, (1996); Merck Index on CD-ROM, 13th Edition; STN Express, file phar and file registry, the disclosures of each of which are incorporated by reference herein in their entirety.

Suitable non-steroidal anti-inflammatory drugs (NSAIDs) include, but are not limited to, acetaminophen, acemetacin, aceclofenac, alminoprofen, amfenac, bendazac, benoxaprofen, bromfenac, bucloxic acid, butibufen, carprofen, cinmetacin, clopirac, diclofenac, etodolac, felbinac, fenclozic acid, fenbufen, fenoprofen, fentiazac, flunoxaprofen, flurbiprofen, ibufenac, ibuprofen, indomethacin, isofezolac, isoxepac, indoprofen, ketoprofen, lonazolac, loxoprofen, metiazinic acid, mofezolac, miroprofen, naproxen, oxaprozin, pirozolac, pirprofen, pranoprofen, protizinic acid, salicylamide, sulindac, suprofen, suxibuzone, tiaprofenic acid, tolmetin, xenbucin, ximoprofen, zaltoprofen, zomepirac, aspirin, acemetcin, bumadizon, clidanac, diflunisal, enfenamic acid, fendosal, flufenamic acid, flunixin, gentisic acid, ketorolac, meclofenamic acid, mefenamic acid, mesalamine, prodrugs thereof, and the like. Suitable NSAIDs are described more fully in literature, such as in Goodman and Gilman, The Pharmacological Basis of Therapeutics (9th Edition), McGraw-Hill, 1995, pgs. 617-657; the Merck Index on CD-ROM, (13$^{th}$ Edition); and in U.S. Pat. Nos. 6,057,347 and 6,297,260 assigned to NitroMed. Inc., the disclosures of which are incorporated herein by reference in their entirety.

In some embodiments the NSAIDs are acetaminophen, diclofenac, flurbiprofen, ibuprofen, indomethacin, ketoprofen, naproxen or aspirin.

Suitable topical anesthetics include, but are not limited to lidocaine.

Thus, another aspect of the present invention refers to a method for the treatment and/or prophylaxis of a disease selected from hemangiomas and hemangioblastomas, comprising administering to a subject in need thereof an effective amount of a 2,5-dihydroxybenzene derivative represented by Formula (I) or a pharmaceutically acceptable salt or solvate thereof, isomer or prodrug thereof. For example, the patient may be administered with an effective amount of, at least, one 2,5-dihydroxybenzene compound of Formula (I).

In a particular embodiment, the patient may be administered an effective amount of, at least, one 2,5-dihydroxybenzene compound of Formula (I) and at least one additional therapeutic agent, including, but not limited to, a chemotherapeutic agent, a corticosteroid, an antibiotic, an analgesic, an antiandrogen, an immunomodulator, an anti-angiogenic, including anti-VEGF, anti-FGF, anti-EGF and anti-HGF; inhibitors of tyrosin-kinase receptors, protein kinase C inhibitors, a non-steroidal anti-inflammatory, a therapy of the solubilized interleukin receptor, a cytotoxic, an antioxidant and combinations of two or more thereof 2,5-dihydroxybenzene compounds and/or additional therapeutic agents may be administered separately or as components of the same composition in one or more pharmaceutically acceptable vehicles.

In another embodiment, the invention refers to a method for the treatment and/or prophylaxis of any of the diseases selected from the group consisting of benign prostatic hyperplasia, Barrett's disease, asthma, skeletal muscle and tendon repair, Crohn's disease, ulcerative colitis and leishmaniasis, comprising administering to a subject in need thereof an effective amount of a 2,5-dihydroxybenzene derivative represented by Formula (I') or a pharmaceutically acceptable salt or solvate thereof, isomer or prodrug thereof.

In a particular embodiment, the patient may be administered an effective amount of, at least, one 2,5-dihydroxybenzene compound of Formula (I') and at least one additional therapeutic agent, including, but not limited to, a chemotherapeutic agent, a corticosteroid, an antibiotic, an analgesic, an alpha-adrenergic blocker, a beta-adrenergic agonist, an anticholinergic, an inhibitor of 5-alpha-reductase, an antiandrogen, an oral contraceptive, an immunomodulator, an immunosuppressant, an anti-angiogenic, a bronchodilator, a leukotriene modifier, an aminosalicylate, an anesthetic, a non-steroidal anti-inflammatory, an antiparasitic, a proton pump inhibitor, an H2-receptor antagonist, a therapy of the solubilized interleukin receptor, intramuscular gold, a cytotoxic, an antioxidant and combinations of two or more thereof 2,5-dihydroxybenzene compounds and/or additional therapeutic agents may be administered separately or as components of the same composition in one or more pharmaceutically acceptable vehicles.

In another embodiment, the invention refers to a method for the treatment and/or prophylaxis of any of the diseases selected from the group consisting of diseases associated to *Helicobacter pylori* infection, pterygium, endometrosis, ovarian hyperstimulation syndrome and polycystic kidney disease, comprising administering to a subject in need thereof an effective amount of a 2,5-dihydroxybenzene derivative represented by Formula (I") or a pharmaceutically acceptable salt or solvate thereof, isomer or prodrug thereof.

In a particular embodiment, the patient may be administered an effective amount of, at least, one 2,5-dihydroxybenzene compound of Formula (I") and at least one additional therapeutic agent, including, but not limited to, a chemotherapeutic agent, a corticosteroid, an antibiotic, an analgesic, an alpha-adrenergic blocker, a beta-adrenergic agonist, an anticholinergic, an inhibitor of 5-alpha-reductase, an antiandrogen, an oral contraceptive, an immunomodulator, an immunosuppressant, an anti-angiogenic, a bronchodilator, a leukotriene modifier, an aminosalicylate, an anesthetic, a non-steroidal anti-inflammatory, an antiparasitic, a proton pump inhibitor, an H2-receptor antagonist, a therapy of the solubilized interleukin receptor, intramuscular gold, a cytotoxic, an antioxidant and combinations of two or more thereof 2,5-dihydroxybenzene compounds and/or additional therapeutic agents may be administered separately or as components of the same composition in one or more pharmaceutically acceptable vehicles.

In another embodiment, the invention refers to a method for the treatment and/or prophylaxis of arthritis or pain, comprising administering to a subject in need thereof an effective amount of a 2,5-dihydroxybenzene derivative represented by Formula (I''') or a pharmaceutically acceptable salt or solvate thereof, isomer or prodrug thereof.

In a particular embodiment, the patient may be administered an effective amount of, at least, one 2,5-dihydroxybenzene compound of Formula (I''') and at least one additional therapeutic agent, including, but not limited to, a chemotherapeutic agent, a corticosteroid, an antibiotic, an analgesic, an alpha-adrenergic blocker, a beta-adrenergic agonist, an anticholinergic, an inhibitor of 5-alpha-reductase, an antiandrogen, an immunomodulator, an immunosuppressant, an anti-angiogenic such as anti VEGF, anti FGF, anti HGF and anti EFG; a leukotriene modifier, an aminosalicylate, an anesthetic, a non-steroidal anti-inflammatory, an antiparasitic, a therapy of the solubilized interleukin receptor, intramuscular gold, a cytotoxic, an antioxidant, and combinations of two or more thereof 2,5-dihydroxybenzene compounds and/or additional therapeutic agents may be administered separately or as components of the same composition in one or more pharmaceutically acceptable vehicles.

In another embodiment, the invention refers to a method for the treatment and/or prophylaxis of any of the diseases selected from the group consisting of macular degeneration, corneal neovascularization or angiogenesis, iris neovascularization or angiogenesis, retinal neovascularization or angiogenesis, diabetic proliferative retinopathy and non-diabetic proliferative retinopathy, comprising administering to a subject in need thereof an effective amount of a 2,5-dihydroxybenzene derivative represented by Formula ($I^{IV}$) or a pharmaceutically acceptable salt or solvate thereof, isomer or prodrug thereof.

In a particular embodiment, the patient may be administered an effective amount of, at least, one 2,5-dihydroxybenzene compound of Formula ($I^{IV}$) and at least one additional therapeutic agent, including, but not limited to, a chemotherapeutic agent, a corticosteroid, an antibiotic, an analgesic, an alpha-adrenergic blocker, an alpha-adrenergic agonist, a beta-adrenergic agonist, an anticholinergic, an inhibitor of 5-alpha-reductase, an androgen, an immunomodulator, an immunosuppressant, an anti-angiogenic such as anti VEGF, anti FGF, anti HGF and anti EFG; a leukotriene modifier, an aminosalicylate, an anesthetic, a non-steroidal anti-inflammatory, an antiparasitic, a therapy of the solubilized interleukin receptor, a cytotoxic, an antioxidant and combinations of two or more thereof. 2,5-dihydroxybenzene compounds and/or additional therapeutic agents may be administered separately or as components of the same composition in one or more pharmaceutically acceptable vehicles.

When administered separately, the 2,5-dihydroxybenzene compounds of Formulas (I), (I'), (I''), (I''') or ($I^{IV}$) may be administered approximately at the same time as part of the whole treatment regime, that is to say as a combination therapy. The expression "approximately at the same time" includes the administration of the 2,5-dihydroxybenzene compound simultaneously, sequentially, at the same moment, in different moments during the same day, on different days, as long as it is administered as part of a whole treatment regime, that is to say, a combination therapy or a therapeutic cocktail.

When administered alone, the compounds and compositions of the present invention may be administered in combination with pharmaceutically accepted vehicles and in the dosages described herein. When the compounds and compositions of the invention are administered as a combination of, at least, one 2,5-dihydroxybenzene compound of Formulas (I), (I'), (I''), (I''') or ($I^{IV}$) and/or, at least, one additional therapeutic agent, a combination with one or more additional compounds known to be effective for the specific pathology established as an objective for the treatment may be used. Different additional therapeutic agents and/or compounds may be administered simultaneously with, after, or before administering the 2,5-dihydroxybenzene compound.

The pharmaceutical compositions containing the formulas of the invention may be presented in any suitable form of administration, for example, for systemic, transdermal, oral, buccal, parenteral, topical, rectal, intravaginal administration or by inhalation; therefore, they shall include the acceptable pharmaceutical excipients necessary to formulate the desired form of administration.

The compositions comprise an effective amount of 2,5-dihydroxibenzene compounds of Formulas (I), (I'), (I''), (I''') or ($I^{IV}$), from about 0.001 and about 30%. Furthermore, the composition comprises a pharmaceutical acceptable vehicle.

Generally, the vehicle is organic and may contain the 2,5-dihydroxybenzene compounds of Formulas (I), (I'), (I''), (I''') or ($I^{IV}$) diluted or dispersed. Lotions, creams, solutions, gels and solids are the usual physical forms of the composition.

The subject treated with the drug of the invention is an animal, preferably a mammal and more specifically a human. The main object of the present invention is directed to the treatment or prevention of the described diseases, mainly in humans. Secondarily, the present invention may be used for the treatment or prevention of said diseases in pets and farm animals, not limited to, bovine, equine and porcine.

The medicament of the present invention may be administered by any of the routes conventionally used to administer drugs. Such routes include, but are not limited, to topical, oral, buccal, parenteral, inhalatory, rectal intravaginal, intraocular and transdermal administration for the treatment of hemangiomas or hemangioblastomas; topical, oral, buccal, transdermal, parenteral or rectal route for the treatment of diseases selected from the group consisting of benign prostatic hyperplasia, Barrett's disease, asthma, skeletal muscle and tendon repair, Crohn's disease, ulcerative colitis and leishmaniasis; topical, transdermal, oral, buccal, parenteral, intradermal, by inhalation, rectal, intravaginal or intraocular route for the treatment of diseases associated to *Helicobacter pylori* infection, pterygium, endometrosis, ovarian hyperstimulation syndrome and polycystic kidney disease; topical, transdermal, oral, buccal, parenteral, by inhalation, rectal, intravaginal, intraocular, otical or intraarticular route for the treatment of arthritis or pain; topical, oral, intradermal, parenteral or intraocular route for the treatment of any of the diseases selected from the group consisting of macular degeneration, corneal neovascularization or angiogenesis, iris neovascularization or angiogenesis, retinal neovascularization or angiogenesis, diabetic proliferative retinopathy and non-diabetic proliferative retinopathy.

The parenteral route of administration may be intraperitoneal, intravenous, intraarterial, perioral, subcutaneous, intramuscular, etc.

The compositions of the invention may be administered in the conventional dosage forms prepared by the combination of pharmacologically standardized "carriers". These combinations involve procedures such as mixing, granulation, compression, and dissolution in suitable ingredients. The form and nature of the pharmacologically acceptable carrier is related to the active ingredient with which it is mixed and with the route of administration.

The term "carrier", as used herein, refers to the diluents and excipients used to prepare the pharmaceutical composition. The term "pharmacologically acceptable" refers to the requirements described in the Pharmacopoeia related to the manufacture and use of drugs in animals, and especially in humans.

The pharmacologically acceptable carriers may be liquid or solid. The compositions of the invention may be administered orally. For this purpose, the pharmaceutical composition may be prepared in liquid form, such as solutions, syrups or suspensions or may be formulated as a product to be reconstituted with water or other vehicles before administration. Liquid formulations may be prepared using conventional means with pharmacologically acceptable additives such as suspension agents (sorbitol), non-aqueous vehicles (oil or ether), emulsifying agents (lecithin) and preservatives (sorbic acid). The pharmaceutical composition may be in the form of tablets, capsules or aggregates prepared using conventional methods with pharmacologically acceptable excipients such as binding agents (polyvinyl, pyrrolidone or hydroxypropyl cellulose), extenders (lactose or microcrystalline cellulose), lubricants (magnesium stearate or talc); disintegrators (potato starch) or wetting agents (sodium lauryl sulfate). Tablets may be coated using pharmaceutically acceptable methods.

Compositions for oral or bucal administration may be formulated such that they have a controlled release of the active compound. Said formulations may include one or several agents of continuous release such as glycerol monostearate, glycerol distearate and wax.

Pharmaceutical compositions containing the active principle of the invention may be also applied topically on the epidermis, in the oral cavity, in the eye, in the ear, in the nasal cavity or in the urethral, vaginal or rectal mucosa. Compositions for use in topical administration include liquid or gel preparations for application on the skin, such as creams, ointments, liniments or pastes and drops suitable for delivery to the eye, ear or nose. According to the invention, creams, drops, liniments, lotions, ointments and pastes are liquid or semi-solid compositions for external application. These formulations may be prepared by mixing the active principle in powdered form, alone or in solution or suspension in an aqueous or non-aqueous fluid with a greasy or non-greasy base. The base may comprise complex carbohydrates such as glycerol, various forms of paraffin, beeswax; a mucilage, a mineral or edible oil or fatty acids; or a macrogel. Formulations may additionally comprise suitable emulsifying agents such as surfactants, and suspending agents such as agar, vegetable gums, cellulose derivatives, and other ingredients such as preservatives, antioxidants, etc.

According to the invention, lotions and drops include those suitable to be applied on the skin or delivered to the eye. Eye lotions and drops may be formulated in sterile aqueous solution; oily solutions or suspensions may be prepared by diluting the active principle in a suitable aqueous solution. Such solutions may optionally contain a suitable bactericide, fungicide, preservative and surfactant. Lotions and liniments for application on the skin may also contain dehydrating agents such as alcohol and/or wetting agents such as glycerol, an oil or a fatty acid.

The formulations of the invention also can be administered nasally or by inhalation. For nasal or inhalation administration, the formulations are conveniently delivered in the form of an aerosol spray in pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to release a specific amount. Capsules and cartridges of, for example, gelatin for use in an inhaler may be formulated containing a powder mix of the compound and a suitable powder base such as lactose or starch.

The compounds of the invention may be also formulated for a delayed release. Such long acting formulations may be administered by implantation (for example, subcutaneously or intramuscularly) or by an intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

In a particular embodiment of the invention, the compounds of formula (I), (I'), (I''), (I''') or ($I^{IV}$) are administered at least once per week, more preferably at least once per day, even more preferably twice per day. In another particular embodiment, the compound of formula (I), (I'), (I''), (I''') or ($I^{IV}$) are administered over a period of at least about one week, more preferably over a period of at least about four weeks.

The duration of treatment will typically depend on the particular condition, its severity, the condition of the patient, and the like, and will readily be determined by one of skill in the art. Illustrative courses of therapy include 1 week, 2 weeks, 3 weeks, 4 weeks, 5 weeks, 6 weeks, 7 weeks, 8 weeks, 9 weeks, 10 weeks, 11 weeks, 12 weeks, 3.5 months, 4 months, 4.5 months, 5 months, 6 months, 9 months, a year, or longer as needed.

In treating a subject suffering from a disorder described herein, treatment may be continued until at least a 10% improvement is effected in a symptom associated with the condition. In other embodiments, treatment is continued until the subject in need of such treatment experiences an improvement of at least about 20%, at least about 30%, at least about 40%, preferably at least about 50%, preferably at least about 60%, more preferably at least about 70%, more preferably at least about 80%, even more preferably 90% or greater in a symptom associated with a disorder described herein.

In a particular embodiment of the invention, a compound of formula (I), (I'), (I''), (I''') or ($I^{IV}$) is administered at least once per week. In other embodiments, a compound of formula (I), (I'), (I''), (I''') or ($I^{IV}$) is administered at least once per day. In yet other embodiments, a compound of formula (I), (I'), (I''), (I''') or ($I^{IV}$) is administered twice per day. In another particular embodiment, a compound of formula (I), (I'), (I''), (I''') or ($I^{IV}$) is administered over a period of at least about one week. In other embodiments, a compound of formula (I), (I'), (I''), (I''') or ($I^{IV}$) is administered over a period of at least about four weeks.

Therapeutic amounts can be empirically determined and will vary with the particular condition being treated, the subject, the particular formulation components, dosage form, and the like.

In a particular embodiment, a compound of formula (I), (I'), (I''), (I''') or ($I^{IV}$) is present in a pharmaceutical composition in an amount of at least about 1% w/w. In other embodiments, a compound of formula (I), (I'), (I''), (I''') or ($I^{IV}$) is present in a pharmaceutical composition in an amount of at least about 2.5% w/w, at least about 5% w/w, at least about 10% w/w, or at least about 15% w/w.

In one embodiment, the 2,5-dihydroxybenzene compounds of Formulas (I), (I'), (I''), (I''') or ($I^{IV}$) may be administered in an amount of about 0.05 g per day to about 50 g per day. In particular embodiments, the 2,5-dihydroxybenzene compounds of Formulas (I), (I'), (I''), (I''') or ($I^{IV}$) may be administered in an amount of about 0.10 g per day to about 25 g per day. In more particular embodiments, the 2,5-dihydroxybenzene compounds of Formulas (I), (I'), (I''), (I''') or ($I^{IV}$) may be administered in an amount of about 0.25 g per day to about 10 g per day. In a more particular embodiment, the 2,5-dihydroxybenzene compounds of Formulas (I), (I'), (I"), (I'") or (I$^{IV}$) may be administered in an amount of about 0.5 g per day to about 5 g pr day. In an even more particular embodiment, the 2,5-dihydroxybenzene compounds of Formulas (I), (I'), (I"), (I'") or (I$^{IV}$) may be administered in an amount of about 0.75 g per day to about 2.5 g per day. In another particular embodiment, the 2,5-dihydroxybenzene compounds of Formulas (I), (I'), (I"), (I'") or (I$^{IV}$) may be administered in an amount of about 1 g per day to about 1.5 g per day. The particular amounts of the 2,5-dihydroxybenzene compounds of Formulas (I), (I'), (I"), (I'") or (I$^{IV}$) may be administered as a single dose once a day; or in multiple doses several times a day; or as a sustained-release oral formulation. In one embodiment of the invention, the 2,5-dihydroxybenzene compounds of Formulas (I), (I'), (I"), (I'") or (I$^{IV}$) are administered as about 50 g, 25 g, 10 g, 5 g, 1 g, 0.75 g, 0.5 g, 0.25 g or 0.1 g once per day (q.d). In another embodiment of the invention, the 2,5-dihydroxybenzene compounds of Formulas (I), (I'), (I"), (I'") or (I$^{IV}$) are administered as about 50 g, 25 g, 10 g, 5 g, 1 g, 0.75 g, 0.5 g, 0.25 g or 0.1 g twice per day (b.i.d.) In another embodiment of the invention, the 2,5-dihydroxybenzene compounds of Formulas (I), (I'), (I"), (I'") or (I$^{IV}$) are administered as about 50 g, 25 g, 10 g, 5 g, 1 g, 0.75 g, 0.5 g, 0.25 g or 0.1 g three times per day (t.i.d.) In another embodiment of the invention, the 2,5-dihydroxybenzene compounds of Formulas (I), (I'), (I"), (I'") or (I$^{IV}$) are administered as about 50 g, 25 g, 10 g, 5 g, 1 g, 0.75 g, 0.5 g, 0.25 g or 0.1 g four times per day.

In particular embodiments, the 2,5-dihydroxybenzene compounds of Formulas (I), (I'), (I"), (I'") or (I$^{IV}$) may be administered topically in a formulation comprising an amount of about 0.001% to about 30% (w/w) of the 2,5-dihydroxybenzene compounds of Formulas (I), (I'), (I"), (I'") or (I$^{IV}$). In a more particular embodiment, the 2,5-dihydroxybenzene compounds of Formulas (I), (I'), (I"), (I'") or (I$^{IV}$) may be administered topically in a formulation comprising an amount of about 0.01% to about 20% (w/w) of the 2,5-dihydroxybenzene compounds of Formulas (I), (I'), (I"), (I'") or (I$^{IV}$). In an even more particular embodiment, the 2,5-dihydroxybenzene compounds of Formula (I), (I'), (I"), (I'") or (I$^{IV}$) may be administered topically in a formulation comprising an amount of about 0.1% to about 15% (w/w) of the 2,5-dihydroxybenzene compounds of Formulas (I), (I'), (I"), (I'") or (I$^{IV}$). In a more particular embodiment, the 2,5-dihydroxybenzene compounds of Formula (I) may be administered topically in a formulation comprising an amount of about 0.5% to about 10% (w/w) of the 2,5-dihydroxybenzene compounds of Formulas (I), (I'), (I"), (I'") or (I$^{IV}$). In another particular embodiment, the 2,5-dihydroxybenzene compounds of Formulas (I), (I'), (I"), (I'") or (I$^{IV}$) may be administered topically in a formulation comprising an amount of about 1% to about 5% (w/w) of the 2,5-dihydroxybenzene compounds of Formulas (I), (I'), (I"), (I'") or (I$^{IV}$). In an even more particular embodiment, the 2,5-dihydroxybenzene compounds of Formula (I), (I'), (I"), (I'") or (I$^{IV}$) may be administered topically in a formulation comprising an amount of about 2.5% to about 4% (w/w) of the 2,5-dihydroxybenzene compounds of Formulas (I), (I'), (I"), (I'") or (I$^{IV}$). The topical formulation comprising the 2,5-dihydroxybenzene compounds of Formula (I) may be administered as a single dose once a day; or in multiple doses several times throughout the day. In one embodiment of the invention, the topical formulation comprises about 30%, 20%, 15%, 10%, 5%, 2.5%, 1%, 0.5%, 0.1% or 0.001% of the 2,5-dihydroxybenzene compound of Formulas (I), (I'), (I"), (I'") or (I$^{IV}$) is administered four times per day. In another embodiment of the invention, the topical formulation comprising about 30%, 20%, 15%, 10%, 5%, 2.5%, 1%, 0.5%, 0.1% or 0.001% of the 2,5-dihydroxybenzene compounds of Formulas (I), (I'), (I"), (I'") or (I$^{IV}$) is administered three times per day (t.i.d). In yet another embodiment of the invention, the topical formulation comprising about 30%, 20%, 15%, 10%, 5%, 2.5%, 1%, 0.5%, 0.1% or 0.001% of the 2,5-dihydroxybenzene compounds of Formulas (I), (I'), (I"), (I'") or (I$^{IV}$) is administered two times per day (b.i.d). In another embodiment of the invention, the topical formulation comprising about 30%, 20%, 15%, 10%, 5%, 2.5%, 1%, 0.5%, 0.1% or 0.001% of the 2,5-dihydroxybenzene compounds of Formulas (I), (I'), (I"), (I'") or (I$^{IV}$) is administered once per day (q.d.).

In yet other embodiments, the invention provides a kit or package comprising a compound of formula (I), (I'), (I"), (I'") or (I$^{IV}$), in packaged form, accompanied by instructions for use. The compound of formula (I), (I'), (I"), (I'") or (I$^{IV}$) may be packaged in any manner suitable for administration, so long as the packaging, when considered along with the instructions for administration, indicates the manner in which the compound of formula (I), (I'), (I"), (I'") or (I$^{IV}$) is to be admininistered.

For example, a kit may comprise a compound of formula (I), (I'), (I"), (I'") or (I$^{IV}$) in unit dosage form, along with instructions for use. For example, such instructions may indicate that administration of a compound of formula (I), (I'), (I"), (I') or (I$^{IV}$) is useful in the treatment of pain and/or arthritis. The compound of formula (I), (I'), (I"), (I'") or (I$^{IV}$) may be packaged in any manner suitable for administration. For example, when the compound of formula (I), (I'), (I"), (I'") or (I$^{IV}$) is in oral dosage form, e.g., is in the form of a coated tablet, then the kit may comprise a sealed container of coated tablets, blister strips containing the tablets, or the like.

Various embodiments according to the above may be readily envisioned, and would depend upon the particular dosage form, recommended dosage, intended patient population, and the like. The packaging may be in any form commonly employed for the packaging of pharmaceuticals, and may utilize any of a number of features such as different colors, wrapping, tamper-resistant packaging, blister packs or strips, and the like.

The following non-limiting examples further describe and enable one of ordinary skill in the art to make and use the present invention.

EXAMPLES OF THE INVENTION

Example 1

Preparation of Lotions

Lotions comprise from about 0.001% to about 30% of the compounds of Formula I, from 1% to 25% of an emollient and the suitable amount of water. Examples of emollients are:
I. Hydrocarbon waxes and oils. Such as mineral oil, petrolatum, paraffin, ceresin, microcrystalline wax, polyethylene and perhydrosqualene.
II. Silicone oils such as dimethyl polysiloxanes, methylphenyl polysiloxanes and water-soluble and alcohol-soluble silicone glycol copolymers.
III. Triglycerides, such as animal and vegetable fats and oils. Examples include, but are not limited to, castor oil, cod liver oil, corn oil, olive oil, almond oil, palm oil, sesame oil, cotton seed oil and soybean oil.
IV. Acetoglyceride esters, such as acetylated monoglycerides.

V. Ethoxylated glycerides, such as ethoxylated glycerol monostearate.
VI. Alkyl esters of fatty acids having 10 to 20 carbon atoms. Methyl, isopropyl and butyl esters of fatty acids are useful herein. Examples include, but are not limited to, hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristoyl lactate and cetyl lactate.
VII. Alkenyl esters of fatty acids having 10 to 20 carbon atoms. Examples thereof include, but are not limited to, oleyl myristate, oleyl stearate and oleyl oleate.
VIII. Fatty acids having 10 to 20 carbon atoms. Suitable examples include, but are not limited to, pelargonic, lauric, myristic, palmitic, stearic, isostearic, hydroxystearic, oleic, linoleic, ricinoleic, arachidonic, behenic and erucic acids.
IX. Fatty alcohols having 10 to 20 carbon atoms. Lauryl, myristoyl, palmitoyl, stearyl, isostearyl, hydroxystearyl, oleyl, ricinoleyl, behenyl, erucyl and 2-octyl dodecanol alcohols are appropriate examples of fatty alcohols.
X. Fatty alcohol ethers. Ethoxylated fatty alcohols having 10 to 20 carbon atoms include, but are not limited to, lauryl, cetyl, stearyl, isostearyl, oleyl and cholesterol alcohols having attached thereto from 1 to 50 ethylene oxide groups or 1 to 50 propylene oxide groups.
XI. Ether-esters, such as fatty acid esters of ethoxylated fatty alcohols.
XII. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleates, lanolin alcohols ricinoleate, acetate of lanolin alcohols ricinoleate, hydrogenolysis of lanolin, and liquid or semisolid lanolin absorption bases are illustrative examples of lanolin derived emollients.
XIII. Polyhydric alcohols and polyether derivatives. Propylene glycol, dipropylene glycol, polypropylene glycol 2000 and 4000, polyoxyethylene polypropylene glycols, glycerol, ethoxylated glycerol, propoxylated glycerol, sorbitol, ethoxylated sorbitol, hydroxypropyl sorbitol, polyethylene glycol 200-6000, methoxy polyethylene glycols 350, 550, 750, 2000, 5000, poly (ethylene oxide) homopolymers (100,000-5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol), and polyoxypropylene derivatives of trimethylolpropane are suitable examples.
XIV. Polyhydric alcohol esters. Mono- and di-acyl esters of ethylene glycol, mono- and di-acyl esters of diethylene glycol, mono- and di-acyl esters of polyethylene glycol (200-6000), mono- and di-acyl esters of propylene glycol, polypropylene glycol 2000 monooleate, polypropylene glycol 2000 monostearate, ethoxylated propylene glycol monostearate, mono- and di-acyl esters of glycerol, poly-acyl esters of poly glycerol, ethoxylated glycerol monostearate, 1,3-butylene glycol monostearate, 1,3-butylene glycol distearate, acyl ester of polyoxyethylene polyol, acyl esters of sorbitan, and acyl esters of polyoxyethylene sorbitan are suitable examples.
XV. Waxes such as beeswax, spermaceti, myristoyl myristate and stearyl stearate.
XVI. Beeswax derivatives, such as polyoxyethylene sorbitol beeswax. These are reaction products of beeswax with ethoxylated sorbitol of varying ethylene oxide content that form a mixture of ether-esters.
XVII. Vegetable waxes, including, but not limited to, carnauba and candelilla waxes.
XVIII. Phospholipids such as lecithin and derivatives.
XIX. Sterols. Examples include, but are not limited to, cholesterol and acyl esters of cholesterol.
XX. Amides, such as fatty acid amides, ethoxylated acyl amides and solid fatty acid alkanolamides.

The lotions of the invention additionally comprise from 1% to 10% of an emulsifier. The emulsifiers can be anionic, cationic or non-ionic.

Examples of non-ionic emulsifiers include, but are not limited to: fatty alcohols having 10 to 20 carbon atoms, fatty alcohols having 10 to 20 carbon atoms condensed with 2 to 20 moles of ethylene oxide or propylene oxide, alkyl phenols with 6 to 12 carbons in the alkyl chain condensed with 2 to 20 moles of ethylene oxide, mono- and di-acyl esters of ethylene glycol, wherein the fatty acid contains from 10 to 20 carbons, monoglycerides wherein the fatty acid contains from 10 to 20 carbons, diethylene glycol, polyethylene glycols of molecular weight 200 to 6000, polypropylene glycol of molecular weight 200 to 3000, glycerol, sorbitol, sorbitan, polyoxyethylene sorbitol, polyoxyethylene sorbitan and hydrophilic wax esters.

Suitable anionic emulsifiers include, but are not limited to, fatty acids saponified (soaps) with potassium, sodium, or triethanolamine, wherein the fatty acid contains from 10 to 20 carbons. Other suitable anionic emulsifiers include, but are not limited to, alkali metals, ammonium or substituted ammonium with alkyl sulfates, alkyl arylsulfonates and alkyl ethoxy ether sulfonates having 10 to 30 carbons in the alkyl chain and from 1 to 50 ethylene oxide units. Suitable cationic emulsifiers include quaternary ammonium and morpholinium and pyridinium compounds.

Some emollients previously described also have emulsifying properties. When a lotion contains one of these emollients, an additional emulsifier is not needed, though it can be included in the formulation.

The balance of the composition is water. The lotions are formulated by simply admixing all of the components together. Preferably, the compounds of Formula (I), (I'), (I''), (I''') or (I$^{IV}$) are dissolved in the emollient and the resulting mixture is added into the water. Optional components such as the emulsifier or common additives may be included in the composition.

A common additive is a thickening agent included at a level of 1% to 30% by weight of the composition. Examples of suitable thickening agents are: Cross-linked carboxypolymethylene polymers, methyl cellulose, polyethylene glycols, gums and bentonite.

Example 2

Preparation of Creams

The compositions of the present invention may be also formulated in the form of a cream. Creams contain from about 0.001% to about 30% of the components of Formula (I), (I'), (I''), (I''') or (I$^{IV}$), from 5% to 50% of an emollient and the adequate amount of water. The emollients described above in example 1 are also suitable for the cream formulation. Optionally, the cream may contain an emulsifier at a level from 3% to 50%. The emulsifiers described above in example 1 would also be suitable in this case.

Example 3

Preparation of Solutions

The compositions of the present invention may also be formulated in the form of a solution. Solutions contain from about 0.001% to about 30% of the compounds of Formula (I), (I'), (I''), (I''') or (I$^{IV}$) and the adequate amount of an organic solvent. Organic substances useful as the solvent or a part of the solvent system are as follows: propylene glycol, polyethylene glycol (200-600), polypropylene glycol (425-2025), glycerine, sorbitol esters, 1,2,6-hexanetriol, ethanol, isopropanol, diethyl tartrate, butanediol, and mixtures thereof. Such solvent systems can also contain water.

These compositions are applied on the skin in the form of a solution, or solutions are formulated in the form of aerosol and applied on the skin as a spray. Compositions in the form of aerosol additionally contain from 25% to 80% of a suitable propellant. Examples of propellants include, but are not limited to: chlorinated, fluorinated and fluorochlorinated low molecular weight hydrocarbons. Nitrous oxide and carbon dioxide are also used as propellant gases. Enough quantity to expel the content of the cartridge is used.

Example 4

Preparation of Gels

The composition in the form of gel could be obtained by simply adding a suitable thickening agent to the composition in the form of the solution described in example 3. The suitable thickening agents have already been described in example 1.

Gel formulations contain from about 0.001% to about 30% of the compounds of Formula (I), (I'), (I''), (I''') or (I$^{IV}$), 5% to 75% of a suitable organic solvent, 0.5% to 20% of a suitable thickening agent and the required amount of water.

Example 5

Preparation of Solids

The compositions of the present invention may also be formulated in solid form. Such forms have the shape of a bar intended for the application on the lips or other parts of the body. These compositions contain from about 0.001% to about 30% of the compounds of Formula (I), (I'), (I''), (I''') or (I$^{IV}$) and from 50% to 98% of an emollient such as the one described above. The composition may also contain from 1% to 20% of a suitable thickening agent, as those described in the previous examples, and, optionally, emulsifiers and water.

Additives usually found in topical compositions, such as preservatives (for example, methyl and ethyl paraben), dyes and perfumes may be included in any of the formulations described in examples 1-5.

The effective amount of 2,5-hydroxybenzene sulfonic used in topical form will vary according to the specific circumstances of application, the duration of exposition and similar considerations. In general, the amount will vary from 0.01 microgram to 50 micrograms of 2,5-dyhydroxybenzene sulfonic (Dobesilate) per square centimeter of the epidermis area. The amount of topical composition of 2,5-dihydroxybenzene sulfonic (Dobesitale) and the carrier applied on the affected area is determined according to the amount of 2,5-dihydroxybenzene sulfonic (Dobesilate) contained therein.

Example 6

Systematically Administered Compositions

The 2,5-dihydroxybenzene sulfonic (Dobesilate) is also useful when administered systemically, either orally or parenterally. The safe and effective required dose of 2,5-dihydroxybenzene sulfonic (Dobesilate) will vary according to the particular condition to be treated, the severity of the condition, the duration of the treatment and like factors within the specific knowledge and expertise of the pation or the attending physician and commensurate with the reasonable benefit/risk ration applicable to the use of any drug. The detailed systemic doses and dose ranges are based on the administration of 2,5-dihydroxybenzene sulfonic (Dobesilate) to a human 154 pound (70 kg) and may be adjusted to provide equivalent doses to patients of different weights. Oral doses may comprise from about 0.05 g to about 50 g per day, usually and preferably in fractionated doses.

The parenteral administration may be combined with an acceptable vehicle such as pyrogen-free sterile water, in doses from 0.5 mg to 200 mg of 2,5-dihydroxybenzene sulfonic (Dobesilate). Parenteral administration from 0.5 to 200 mg of 2,5-dihydroxybenzene sulfonic (Dobesilate) may be subcutaneous, intradermal, intramuscular, intraarticular or intravenous.

For oral administration, the 2,5-dihydroxibenzene sulfonic (Dobesilate) may be formulated in unit doses such as pills, capsules, tablets, granules, solutions, elixirs, chewing gums, chewable tablets, and the like. Suppositories manufactured by conventional methods may comprise 2,5- dihydroxibenzene sulfonic (Dobesilate). The forms of oral unit doses include 2,5-dihydroxibenzene sulfonic (Dobesilate) and a pharmaceutically acceptable vehicle. Each unit form would contain from about 15 mg up to about 2 g of 2,5-dihydroxybenzene sulfonic (Dobesilate) and a pharmaceutical vehicle. A pharmaceutically acceptable vehicle refers to a solid or liquid excipient, a diluent or an encapsulating substance. Examples of substances that may be useful as pharmaceutically vehicles of the 2,5-dihydroxybenzene sulfonic (Dobesilate) include: sugars such as lactose, glucose and sucrose, starches such as corn starch or potato starch, cellulose and derivatives thereof, such as sodium carboxymethylcellulose, ethylcellulose and cellulose acetate; powdered tragacanth; malt; gelatin; talc; magnesium stearate, stearic acid, calcium sulphate, vegetable oils such as peanut oil, cottonseed oil, sesame oil, olive oil, corn oil and *theobroma* oil, polyols such as propylene glycol, glycerin, sorbitol, mannitol and polyethylene glycol; agar; alginic acid; pyrogen-free water; isotonic saline; phosphate buffer solutions; cocoa butter, (suppository base) as well as other non-toxic compatible substances typically used on pharmaceutical formulations. Wetting agents and lubricants such as sodium lauryl sulfate, as well as coloring agents, flavoring agents and preservatives may also be present. Agents well known in the art for the preparation of enteric coatings may also be used in the oral formulation of the 2,5-dihydroxybenzene sulfonic (Dobesilate), so that it is released by the acid media of the stomach and absorbed through the intestinal wall.

The pharmaceutical vehicle used together with the 2,5-dihydroxybenzene sulfonic (Dobesilate) will be included at the necessary concentration to provide an adequate size-dose rate relation. Preferably, the vehicle shall comprise from 0.1% to 99% of the total weight of the composition.

Example 7

Hemangioma

Figure 1:
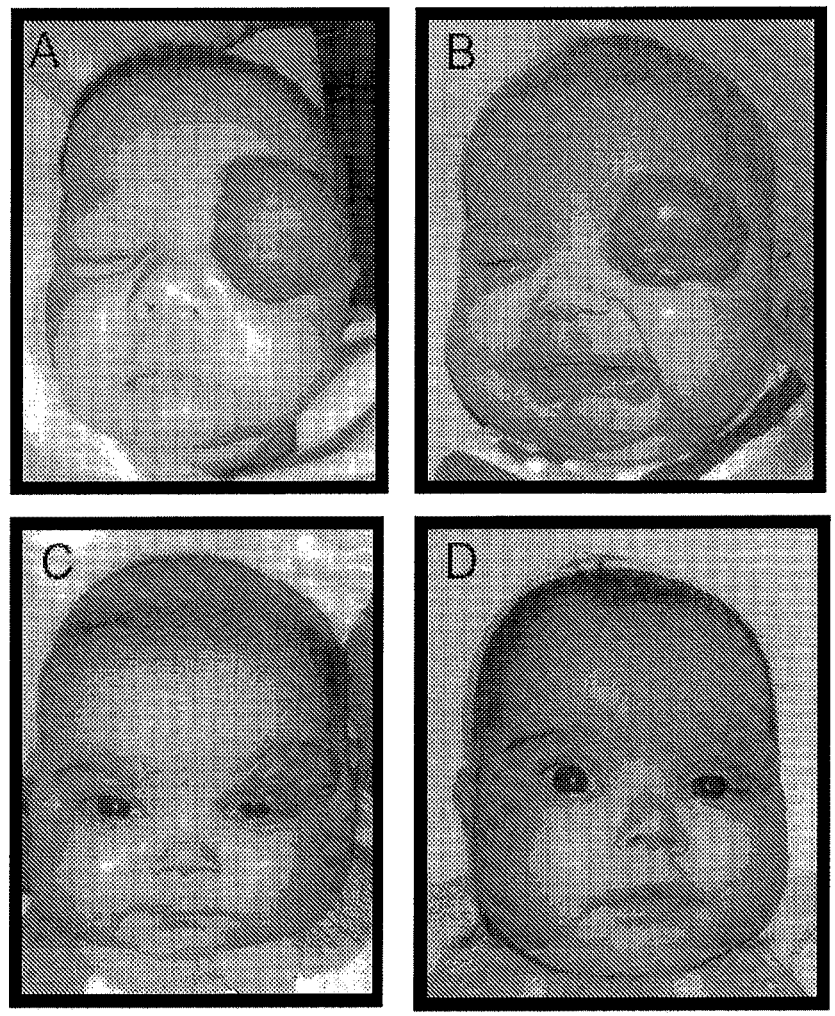
FIG. 1. Hemangioma.
Photographs of a child showing the effects of the topical treatment with a cream comprising 2,5-dihydroxybenzene-sulfonic (DHBS) (2.5%) in a baby suffering infantile hemangioma. Panel A shows the appearance of the child before treatment, and Panels B, C and D show the child after the topical treatment with 2,5 dihydroxybenzenesulfonic (DHBS) twice a day for 1, 2 and 3 months respectively.

The cream comprising 2,5-dihydroxybenzene sulfonic (2.5%) was topically applied twice a day for 3 months on the face of a child suffering from infantile hemangioma. FIG. 1A shows the child before the treatment and FIGS. 1B, 1C and 1D show the child after the treatment with said cream during 1, 2 and 3 months, respectively, evidencing a substantial recovery of the lesion.

Example 8

Hemangioblastoma

Figure 2:
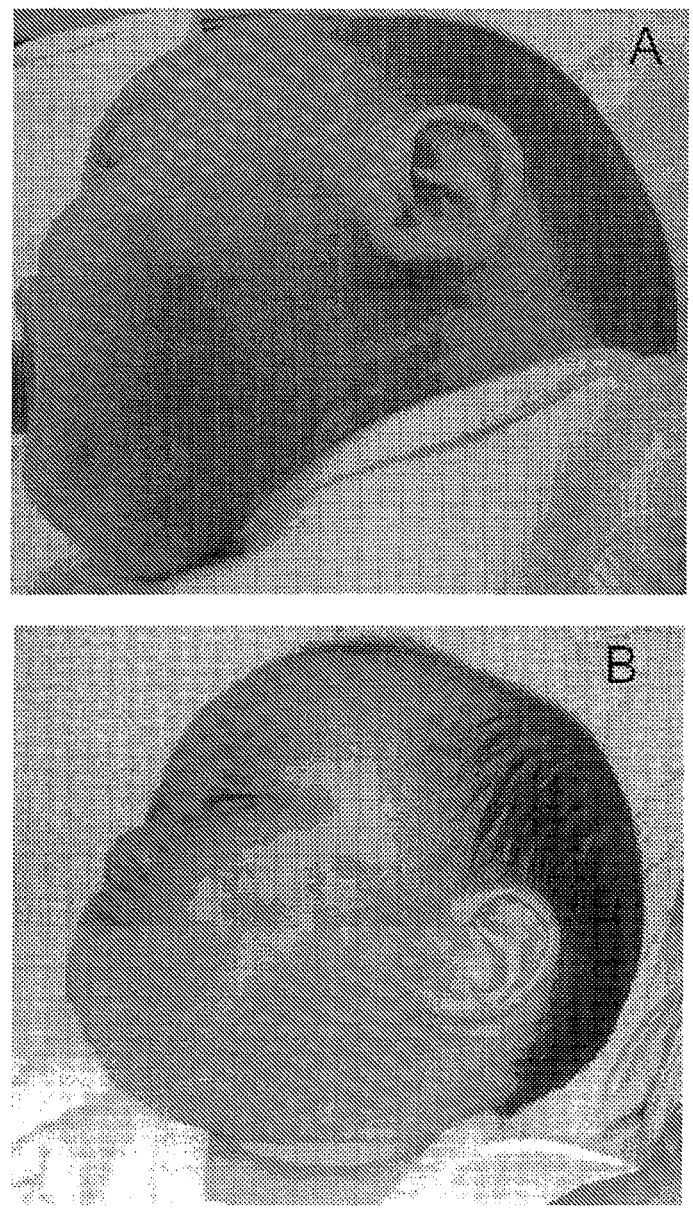
FIG. 2. Hemangioblastoma.

The cream comprising 2,5-dihydroxybenzene sulfonic (2.5%) was topically applied twice a day during 1 month on the face of the child suffering from Nakagawa angioblastoma. As shown in FIG. 2B, there is a reduction in the intensity of the reddish coloration caused by the lesion.

Example 9

Effect of the 2,5-Dihydroxybenzenesulfonic Acid (DHBS) on Pterygium

The 2,5-dihydroxybenzene sulfonate (DHBS) was formulated in a 2.5% solution, containing as inactive part: polyvinyl alcohol (14 mg/ml), benzalkonium chloride (0.05 mg/ml), sodium chloride, monosodium phosphate, disodium phosphate, sodium edetate and purified water. The solution was applied topically to a patient suffering from unilateral pterygium, as one drop four times per day. The application of DHBS for two weeks produced a partial reversal of the pterygium, as shown in FIG. 3. This example demonstrates the efficacy of DHBS in the treatment of pterygium.

Example 10

Efficacy of 2,5-Dihydroxybenzene Sulfonic Acid in Endometriosis

Sprague-Dawley rats were anesthetized as described (Fernandez-Tornero C et al. *J Biol Chem*, 2003). Endometriotic lesions were induced using a known rat model of endometriosis (Vernon M W and Wilson E A. *Fertil Steril*, 1985). In summary, 2 mm fragments of the cervix were autologously implanted between branches in the mesenteric vascular tree. The rats were treated or not treated (control) daily during two weeks after the surgery with 2,5-dihydroxybenzene sulfonic acid (DHBS) (200 mg/kg; i.p.). Then, the rats were sacrificed and the endometrial ectopic tissue was removed to make its histological examination. The staining was performed with hematoxylin-eosin; this method evidenced the athrophy of the cervix tissue implanted in the rats with 2,5-dihydroxybenzene sulfonic (DHBS), FIG. 4B. In opposite, the cervix tissue in untreated rats revealed a viable endometrium and myometrium with high angiogenic activity, FIG. 4A. This example illustrates the therapeutic activity of 2,5-dihydroxybenzene sulfonate (DHBS) in the treatment of endometriosis.

Example 11

Effect of 2,5-Dihydroxybenzene Sulfonic on Angiogenesis Induced by *Helicobacter pylori* in the Human Gastric Mucosa A biopsy of the gastric mucosa was performed in a patient chronically infected with *Helicobacter pylori* before the oral treatment with 2,5-dihydroxybenzene sulfonic acid (Dobesilate) (500 mg/day). After a week of treatment, another biopsy was performed in the patient. Both biopsies were evaluated using hematoxylin-eosin staining. Under pre-treatment conditions, FIG. 5A, the gastric mucosa exhibited symptoms of congestion and erythema. Microscopically, the arrows and the asterisk indicate the formation of neovessels in the mucosa protruding the gastric lumen through the lost epithelial layer. After the treatment with 2,5-dihydroxybenzenesulfonic (DHBS) (FIG. 5B), the symptoms of congestion and erythema disappear, the epithelial membrane is apparently normal and there is less angiogenic activity. This example illustrates that the use of DHBS is beneficial in the treatment of gastritis and angiogenesis caused by the infection with *Helicobacter pylori*.

Example 12

Effect of 2,5-Dicetoxybenzenesulfonic on the Treatment of the Intestinal Inflammatory Disease Induced in the Mouse The induction of the intestinal inflammatory disease described below is a representative model for the evaluation of therapeutic strategies to treat Crohn's disease and ulcerative colitis. 7-8 week old female mice of strain C57BL/6J-664 were used. The intestinal inflammatory disease (IID) was induced by feeding the mice with 3% dextran sulfate sodium (DSS; MW 40,000) dissolved in drinking water in 2 cycles. Each cycle consisted of 7 days with 3% DSS in the drinking water separated by 7 days with regular water. A daily clinical evaluation of the animals was performed in which the body weight, the consistency of the faeces and the presence of blood in the faeces were determined. Thus, the validated score of the clinical activity of the disease was evaluated with a 0 to 6 scale, considering the following parameters: consistency of the faeces, presence or absence of fecal blood and loss of weight.

At the end of the first cycle of exposure to DSS, the mice were divided into the following treatment groups: a first group was administered intraperitoneal (i.p) injections of vehicle (0.9% NaCl). Another group received intramuscular injections of Solu-Medrol, a standard IID treatment, at a dose of 10 mg/kg/day. A third group was administered i.p. injections of potassium 2,5-diacetroxybenzene sulfonate (DABS, 100 mg/kg/day). The last group was treated orally with 125 mg/kg day of DABS.

As shown in FIG. 6, the loss of weight produced by the two cycles of exposure to DSS is reduced by the treatment with DABS. DABS treatment beneficially affects the IID clinical course, as demonstrated by the determination of the disease clinical score (FIG. 7) that is reduced due to the i.p. and the oral administration of DABS in the first two DSS cycles. Furthermore, it is shown that the efficacy of DABS is not lower (in some points it is higher) than the one corresponding to the standard treatment with Solu-Medrol (FIGS. 6 and 7).

Example 13

Effect of Potassium 2,5-Diacetoxybenzene Sulfonate on the Treatment of Experimentally Induced Asthma in Mice 6-9 week old Balb/c mice were used. The ovoalbumin (OVA)/aluminum complex was obtained after dissolving OVA (500 μg/mL) in PBS, and mixing it with an equal volume of 10% aluminum potassium sulfate at pH 6.5 for 1 hour. After centrifuging the pellet (750×g for 5 minutes) the OVA/aluminum pellet was resuspended in distilled water. On day 0, the mice were injected intraperitoneally injected with 100 μg of OVA/aluminum. Eight days later, the mice were anesthetized and exposed to 250 μg of OVA. Later, they were administered 125 μg of OVA on days 15, 18 and 21. Each rat received sublingual administration of OVA.

The following treatments were administered to the animals: (i.p.) vehicle from day 2, potassium 2,5-diacetoxybencene sulfonate (DABS; 100 mg/kg/day, i.p.) from day 2, DABS (100 mg/kg/day, i.p.) from day 8 and Combivent (20 μg/200 μg in aerosol) on days 20, 21 and 22, the latter as a reference treatment.

In order to evaluate the pulmonary function, the response to methacholine in conscious mice was determined, 24 hours after the last exposure to OVA. The mice were exposed to increasing methacholine concentrations (5 and 20 mg/mL) in the form of aerosol using an ultrasonic nebulizer during 2 minutes. The degree of bronchoconstriction was expressed as the enhanced pause ($P_{enh}$) which correlates to the mouse air resistance, impedance and pressure within the pleura. The $P_{enh\ enh}$ was calculated using the formula $P_{enh}=[(L/R_t-1) \times (PEF/PIF)]$, where Te is expiratory time, Rt is relaxation time, PEF is peak expiratory flow and PIF is peak inspiratory flow x 0.67 coefficient.

After measuring airway hyperreactivity, the mice were sacrificed and the bronchoalveolar lavage (BAL) of the right lung was collected. The total number of cells in the BAL fluid was determined.

Figure 8:
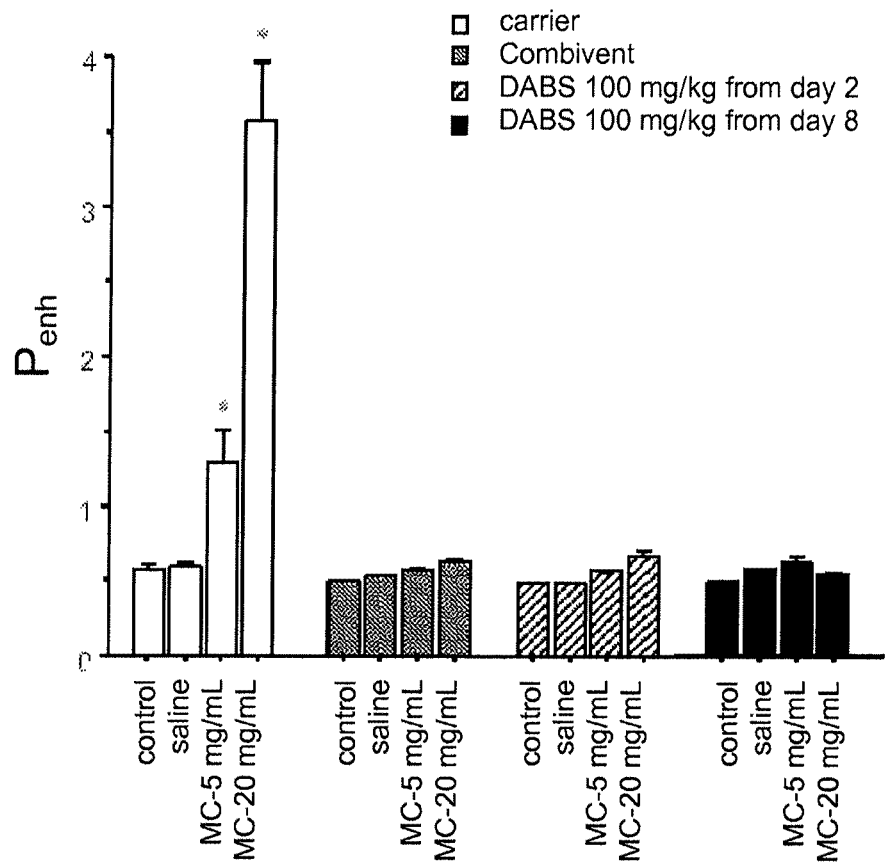
Figure 9:
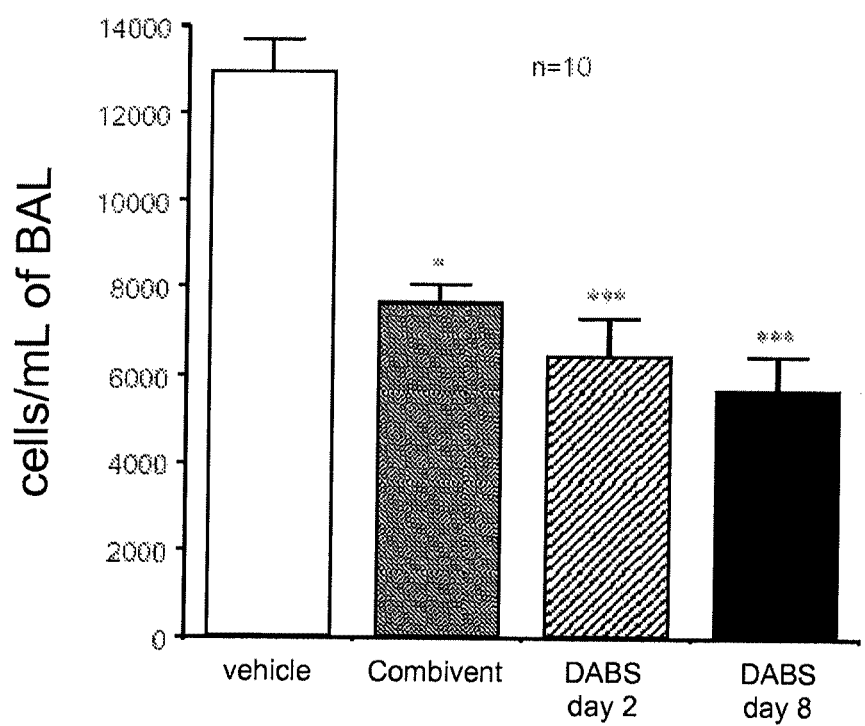

The treatment with DABS, when it started on day 2 and when it started on day 8, completely prevented the methacoline induced bronchoconstriction in OVA-sensitized mice (FIG. 8). Likewise, the DABS treatment significantly reduced the presence of BAL cells in asthmatic mice, even more than the treatment with Combivent (FIG. 9).

Example 14

Use of 2,5-Dihydroxybenzene Sulfonic Acid (DHBS) for the Treatment of Skeletal Muscle Lesions The capacity of a 2,5-dihydroxybenzene derivative, the 2,5-dihydroxybenzene sulfonic acid (DHBS) to effectively treat skeletal muscle lesions is shown herein. The efficacy is evident, not only in the images of conventional diagnosis that show the recovery of the muscular damage, but also there is a clear functional recovery of the affected limb.

This example supports the use of 2,5-dihydroxybenzene derivatives in the treatment of skeletal muscle lesions as well as muscle-tendinous and muscle-ligamentous injuries.

The first patient's left quadriceps was broken by practicing sports. Two days after the muscle was broken, the magnetic resonance imaging (MRI) reveals a lesion with an considerably large hematoma (FIGS. 10A and 10B). At that moment, the patient starts a daily oral treatment with 500 mg of 2,5-dihydroxybenzene sulfonic acid (DHBS) for two weeks. After this period, a new magnetic resonance is performed and it reveals the recovery of the lesion in the quadriceps, the hematoma can no longer be observed (FIGS. 10C and 10D). Besides, at that moment, the patient is able to extend the left leg almost completely (FIGS. 11A and 11B). This functional recovery, as well as the diagnostic resolution of the lesion occur within a shorter period than the one required in the case of conventional treatments (antiinflammatories) after a lesion of this magnitude. An observation that may be applied to the other cases that support this example.

Other patient has an hematoma and muscular breaking of the brachial biceps, as shown in the magnetic resonance image (MRI) of FIG. 12A. The hematoma can be appreciated externally (FIG. 13A) and the lesion, produced by professional practice (dancing) the day before the consultation, limits the elbow flexion (FIG. 13B) and extension (FIG. 13C). The treatment with DHBS (1500 mg/day, p.o.) during 20 days markedly reduces the size of the lesion and of the hematoma (FIG. 12B) and recovers the functionality of the elbow flexion and extension (FIGS. 13D and 13E).

The treatment with DHBS (1500 mg/day, p.o.) for 11 days reduced the muscular lesion of another patient, produced in the semitendinous muscle by practicing sports 9 days before starting the treatment with DHBS. In FIG. 14, the magnetic resonance image shows the upper part of the left leg of the patient before (A) and after (B) the treatment with DHBS.

In another case, the magnetic resonance image of the breaking produced in a patient's Achilles tendon (FIG. 15A) is shown, as well as the marked reduction of said lesion after two months of treatment with DHBS (1500 mg/day, p.o.) (FIG. 15B).

Example 15

Effect of the Treatment with Potassium 2,5-Dihydroxybenzensulfonate and Potassium 2,5-Diacetoxybenzenesulfonate on the Experimental Infection with *Leishmania major* in a Mouse Model This model is based in the massive inoculation of *Leishmania* promatigotes in the mouse paw pad. Under these conditions, the parasite induces a progressive inflammation correlated with the multiplication of parasites at the site of inoculation. BALB/c strain female mice that developed severe and uncontrolled injuries were used (Foote S J, Handman E. *Brief Funct Genomic Proteomic*, 2005). This model has been used in pharmacology to monitor the therapeutic capacity of new leishmanicide compounds and the preventive capacity of potential vaccines against leishmaniasis ((Nelson K G et al. *Antimicrob Agents Chemother.* 2006).

The animals were inoculated with $5 \times 10^6$ of *L. major* promastigotes (strain Hervás) in 50 μL of PBS into the plantar pad of the right back paw. As negative control of the infection, a group of mice inoculated with 50 μL of PBS was used. The sizes of the lesions were measured every 7 days until the animals were sacrificed (week 9) using a Vernier caliper. The thickness of the right back paw (infected) and the left back paw (uninfected) of all the animals was measured at the base of the fifth toe. The progression of the inflammation is represented as the difference in thickness between the infected and the non-infected paws.

In a first assay, the infected animals were daily injected by the intraperitoneal (i.p.) route with 100 μL of saline (0.9% NaCl in $H_2O$) (vehicle) or with 4 mg of potassium 2,5-dihydroxybenzene sulfonate (DHBS; 200 mg/kg of weight) in 100 μL of saline during 14 days from the third week after the infection. A significant reduction in the increase of paw thickness was observed from the eighth week after the infection (FIG. 16).

In another assay, the infected animals were administered a daily intraperitoneal (i.p.) injection of 100 μL of saline (0.9% NaCl in H$_2$O) (vehicle) or of 4 mg of potassium 2,5-diacetoxybenzene sulfonate (DABS; 200 mg/kg of weight) in 100 μL of saline. Such treatment started simultaneously with the infection (day 0) and continued until the animals were sacrificed in the week 9 post-infection. As shown in FIG. 17, the treatment with DABS produces a statistically significant reduction in the size of the lesion as from the third week post-infection up to the end of the assay. Said differences increase during the experiment.

In a third assay, the treatments used were the same as the previous assay (vehicle and DABS 200 mg/kg/day i.p.), but were administered from the third week after the inoculation. The size of the lesion was significantly smaller in the group treated with DABS as from the eighth week after the infection (FIG. 18).

Example 16

Effect of 2,5-Dihydroxybenzoic Acid (Gentisic Acid) on Human Corneal Angiogenesis The potassium 2,5-dihydroxybenzoate was formulated in a 5% solution, containing as inactive part: polyvinyl alcohol (14 mg/ml), benzalkonium chloride (0.05 mg/ml), sodium chloride, monosodium phosphate, disodium phosphate, sodium edetate and purified water. 4 drops a day were topically applied in a patient that presented a corneal neovascularization process refractory to any type of previous treatment.

The application of 2,5-dihydroxybenzoate during 19 days produced a remarkable reduction in the degree of corneal vascularization, as shown in FIG. 19.

The esters of 2,5-dihydroxybenzene sulfonate described in the present invention are not mere prodrugs for the final administration of the 2,5-dihydroxybenzen sulfonate. The following examples illustrate that these compounds surprisingly exert pharmacological actions of interest in the present invention by themselves, without the need of converting them in 2,5-dihydroxybenzene sulfonate.

Example 17

Inhibition of Fibroblasts Mitogenesis Induced by the Fibroblast Growth Factor-1 (FGF-1)

Inhibition of FGF-1 induced mitogenesis was observed in quiescent cultures of Balb/c 3T3 fibroblasts by 2-acetoxy-5-hydroxybenzene sulfonate (FIG. 20), 5-acetoxy-2-hydroxybenzene sulfonate (FIG. 21) and 2,5-diacetoxybenzene sulfonate (FIG. 22). The evaluated compounds were used in the form of potassium salt, except in the first case in which calcium salt was used. The experiments were carried out as described in Fernandez-Tornero C et al. *J Biol Chem*, 2003.

Example 18

Effect of Monoesters of 2,5-Dihydroxybenzene Sulfonate on the Proliferation of Rat Glioma C6 Cells The following example shows the efficacy of 2,5-dihydroxybenzene sulfonic, potassium 2-acetoxy-5-hydroxybenzene sulfonate (2A-5HBS) and potassium 5-acetoxy-2-hydroxybenzene sulfonate (5A-2HBS) monoesters to reduce the proliferative capacity of glioma cells and supports the use of the compound in treating gliomas.

The cell line used was the C6 cell line and the experiment was carried out as described in examples 2 and 3. Once adhered, the cells were treated or not (controls) with (5A-2HBS) (500 μM) or (2A-5HBS) (500 μM) and they were allowed to proliferate for 48 h. After this time the glioma cell proliferation was evaluated by means of staining the fixed cells with crystal violet. The number of cells is proportional to the amount of retained dye, which was determined spectrophotometrically by measuring the absorbance at 595 nm once the dye was extracted from the cells. Both 2,5-dihydroxybenzene sulfonate, (5A-2HBS) and (2A-5HBS) monoesters caused the inhibition of rat glioma cell proliferation (FIG. 23).

Example 19

Analysis of the Structural Interaction of the Esters of 2,5-Dihydroxybenzene Sulfonate with the Fibroblast Growth Factor-1 (FGF-1)

Based on the crystal diffraction of the FGF-1:2-acetoxy-5-hydroxybenzene sulfonic acid, FGF-1:5-acetoxy-2-hydroxybenzene sulfonic acid and FGF-1:2,5-diacetoxybenzene sulfonic acid complexes, the structures of the complexes were calculated and represented. FIGS. 24, 25 and 26, which show the surface of the dyed protein according to its electrostatic potential (light grey: negative charge; dark grey: positive charge; white: lack of charge), show the manner in which 2-acetoxy-5-hydroxybenzene sulfonic acid, 5-acetoxy-2-hydroxybenzene sulfonic acid and 2,5-diacetoxybenzene sulfonic acid interact, respectively, with FGF-1. The electron density of the compound, contoured at 1σ (FIGS. 24-26, panels C), allowed locating and determining the orientations of the compounds with respect to the protein (FIGS. 24-26, panels A and B), as well as confirming that the compounds conserve the acetoxyl groups in positions 2, 5 and, 2 and 5, respectively, when they bind to the protein. The compounds occupy a site that is very close to the one that has been described occupied by 2,5-dihydroxybenzene sulfonic acid, the aromatic ring of which forms a cation-π bond with the N$^ε$ group of lysine 132, which is marked in FIGS. 24-26, panels A, as a reference.

Example 20

Effect of Monoesters of 2,5-Dihydroxybenzenesulfonate on the Proliferation of Human Retinal Endothelial Cells Endothelial proliferation is required for angiogenesis. The following example shows the efficacy of the monoesters of 2,5-dihydroxybenzenesulfonic, calcium 2-acetoxy-5-hydroxybenzenesulfonate (2A-5HBS) and potassium 5-acetoxy-2-hydroxybenzenesulfonate (5A-2HBS) to reduce the proliferation capacity of human retinal endothelial cells and supports the use of the compounds in the treatment of ocular neovascularizations.

Primary cultures of human retinal endothelial cells (HREC) were used. Cells were obtained from Cell Systems (Virginia, USA) and subcultured with CSC complete medium (Cell Systems). Cells at 2 to 5 passages were seeded in 24-well plates at 7,500 cells/well density and, once attached, the cells were treated o not treated (controls) with 2A-5HBS (500 and 1000 μM) or 5A-2HBS (500 and 1000 μM) and they were allowed to proliferate for 72 hours, with daily medium changes. After that, the proliferation of HREC was evaluated by staining the fixed cells with crystal violet. The number of cells is proportional to the amount of retained dye, which was spectrophotometrically determined by measuring absorbance at 595 nm after removing the dye from the cells. Data are expressed as the percentage of absorbance at 595 nm obtained in control conditions. Data were obtained from two different experiments performed in triplicate.

Both mono esters of 2,5-dihydroxybenzenesulfonate caused the inhibition of the proliferation of HREC. The compound esterified in position 2, (2A-5HBS) causes significant inhibition of HREC proliferation at 500 and 1000 μM concentrations, while the inhibitory effect of the compound esterified in position 5 (5A-2HBS) shows significant effects at 1000 μM concentration (FIGS. 27 and 28).

Example 21

Effect of 2,5-Dihydroxycinnamic Acid Methyl Ester and 2,5-Dihydroxybenzenesulfonate on the Proliferation of Human Retinal Endothelial Cells Endothelial proliferation is required for angiogenesis. The following example shows the efficacy of 2,5-dihydroxycinnamic acid methyl ester (2,5-DHCME) to reduce the proliferation capacity of human retinal endothelial cells and supports the use of the compound in the treatment of ocular neovascularizations.

Primary cultures of human retinal endothelial cells (HREC) were used. Cells were obtained from Cell Systems (Virginia, USA) and subcultured with CSC complete medium (Cell Systems). Cells at 2 to 5 passages were seeded in 24-well plates at 7,500 cells/well density and, once attached, the cells were treated o not treated (controls) with 2,5-DHCME (50 and 100 μM) and they were allowed to proliferate for 72 hours, with daily medium changes. Under the same conditions, other cultures were treated with calcium 2,5-dihydroxybenzenesulfonate (DHBS; 100 μM) for comparison. After that, the proliferation of HREC was evaluated by staining the fixed cells with crystal violet. The number of cells is proportional to the amount of retained dye, which was spectrophotometrically determined by measuring absorbance at 595 nm after removing the dye from the cells. Data are expressed as the percentage of absorbance at 595 nm obtained in control conditions. Data were obtained from two different experiments performed in triplicate.

2,5-DHCME causes significant inhibition of HREC proliferation at 50 and 100 μM concentrations, while DHBS failed to significantly affect HREC proliferation at 100 μM concentration (FIG. 29).

Each patent, patent application, and publication cited or described in the present application is hereby incorporated by reference in its entirety as if each individual patent, patent application, or publication was specifically and individually indicated to be incoporated by reference.

While specific embodiments of the subject invention have been discussed, the above specification is illustrative and not restrictive. One skilled in the art will appreciate that numerous changes and modifications can be made to the invention, and that such changes and modifications can be made without departing from the spirit and scope of the invention. The full scope of the invention should be determined by reference to the claims, along with their full scope of equivalents, and the specification, along with such variations.

The invention claimed is:

1. A method of treating arthritis and pain, wherein the arthritis is osteoarthritis and the pain is inflammatory pain, comprising administering to an individual in need thereof a pharmaceutically effective amount of a compound of Formula (I''') or pharmaceutically acceptable salt thereof, wherein the compound of Formula (I''') is:

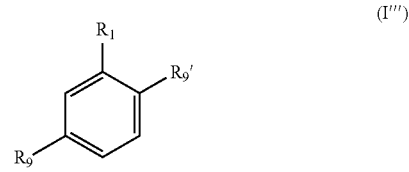

wherein:
R$_1$ is —(CH$_2$)$_a$ Y;
Y is —SO$_3$H,
R$_9$ and R$_{9'}$ are independently selected from —OH and —OR$_2$, wherein at least one of R$_9$ and
R$_{9'}$ is an unsubstituted alkylcarbonyloxy group, and wherein when R$_9$ and
R$_{9'}$ are both —OR$_2$, then said R$_9$ and R$_{9'}$ can be the same or different;
R$_2$ is an unsubstituted alkylcarbonyl group; and
a is a number selected from 0, 1.

2. The method of claim 1, wherein R$_2$ is methylcarbonyl.

3. The method of claim 1, wherein the compound of Formula (I''') is administered topically, transdermally, orally, buccally, parenterally, by inhalation, rectally, intravaginally, intraocularly, otically or intraarticularly.

4. The method of claim 1, further comprising the administration of at least one additional therapeutic agent.

5. The method of claim 4, wherein the at least one additional therapeutic agent is selected from the group consisting of: a chemotherapeutic agent, a corticosteroid, an antibiotic, an analgesic, an alpha-adrenergic blocker, a beta-adrenergic agonist, an anticholinergic, an inhibitor of 5-alpha-reductase, an antiandrogen, an immunomodulator, an immunosuppressant, an anti-angiogenic such as anti VEGF, anti FGF, anti HGF and anti EFG; a leukotriene modifier, an aminosalicylate, an anesthetic, a non-steroidal anti-inflammatory, an antiparasitic, a therapy of the solubilized interleukin receptor, intramuscular gold, a cytotoxic, an antioxidant, and combinations of two or more thereof.

6. The method of claim 1, wherein the compound of formula (I''') is selected from the group consisting of:
2-(acetyloxy)-5-hydroxybenzenesulfonic acid; 5-(acetyloxy)-2-hydroxybenzenesulfonic acid and 2,5-bis(acetyloxy)benzenesulfonic acid.

7. The method of claim 1, wherein the compound of Formula (I''') is selected from the group consisting of:
2-(acetyloxy)-5-hydroxybenzenehomosulfonic acid;
5-(acetyloxy)-2-hydroxybenzenehomosulfonic acid; and
2,5-bis(acetyloxy)benzenehomosulfonic acid.

* * * * *